US006294325B1

(12) United States Patent
Wetmur

(10) Patent No.: US 6,294,325 B1
(45) Date of Patent: Sep. 25, 2001

(54) CLONING AND EXPRESSION OF THERMOSTABLE MULTI GENES AND PROTEINS AND USES THEREOF

(75) Inventor: James G. Wetmur, Scarsdale, NY (US)

(73) Assignee: The Mount Sinai School of Medicine of the City University of New York, New York, NY (US)

( * ) Notice: Subject to any disclaimer, the term of this patent is extended or adjusted under 35 U.S.C. 154(b) by 0 days.

(21) Appl. No.: 08/676,444

(22) Filed: Jul. 5, 1996

(51) Int. Cl.$^7$ .............................. C12Q 1/68; C07K 15/26

(52) U.S. Cl. ................................. 435/6; 530/350

(58) Field of Search .................. 435/6, 91.2; 536/23.1; 530/350

(56) References Cited

U.S. PATENT DOCUMENTS 5,877,280 * 3/1999 Wetmur ..................................... 435/6

FOREIGN PATENT DOCUMENTS

| WO 93/22462 | 11/1993 | (WO) . |
| WO 95/12688 | 5/1995 | (WO) . |
| WO 95/16793 | 6/1995 | (WO) . |
| WO 95/29258 | 11/1995 | (WO) . |

OTHER PUBLICATIONS

Mankovich, J.A., et al., "Nucleotide Sequence of the *Salmonella typhimurium MutL* Gene Required for Mismatch Repair: Homology of MutL to HexB of *Streptococcus pneumoniae* and to PMS1 of the Yeast *Saccharomyces cerevisiae*," J. Bacteriology, 171(10) :5325–5331 (1989).
Prudhomme, M., et al., "Nucleotide Sequence of the *Streptococcus pneumoniae hexB* Mismatch Repair Gene: Homology of HexB to MutL of *Salmonella typhimurium* and to PMS1 of *Saccharomyces cerevisiae*," J. Bacteriology, 171(10) :5332–5338 (1989).
Kramer, W., et al., "Cloning and Nucleotide Sequence of DNA Mismatch Repair Gene PMS1 from *Saccharomyces cerevisiae*: Homology of PMS1 to Procaryotic MutL and HexB," J. Bacteriology, 171 (10): 5339–5346 (1989).
Tiffany, H–C, et al., "Nonconserved Segment of the MutL Protein from *Escherichia coli* K–12 and *Salmonella typhimurium*," Nucleic Acids Research, 20(9) :2379 (1992).
Worth, L., et al., "Mismatch Repair Proteins MutS and MutL Inhibit RecA–catalyzed Strand Transfer Between Diverged DNAs," Proc. Natl. Acad. Sci. USA, 91:3238–3241 (1994).
Su, S. and Modrich, P., "*Escherichia coli* mutS–encoded protein binds to mismatched DNA base pairs", Proc.Natl.Acad.Sci.USA, 83:5057–5061 (1986).
Jiricny, J., et al., "Mismatch–containing oligonucleotide duplexes bound by the *E. coli* mutS–encoded protein", Nucleic Acids Research, 16(16) :7843–7853 (1988).

Lishanski, A., et al., "Mutation detection by mismatch binding protein, MutS, in amplified DNA: Application to the cystic fibrosis gene", Proc.Natl.Acad.Sci.USA, 91: 2674–2678 (1994).
Fishel, R., et al., "Binding of Mismatched Microsatellite DNA Sequences by the Human MSH2 Protein", Science, 266:1403–1405 (1994).
Worth, L. Jr., et al., "Mismatch repair proteins MutS and MutL inhibit RecA–catalyzed strand transfer between diverged DNAs", Proc.Natl.Acad.Sci.USA, 91:3238–3241 (1994).
Holland, P.M., et al., "Detection of specific polymerase chain reaction product by utilizing the 5'→3' exonuclease activity of *Thermus aquaticus* DNA polymerase", Proc.Natl.Acad.Sci.USA, 88:7276–7280 (1991).
Ellis, L.A., et al., "MutS binding protects heteroduplex DNA from exonuclease digestion in vitro: a simple method for detecting mutations", Nucleic Acids Research, 22(13) :2710–2711 (1994).
Saiki, R.K., et al., "Primer–Directed Enzymatic Amplification of DNA with Thermostable DNA Polymerase", Science, 239: 487–491 (1988).
Brown, P.O., "Genome scanning methods", Current Opinionsin Genetics and Development 4 :366–373 (1994).
Jonsson, J.J. and Weissman, S.M., "From mutation mapping to phenotype cloning", Proc.Natl.Acad.Sci. USA 92 :83–85 (1995).
Hayashi, K. and Yandell, D.W., "How Sensitive Is PCR–SSCP?", Human Mutation 2 :338–346 (1993).
Youil, R., et al., "Screening for mutations by enzyme mismatch cleavage with T4 endonuclease VII", Proc.Natl.Acad.Sci. USA 92 :87–97 (1995).

(List continued on next page.)

Primary Examiner—Eggerton A. Campbell
(74) Attorney, Agent, or Firm—Hamilton, Brook, Smith & Reynolds, P.C.

(57) ABSTRACT

Isolated nucleic acids which encode a thermostable protein that enhances specific binding of a thermostable mismatch binding protein to bulge loops in a heteroduplex nucleic acid and recombinant vectors comprising nucleic acid which encodes a thermostable protein that enhances specific binding of a thermostable mismatch binding protein to bulge loops in a heteroduplex nucleic acid are disclosed. Also disclosed are isolated thermostable proteins that enhance specific binding of a thermostable mismatch binding protein to bulge loops in a heteroduplex nucleic acid and host cells comprising a recombinant gene which can express a thermostable protein that enhances specific binding of a thermostable mismatch binding protein to bulge loops in a heteroduplex nucleic acid. Further disclosed are methods of reducing DNA misincorporation in an amplification reaction, methods for detecting a nucleic acid which includes a specific sequence, methods for amplifying a nucleic acid comprising a specific sequence, and methods for selecting against a nucleic acid comprising specific sequence.

4 Claims, 13 Drawing Sheets

OTHER PUBLICATIONS

Hsu, I.-C., et al., "Detection of DNA point mutations with DNA mismatch repair enzymes", *Carcinogenesis* 15(8):1657–1662 (1994).

Fishel, R., et al., "Purified Human MSH2 Protein Binds to DNA Containing Mismatched Nucleotides", *Cancer Research* 54 :5539–5542 (1994).

Wagner, R., et al., "Mutation detection using immobilized mismatch binding protein (MutS)", *Nucleic Acids Research* 23 (19) :3944–3948 (1995).

Biswas I., et al., "Identification and Characterization of a Thermostable MutS Homolog from *Thermus aquaticus*", J. of Biol. Chem. 271 (9) :5040–4048 (1996).

Takamatsu, S., et al., "Mismatch DNA recognition protein from an extremely thermophilic bacterium, *Thermus thermophilus* HB8", *Nucleic Acids Research* 24 (4):640–647 (1996).

Grilley, M., et al., "Isolation and Characterization of the *Escherichia coli* mutL Gene Product"*J. Biol. Chem.* 264 (2) :1000–1004 (1989).

Parker, B., et al., "Repair of DNA heteroduplexes containing small heterologous sequences in *Escherichia coli*", *Proc. Natl. Acad. Sci. USA* 89:1730–1734 (1992).

Livak, K.J., et al., "Towards fully automated genome–wide polymorphism screening", *Nature Genetics* 9:341–342 (1995).

Holland, P.M., et al., "Detection of Specific Polymerase Chain Reaction Product by Utilizing the 5'→3' Exonuclease Activity of *Thermus aquaticus* DNA Polymerase", *Clin. Chem.*38 (38) :462–463 (1992).

Lee, L.G., et al., "Allelic discrimination by nick–translation PCR with fluorogenic probes", *Nucleic Acids Research* 21 (16):3761–3766 (1993).

Grilley, M., et al., "Mechanisms of DNA–mismatch correction", *Mutation Research* 236:253–267 (1990).

Bottema, C.D.K., et al.,"Polymerase Chain Reaction Amplification of Specific Alleles: A General Method of Detection of Mutations, Polymorphisms, and Haplotypes", *Methods in Enzymology* 218:388–402 (1993).

* cited by examiner

Apy MutS CODING SEQUENCE

```
   1  ATGGGAAAAG AGGAGAAAGA GCTCACCCCC ATGCTCGCCC AGTATCACCA
  51  GTTCAAGAGC ATGTATCCCG ACTGCCTTCT TTTATTCAGG CTCGGGGACT
 101  TTTACGAGCT CTTTTACGAG GACGCGGTCG TCGGTTCTAA AGAGCTCGGT
 151  CTAGTTCTAA CTTCAAGACC CGCGGGAAAG GGAAGGGAAA GGATTCCCAT
 201  GTGCGGTGTT CCCTACCATT CTGCAAACAA CTATATAGCA AAGCTCGTTA
 251  ATAAGGGATA CAAGGTAGCA ATATGCGAGC AGGTTGAGGA CCCCTCAAAG
 301  GCAAAGGGAA TAGTAAAGAG GGACGTAATA AGAGTTATAA CACCTGGGAC
 351  CTTTTTTGAG AGGGAAACGG GAGGGCTTTG CTCCCTTTAC AGGAAGGGAA
 401  AGAGCTATCT CGTTTCTTAT CTTAACCTCT CGGTAGGTGA GTTCATAGGT
 451  GCAAAGGTAA AGGAGGAAGA GCTCATAGAC TTCCTCTCAA AGTTCAACAT
 501  AAGGGAGGTT CTTGTAAAGA GGGAGAAAA GCTCCCCGAA AAGCTTGAGA
 551  AGGTTCTAAA GCTCCACATA ACGGAGCTTG AAGAGGAGTT CTTTGAGGAG
 601  GGAAAGGAGG AGCTTCTTAA GGATTACGGA GTTCCGTCGA TAAAAGCCTT
 651  CGGCTTTCAG GATGAGGATT TATCCCTTTC CCTCGGGGCT GTTTACAGGT
 701  ATGCAAAGGC GACACAGAAA TCTTTTACCC CTCTCATTCC AAAGCCCAAA
 751  CCTTACGTTG ACGAGGGATA CGTAAAGCTT GACCTCAAGG CAGTCAAAGG
 801  TCTTGAGATT ACCGAAAGCA TAGAAGGAAG AAAGGATTTA TCCCTGTTTA
 851  AGGTCGTTGA CAGAACCCTC ACGGGTATGG GGAGAAGGAG GCTGAGGTTC
 901  AGGCTTCTAA ACCCCTTCAG GAGCATAGAG AGAATAAGGA AGGTTCAGGA
 951  AGCAGTTGAG GAGCTAATAA ACAAGAGGGA GGTTCTGAAC GAGATAAGGA
1001  AAACCCTTGA GGGTATGTCC GACCTTGAGA GACTCGTATC CAGGATAAGC
1051  TCAAACATGG CAAGCCCAAG AGAACTTATA CACCTCAAAA ACTCCCTAAG
1101  GAAGGCGGAG GAGCTAAGGA AAATTTTATC TTTGCTTGAT TCCGAAATAT
1151  TTAAAGAGAT AGAAGGTTCT CTCCTTAACC TGAATAAAGT TGCGGACCTC
1201  ATTGATAAAA CGCTTGTTGA CGACCCTCCC CTGCACGTAA AAGAAGGGGG
1251  GCTTATAAAA CCCGGTGTTA ACGCATACCT TGATGAGCTT CGCTTCATAA
1301  GGGAGAATGC GGAAAAGCTC CTGAAGGAGT ATGAAAAGAA GCTGAAAAAA
1351  GAAACGGGAA TTCAGAGCTT AAAGATTGGA TACAACAAGG TTATGGGATA
1401  CTACATAGAG GTAACGAAGG CTAACGTAAA ATACGTTCCC GAACACTTCA
1451  GAAGAAGACA GACCCTTTCA ACGCGGAGA GATACACAAC CGAGGAGCTC
1501  CAGAGACTTG AGGAAAAGAT ACTTTCCGCC CAGACCCGCA TAAACGAGCT
1551  TGAGTATGAG CTTTACAGGG AGCTCAGGGA AGAGGTTGTT AAGGAGCTTG
1601  ATAAGGTAGG GAATAACGCA ACCCTCATAG GGGAGGTGGA CTACATCCAG
1651  TCCCTCGCCT GGCTTGCCCT TGAGAAGGGA TGGGTAAAGC CGGAAGTTCA
1701  CGAGGGATAT GAGCTGATAA TAGAGGAGGG AAAGCATCCC GTAATAGAGG
1751  AGTTCACGAA AAACTACGTC CCAAACGATA CGAAGCTAAC GGAAGAGGAG
1801  TTCATACACG TAATCACGGG CCCTAACATG GCGGGAAAGT CGAGCTACAT
1851  AAGACAGGTG GGCGTCCTCA CGCTCCTTGC TCATACAGGT AGCTTCCTTC
1901  CCGTAAAGAG TGCAAGGATA CCGCTGGTTG ATGCGATATT CACGAGAATA
1951  GGCTCGGGGG ACGTTCTGGC TCTGGGTGTT CAACCTTCA TGAACGAGAT
2001  GCTTGACGTG TCAAACATAC TCAACAACGC AACGAAGAGG AGCTTAATAA
2051  TACTCGACGA GGTGGGAAGG GGAACCTCAA CCTACGACGG GATAGCGATA
2101  AGCAAGGCGA TAGTGAAATA CATAAGCGAG AAGATAGGGG CGAAAACGCT
2151  ACTCGCAACC CACTACCTTG AGCTAACCGA GCTTGAGAGA AAGGTAAAGG
2201  GAGTAAAGAA CTACCACATG GAGGTTGAGG AAACGGATGA GGGAATAAGG
2251  TTCTTATACA TACTGAAGGA GGGAAGGGCG AAGGGAAGCT TCGGCATAGA
2301  CGTCGCAAAA CTCGCGGGAC TGCCCGAGGA AGTTGTAAGG GAAGCAAAAA
2351  AGATACTGAA GGAGCTTGAA GGGGAAAAAG GAAAGCAGGA AGTTCTCCCC
2401  TTCCTTGAGG AGACCTATAA AAAGTCCGTT GATGAAGAGA AGCTGAACTT
2451  TTACGAAGAG ATAATAAAGG AGATAGAGGA GATAGATATA GGGAACACGA
2501  CTCCTGTTAA AGCCCTGCTC ATCCTTGCGG AGTTAAAGGA AAGGATAAAG
2551  AGCTTTATAA AGAGGTGA
```

G + C CONTENT: 47%

FIG. 1

Apy MutS PROTEIN SEQUENCE

```
  1  MGKEEKELTP MLAQYHQFKS MYPDCLLLFR LGDFYELFYE DAVVGSKELG
 51  LVLTSRPAGK GRERIPMCGV PYHSANNYIA KLVNKGYKVA ICEQVEDPSK
101  AKGIVKRDVI RVITPGTFFE RETGGLCSLY RKGKSYLVSY LNLSVGEFIG
151  AKVKEEELID FLSKFNIREV LVKKGEKLPE KLEKVLKLHI TELEEEFFEE
201  GKEELLKDYG VPSIKAFGFQ DEDLSLSLGA VYRYAKATQK SFTPLIPKPK
251  PYVDEGYVKL DLKAVKGLEI TESIEGRKDL SLFKVVDRTL TGMGRRRLRF
301  RLLNPFRSIE RIRKVQEAVE ELINKREVLN EIRKTLEGMS DLERLVSRIS
351  SNMASPRELI HLKNSLRKAE ELRKILSLLD SEIFKEIEGS LLNLNKVADL
401  IDKTLVDDPP LHVKEGGLIK PGVNAYLDEL RFIRENAEKL LKEYEKKLKK
451  ETGIQSLKIG YNKVMGYYIE VTKANVKYVP EHFRRRQTLS NAERYTTEEL
501  QRLEEKILSA QTRINELEYE LYRELREEVV KELDKVGNNA TLIGEVDYIQ
551  SLAWLALEKG WVKPEVHEGY ELIIEEGKHP VIEEFTKNYV PNDTKLTEEE
601  FIHVITGPNM AGKSSYIRQV GVLTLLAHTG SFLPVKSARI PLVDAIFTRI
651  GSGDVLALGV STFMNEMLDV SNILNNATKR SLIILDEVGR GTSTYDGIAI
701  SKAIVKYISE KIGAKTLLAT HYLELTELER KVKGVKNYHM EVEETDEGIR
751  FLYILKEGRA KGSFGIDVAK LAGLPEEVVR EAKKILKELE GEKGKQEVLP
801  FLEETYKKSV DEEKLNFYEE IIKEIEEIDI GNTTPVKALL ILAELKERIK
851  SFIKR*
```

Tma MutS CODING SEQUENCE

```
   1  GTGAAGGTAA CTCCCCTCAT GGAACAGTAC CTGAGAATAA AAGAACAGTA
  51  CAAAGATTCC ATTCTGCTGT TTCGACTGGG AGATTTTTAC GAGGCGTTTT
 101  TCGAAGACGC AAAGATCGTT TCGAAGGTTC TGAACATAGT TCTCACAAGA
 151  AGGCAGGACG CTCCCATGGC GGGCATCCCG TACCACGCGC TGAACACCTA
 201  CCTGAAAAAG CTCGTCGAAG CGGGCTACAA GGTGGCAATC TGCGATCAAA
 251  TGAAGAACC TTCGAAGTCG AAGAAATTGA TCAGAAGGGA AGTCACGCGC
 301  GTTGTCACTC CCGGCTCCAT CGTAGAGGAT GAGTTTCTCA GCGAAACGAA
 351  CAACTACATG GCCGTTGTCT CAGAAGAGAA AGGACGGTAC TGTACGGTTT
 401  TCTGTGATGT CTCGACAGGT GAGGTCCTGG TTCATGAAAG TTCAGACGAA
 451  CAGGAAACTT TGGACCTGCT GAAGAATTAC TCCATTTCCC AGATCATCTG
 501  TCCAGAGCAC CTGAAATCTT CTTTGAAGGA ACGCTTTCCA GGTGTTTACA
 551  CAGAAACCAT AAGCGAGTGG TATTTCTCAG ATCTGGAAGA AGTGGAAAAA
 601  GCCTACAATC TGAAAGACAT TCATCATTTC GAGCTTTCGC CCCTTGCGCT
 651  GAAAGCCCTT GCGGCGCTGA TAAAGTATGT CAAGTACACG ATGATCGGGG
 701  AAGATCTGAA TCTGAAACCC CCTCTTCTCA TCTCCCAGAG AGACTACATG
 751  ATACTCGATT CCGCAACGGT GGAAAATCTT TCTTGGATTC CCGGTGACAG
 801  GGGAAAGAAT CTTTTCGATG TGCTGAACAA CACGGAAACT CCTATGGGGG
 851  CTCGTCTTGG GAAAAAGTGG ATTCTCCACC CTCTGGTCGA CAGAAAACAG
 901  ATCGAAGAAA GGCTCAAGGC TGTGGAAAGA CTGGTGAACG ACAGGGTGAG
 951  CCTGGAGGAG ATGAGGAACC TTCTTTCGAA CGTGAGGGAT GTGGAGCGGA
1001  TCGTTTCGCG GGTGGAGTAC AACAGATCCG TTCCCAGGGA CTTAGTGGCA
1051  CTCAGAGAGA CACTGGAGAT CATCCCGAAA CTGAACGAAG TTCTTTCAAC
1101  CTTCGGTGTG TTCAAGAAAC TCGCTTTCCC GGAAGGACTG GTTGATCTGC
1151  TTCGAAAAGC CATTGAAGAT GATCCGGTGG GAAGCCCCGG CGAGGGAAAA
1201  GTTATAAAGA GAGGATTCTC ATCTGAACTC GACGAATACA GGGATCTTCT
1251  GGAACATGCC GAAGAGAGGC TCAAAGAGTT CGAGGAGAAG GAGAGAGAAA
1301  GAACAGGCAT CCAAAAACTG CGGGTTGGAT ACAACCAGGT TTTTGGTTAC
1351  TACATAGAGG TGACGAAGGC GAATCTGGAT AAGATTCCCG ACGATTACGA
1401  AAGAAAACAA ACACTCGTCA ATTCTGAAAG ATTCATCACA CCCGAATTGA
1451  AGGAGTTCGA GACAAAGATA ATGGCCGCTA AAGAGAGAAT AGAAGAACTG
1501  GAAAAGGAAC TCTTCACAAG CGTGTGCGAA GAGGTGAAAA AGCACAAAGA
1551  AGTTCTCCTT GAGATCTCGG AGGATCTGGC AAAGATAGAT GCGCTTTCGA
1601  CGTTAGCATA CGACGCTATT ATGTACAACT ACACAAAACC CGTCTTTTCA
1651  GAAGACAGAC TGGAGATCAA AGGTGGAAGA CACCCGGTCG TTGAAAGGTT
1701  CACACAGAAT TTTGTTGAAA ACGATATTTA CATGGACAAC GAGAAGAGAT
1751  TTGTGGTAAT AACGGGTCCC AACATGAGCG GGAAGTCCAC TTTCATCAGA
1801  CAGGTGGGTC TCATATCCCT CATGGCGCAG ATAGGATCGT TTGTGCCGGC
1851  GCAGAAGGCG ATTCTTCCAG TGTTCGACAG GATTTTCACG CGAATGGGTG
1901  CCAGAGACGA TCTCGCTGGT GGTAGAAGTA CGTTCCTTGT CGAGATGAAC
1951  GAGATGGCGC TCATCCTTCT GAAATCAACA AATAAGAGTC TGGTTCTCCT
2001  GGACGAGGTG GGAAGAGGTA CAAGCACCCA GGACGGCGTC AGCATAGCCT
2051  GGGCAATCTC AGAGGAACTC ATAAAGAGAG GATGTAAGGT GCTGTTTGCC
2101  ACTCATTTCA CGGAACTCAC GGAACTCGAA AACACTTTC CGCAGGTTCA
2151  GAACAAAACC ATTCTGGTAA AGAAGAAGG CAAAAACGTG ATATTCACCC
2201  ACAAGGTGGT GGACGGTGTG GCAGACAGAA GTTACGGAAT AGAGGTCGCA
2251  AAGATAGCGG GTATTCCTGA CAGGGTTATA AACAGAGCCT ATGAAATTCT
2301  GGAGAGGAAT TTCAAAAACA ACACGAAGAA AAACGGAAAA TCGAACAGAT
2351  TCAGTCAGCA AATTCCTCTC TTTCCTGTTT GA
```

G + C CONTENT: 47%

FIG. 3

Tma MutS PROTEIN SEQUENCE

```
  1  VKVTPLMEQY LRIKEQYKDS ILLFRLGDFY EAFFEDAKIV SKVLNIVLTR
 51  RQDAPMAGIP YHALNTYLKK LVEAGYKVAI CDQMEEPSKS KKLIRREVTR
101  VVTPGSIVED EFLSETNNYM AVVSEEKGRY CTVFCDVSTG EVLVHESSDE
151  QETLDLLKNY SISQIICPEH LKSSLKERFP GVYTETISEW YFSDLEEVEK
201  AYNLKDIHHF ELSPLALKAL AALIKYVKYT MIGEDLNLKP PLLISQRDYM
251  ILDSATVENL SWIPGDRGKN LFDVLNNTET PMGARLGKKW ILHPLVDRKQ
301  IEERLKAVER LVNDRVSLEE MRNLLSNVRD VERIVSRVEY NRSVPRDLVA
351  LRETLEIIPK LNEVLSTFGV FKKLAFPEGL VDLLRKAIED DPVGSPGEGK
401  VIKRGFSSEL DEYRDLLEHA EERLKEFEEK ERERTGIQKL RVGYNQVFGY
451  YIEVTKANLD KIPDDYERKQ TLVNSERFIT PELKEFETKI MAAKERIEEL
501  EKELFTSVCE EVKKHKEVLL EISEDLAKID ALSTLAYDAI MYNYTKPVFS
551  EDRLEIKGGR HPVVERFTQN FVENDIYMDN EKRFVVITGP NMSGKSTFIR
601  QVGLISLMAQ IGSFVPAQKA ILPVFDRIFT RMGARDDLAG GRSTFLVEMN
651  EMALILLKST NKSLVLLDEV GRGTSTQDGV SIAWAISEEL IKRGCKVLFA
701  THFTELTELE KHFPQVQNKT ILVKEEGKNV IFTHKVVDGV ADRSYGIEVA
751  KIAGIPDRVI NRAYEILERN FKNNTKKNGK SNRFSQQIPL FPV*
```

Tth MutS Sequence

```
  1  AAGTCCACCT TCCTCCGCCG GACCGCCCTC ATCGCCCTCC TCGCCCAGAT
 51  CGGGAGCTTC GCGCCCGCCG AGGGGCTGCT GCTTCCCCTC TTTGACGGGA
101  TC
```

FIG. 5

Taq MutS Sequence

```
  1  AAGTCCACCT TTCTGCGCCA GACGGCCCTC ATCGCCCTCC TGGCCCAGGT
 51  GGGGAGCTTC GTGCCCGCCG AGGAGGCCCA TCTTCCCCTC TTTGACGGCA
101  TC
```

FIG. 6

```
        613
  Apy   KSSYIRQVG VLTLLAHTGS FLPVKSARIP LVDAI
  Taq   KSTFLRQTA LIALLAQVGS FVPAEEAHLP LFDGI
  Tth   KSTFLRRTA LIALLAQIGS FAPAEGLLLP LFDGI
  Tma   KSTFIRQVG LISLMAQIGS FVPAQKAILP VFDRI
        595
```

FIG. 7

Apy MutL Coding sequence: Upper case

```
 -60  gaattcttaa ggttctcaag ggctgttctt ttctcttttt ccttcctaat ttaatacctc
   1  ATGTTTGTCA AAATCCTGCC CCCAGAGGTA AGGAGAAAGA TTGCAGCGGG AGAGGTTATA
  61  GACGCTCCCG TTGACGTTGT AAAAGAGCTT ATAGAGAACT CCCTTGACGC TAAGGCAACG
 121  AGGATTGAGA TTGAGGTCGT AAAAGGGGGG AAAAGACTTA TCAGAGTTAA GGATAACGGG
 181  ATAGGCATTC ATCCCGAGGA TATAGAAAAG GTCGTTTTAT CGGGAGCTAC GAGCAAGATA
 241  GAGAAGGAAA CGGACCTCCT CAATGTGGAA ACCTACGGAT TCAGGGGGGA AGCCCTGTAT
 301  TCCATCTCAA GCGTAAGCAA GTTCAGGCTA AGGTCAAGGT TTTACCAGGA AAAGGAAGGA
 361  AGGGAGATAG AAGTTGAGGG GGGAACGCTA AAAAGCGTCA AAGAGTAGG AATGGAAGTT
 421  GGGACGGAAG TTGAGGTTTA CGACCTCTTT TTTAACCTCC CCGCAAGGAA GAAATTTTTA
 481  AGAAAGGAAG ACACCGAAAG GAGAAAGATA ACGGAGCTCG TAAAGGAGTA TGCCATAACA
 541  AACCCCCAGG TTGACTTTCA CCTCTTTTCC GAAGGAAAGG AAACCCTTAA CCTGAAGAAG
 601  AAGGACCTAA AAGGGAGAAT TGAGGAAATC TTTGAGTCAA TTTTTGAAGA AGAAAGCTCG
 661  GAAAGGGAAG AATAAAGGT AAGAGCCTTC ATATCAAGAA ACCAGAAAAG GGGAAAGTAT
 721  TACCTCTTCG TAAACTCAAG ACCAGTTTAC AACAAAAACT AAAAGAATA CCTAAAGAAA
 781  ACCTTCGGTT ATAAAACGAT AGTCGTGCTG TTCATTGATA TTCCCCCCTT TCTCGTTGAC
 841  TTTAACGTTC ACCCCAAAAA GAAAGAGGTA AGTTTTTAA AAGAGCGAAA GATTTACGAA
 901  CTCATAAGGG AACTCTCTTC CAGAAAACAC ACAATCCTTG AGATACCTAC ACTTAATCAG
 961  AAAACCGAAA GTTATAAACC GACATACGAG GTTATAGGTC AACTAAACGA AACCTTTATT
1021  CTCGTAAGCG ACGGGAACTT TTTATACTTC ATAGACCAGC ACCTTCTTGA TGAGAGAATA
1061  AACTACGAGA AAATGGAAA CGAAGAACTT GCCTGCAGAA TTTCCGTAAA AGCGGGGGAA
1121  AAATTAACAA ACGAAAAGAT AAAAGAACTC ATAAAGGAAT GGAAAAAGCT TGAAAACCCC
1201  CACGTATGTC CCCACGGCAG ACCTATATAC TACAAACTCC CCTTAAAGGA AGTATACGAA
1261  AAGCTCGGAA GGAGTTTTTA Aggtaaaatt ctatagaccc aatgttcagc attaagttct
```

FIG. 8

Tma MutL Coding sequence: Upper case

```
 -60            tttttctgg atgttaaaat tttcagggag atcgagtgga gaggtgttct
   1 GTTTTGAGAA TAAAAAGACT TCCCGAGAGC CTCGTCAGAA AAATCGCCGC GGGTGAGGTG
  61 ATTCACAATC CATCTTTCGT TCTGAAAGAG CTTGTAGAAA ACAGTCTGGA CGCGCAGGCC
 121 GACAGGATAG TTGTTGAGAT AGAAAACGGT GGAAAGAACA TGGTAAGAGT ATCCGACAAT
 181 GGAATCGGGA TGACCAGAGA AGAGGCACTT CTGGCAATAG AACCTTACAC GACGAGCAAG
 241 ATAGAGAGCG AGGAAGATCT GCACAGGATC AGAACTTACG GTTTCAGAGG TGAAGCGCTT
 301 GCTTCGATTG TGCAGGTCAG CAGAGCCAAG ATCGTGACAA AAACGGAAAA AGACGCACTC
 361 GCAACACAGT TGATGATTGC TGGGGGGAAA GTGGAAGAAA TCTCGGAAAC CCACAGGGAT
 421 ACCGGCACCA CCGTTGAGGT GAGAGATCTC TTCTTCAACC TACCCGTCCG GAGAAAATCT
 481 CTGAAGTCCT CTGCCATCGA GTTGAGAATG TGTCGTGAGA TGTTTGAAAG ATTCGTCCTT
 541 GTACGAAACG ACGTTGATTT TGTATTCACC TCAGATGGAA AGATAGTCCA TTCCTTTCCA
 601 AGAACACAGA ACATCTTTGA AAGAGCTCTC CTGATCCTTG AAGATCTGAG AAAAGGTTAC
 661 ATCACGTTCG AAGAGGAATT ATCCGGCCTG AGGATAAAGG GAATAGTTTC ATCCCGCGAG
 721 GTGACAAGAT CCAGCAGAAC GGGAGAGTAT TTCTACGTGA ACGGTCGTTT TGTGGTTTCC
 781 GAAGAACTCC ACGAAGTACT CATGAAAGTT TACGATCTTC AAAGAGAAG CTATCCCGTC
 841 GCGGTTCTTT TCATAGAGGT AAATCCGGAA GAACTCGACG TGAACATACA CCCTTCGAAA
 901 ATCGTGGTGA AATTTCTCAA CGAAGAAAAG GTGAAAAGA GTTTGGAAGA AACCCTCAAA
 961 AGAAATCTGG CACGGAAATG GTACAGGTCG GTTGCGTACG AAGAAATATC CTCCCGTGCG
1021 CTGAGCGTGG CAGAAGCACC ATCCCACAGA TGGTTTTTGG TCAAGGGTAA GTACGCTGTC
1081 GTTGAAGTGG AAGATGGTTT GCTCTTTGTG GATCTTCATG CTCTCCACGA ACGAACGATT
1141 TACGAAGAAA TCCTTTCGAA AAAAGCTGG GGGAAAAGAC GGGTGAAAAG GAACATAACA
1201 GTTGTGCTAT CAAGGGAAGA AAAACAAAAA CTGGAAGAAT ACGGATTCTC CTTTCAAGGA
1261 GAAGAAGGAG CTTTGAAAGT CATTGAAATC CCTGAGTTCC TCACCGAAGA CGTTGTGGAG
1321 GAATTTTTCA GGGACTTCCC AGTTGATGAA AAACTGAAGG AAAGAATAGC CCTTGCCGCT
1381 TGTAAACTTG CCACTAAATC CGGAGAATTC GACGAAGAGA TCGCATCGAA ACTGCTGGAT
1441 GTCTTTTTCA GAAGCGGTT TGAAAGATGT CCTCACGGAA GGCCGATTTC TTTCAAGATC
1501 AGCTATGAGG ACATGGACCG ATTTTTCGAG CGTTAAccca ttttcaccac gttgacgtca
1561 gcggtgaaaa ccaggccatc gaagtctatg
```

FIG. 9

```
              10        20        30        40        50        60
Apycod   MGKEEKELTPMLAQYHQFKSMYPDCLLLFRLGDFYELFYEDAVVGSKELGLVLTSRPA
              |||::||   ::|:  :|:  ||::|:||||||||:||  :|:  |::  |||:| |
Eco.Pe   MSAIENFDAHTPMMQQYLRLKAQHPEILLFYRMGDFYELFYDDAKRASQLLDISLTKRGA
              ||:|:||||:|:|:  : :|::|:||||| |::||| :|::|:| ||:|
Tmacod      VKVTPLMEQYLRIKEQYKDSILLFRLGDFYEAFFEDAKIVSKVLNIVLTRR--

70        80        90       100       110       120
Apycod   GKGRERIPMCGVPYHSANNYIAKLVNKGYKVAICEQVEDPSKAKGIVKRDVIRVITPGTF
          :  |  |:|||  |:|||::::||:|||||:|  :|||||||::||:::||  |:|:|:|::||||:
Eco.Pe   SAG-EPIPMAGIPYHAVENYLAKLVNQGESVAICEQIGDPATSKGPVERKVVRIVTPGTI
              :    ||||||||||:::||   ||||::|  :||||:||:::|::||    :  |:|:|:||||:|
Tmacod   ----QDAPMAGIPYHALNTYLKKLVEAGYKVAICDQMEEPSKSKKLIRREVTRVVTPGSI 130       140       150       160       170       180
Apycod   F------ERETGGLCSLYRKGKSYLVSYLNLSVGEF-IGAKVKEEELIDFLSKFNIREVL
              ||:::  |   :::::::|::    :  |::| |   |   |:: ::  |:: :  | : |   |:|
Eco.Pe   SDEALLQERQDNLLAAIWQDSKGFGYATLDISSGRFRLSEPADRETMAAELQRTNPAELL
              ::::|  |   :| :|:::   :::   :     : |:|:     :  |::| ::    :   |:: :  ::::
Tmacod   VEDEFLSE-TNNYMAVVSEEKGRYCTVFCDVSTGEVLVHESSDEQETLDLLKNYSISQII 190       200       210       220       230       240
Apycod   VKKGEKLPEKLEKVLKLHITELEEEFFEEGKEELLKDYGVPSIKAFGFQDEDLSL-SLGA
              ::    :|    |:    ||   ||  :::::::|   ::|::::  :||  :::  :|  :  |
Eco.Pe   YAEDFAEMSLIEGRRGLRRRPLWEFEIDTARQQLNLQFGTRDLVGFGVENAPRGLCAAGC
              ::|:: :  ||  |  :|:    ::  |::  ::|  :::  :|:  |::   :|  |  |
Tmacod   CPEHLKS-SLKERFPGVYTETISEWYF-SDLEEVEKAYNLKDIHHFEL--SPLALKALAA 250       260       270       280       290       300
Apycod   VYRYAKATQKSFTPLIPKPKPYVDEGYVKLDLKAVKGLEITESIEGRKDLSLFKVVDRTL
              : :|||:|||::   |  |:: :    :::  :  :|   :  :::|||||:::::|   :  :|  :|:|  |:
Eco.Pe   LLQYAKDTQRTTLPHIRSITMEREQDSIIMDAATRRNLEITQNLAGGAENTLASVLDCTV
              |::|:| |   :: ::::  : :::| :|:|:||  ||:   ::|: :::| :||: |
Tmacod   LIKYVKYTMIGEDLNLKPPLLISQRDYMILDSATVENLS---WIPGDRGKNLFDVLNNTE 310       320       330       340       350
Apycod   TGMGRRRLRFRLLNPFRSIERIRKVQEAVEELINKREVLNEIRKTLEGMSDLERLVSRIS
              | ||:|:|: :|  | ||:: : : |::::::|     ::     ::::  :|  ::|||:::|::
Eco.Pe   TPMGSRMLKRWLHMPVRDTRVLLERQQTIGAL---QDFTAGLQPVLRQVGDLERILARLA
              ||||:|:  |:|: |:| : |||  || :|::| :    |   :|: ||:::  |:|||:|::|::
Tmacod   TPMGARLGKKWILHPLVDRKQIEERLKAVERLVNDRVSLEEMRNLLSNVRDVERIVSRVE 360       370       380       390       400       410
Apycod   SNMASPRELIHLKNSLRKAEELRKILSLLDSEIFKEIEGSLLNLNKVADLIDKTLVDDPP
              : |:||:| :::::::::    |||   |: :||:   :::   :::   :::::  ||:::::::|:||
Eco.Pe   LRTARPRDLARMRHAFQQLPELRAQLETVDSAPVQALREKMGEFAELRDLLERAIIDTPP
              :  :  ||||: :|::::  :|:|:::  |:|   ::  |||  :||:: ::| |||  :||  |:|
Tmacod   YNRSVPRDLVALRETLEIIPKLNEVLSTF------GVFKKLAFPEGLVDLLRKAIEDDPV

FIG. 10A
```

```
        420        430        440        450        460        470
Apycod  LHVKEGGLIKPGVNAYLDELRFIRENAEKLLKEYEKKLKKETGIQSLKIGYNKVMGYYIE
        :|::||:| :| |: ||| | : ::|:: |:  |  | :: ||:::||:|:| | ||||:
Eco.Pe  VLVRDGGVIASGYNEELDEWRALADGATDYLERLEVRERERTGLDTLKVGFNAVHGYYIQ
        :| || :|:::||||:|:| : |:: |: :| :|||||||:::|||:|:| ||||:
Tmacod  GSPGEGKVIKRGFSSELDEYRDLLEHAEERLKEFEEKERERTGIQKLRVGYNQVFGYYIE 480        490        500        510        520        530
Apycod  VTKANVKYVPEHFRRRQTLSNAERYTTEELQRLEEKILSAQTRINELEYELYRELREEVV
        ::::: : :| :::|||||:||||:: || |:|:|::::: :|| :|| || :: ::
Eco.Pe  ISRGQSHLAPINYMRRQTLKNAERYIIPELKEYEDKVLTSKGKALALEKQLYEELFDLLL
        ::::: : | :| |:||| |:||:|:|||||:|:|:::|:: :|||:|::::  : :
Tmacod  VTKANLDKIPDDYERKQTLVNSERFITPELKEFETKIMAAKERIEELEKELFTSVCEEVK 540        550        560        570        580        590
Apycod  KELDKVGNNATLIGEVDYIQSLAWLALEKGWVKPEVHEGYELIIEEGKHPVIEE-FTKNY
        :|: : ::|: ::|:| : :|| |  | : ::: |:  : :: |:||:|||:|: ::: :
Eco.Pe  PHLEALQQSASALAELDVLVNLAERAYTLNYTCPTFIDKPGIRITEGRHPVVEQVLNEPF
        | |:| : :::||::|:| :|| | ||| |: ::: : |:::|||||||: ::: |
Tmacod  KHKEVLLEISEDLAKIDALSTLAYDAIMYNYTKPVFSEDR-LEIKGGRHPVVER-FTQNF 600        610        620        630        640        650
Apycod  VPNDTKLTEEEFIHVITGPNMAGKSSYIRQVGVLTLLAHTGSFLPVKSARIPLVDAIFTR
        ::| :|: : : :|||||||:|||:|:||:::::|:::||::|:::: | :| ||||
Eco.Pe  IANPLNLSPQRRMLIITGPNMGGKSTYMRQTALIALMAYIGSYVPAQKVEIGPIDRIFTR
        ::| : : :: ::|:||||||||:||||:||||::|:||| ||| |||||| : |||||| 
Tmacod  VENDIYMDNEKRFVVITGPNMSGKSTFIRQVGLISLMAQIGSFVPAQKAILPVFDRIFTR 660        670        680        690        700        710
Apycod  IGSGDVLALGVSTFMNEMLDVSNILNNATKRSLIILDEVGRGTSTYDGIAISKAIVKYIS
        :|::| || | |||| || :::|||:|||: ||:::||:||||||||||||:::: |  :: ::
Eco.Pe  VGAADDLASGRSTFMVEMTETANILHNATEYSLVLMDEIGRGTSTYDGLSLAWACAENLA
        :||  ||||:|||||:|||:| | || ::|: ||||:||:|||||| ||:|:|||  :|:|
Tmacod  KGARDDLAGGRSTFLVEMNEMALILLKSTNKSLVLLDEVGRGTSTQDGVSIAWAISEELI 720        730        740        750        760        770
Apycod  EKIGAKTLLATHYLELTELERKVKGVKNYHMEVEETDEGIRFLYILKEGRAKGSFGIDVA
        :|| | ||:|||||:|||:| |::|| | |:::  | :::| |:: :::| |: |:|::||
Eco.Pe  NKIKALTLFATHYFELTQLPEKMEGVANVHLDALEHGDTIAFMHSVQDGAASKSYGLAVA
        ::        :||||:| |||:| ::: |:| : :|::: | |: ||:::|||::||
Tmacod  KR-GCKVLFATHFTELTELEKHFPQVQNKTILVKEEGKNVIFTHKVVDGVADRSYGIEVA 780        790        800        810        820        830
Apycod  KLAGLPEEVVREAKKIL-KELEGEKGKQEVLPFLEETYKK-SVDEEKLNFYEEIIKEIEE
        |||:|:||:: |:: | :|||: : :::: :  ::  : || ||:    : :::: |:
Eco.Pe  ALAGVPKEVIKRARQKL-RELESISPNAAATQVDGTQMSLLSVPEET----SPAVEALEN
        :||:|: ||:|| : |  |:::: : ::: ::  : |::|::|
Tmacod  KIAGIPDRVINRAYEILERNFKNNTKKNGKSNRFSQQIPLFPV*
        840        850
Apy.Pe  IDIGNTTPVKALLILAELKERIKSFIKR*
        :| ::  || : ||  : ||: :
Eco.Se  LDPDSLTPRQALEWIYRLKSLV*
```

FIG. 10B

```
            1                                                         50
Apy   .MFVKILPPE  VRRKIAAGEV  IDAPVDVVKE  LIENSLDAKA  TRIEIEVVKG
Tma   MLRIKRLPES  LVRKIAAGEV  IHNPSFVLKE  LVEKSLDAQA  DRIVVEIENG
Spn   MSHIIELPEM  LANQIAAGEV  IERPASVCKE  LVENAIDAGS  SQIIIEIEEA
Eco   .MPIQVLPPQ  LANQIAAGEV  VERPASVVKE  LVENSLDAGA  TRIDIDIERG 51                                                        100
Apy   GKRLIRVKDN  GIGIHPEDIE  KVVLSGATSK  IEKETDLLNV  ETYGFRGEAL
Tma   GKNMVRVSDN  GIGMTREEAL  LAIEPYTTSK  IESEEDLHRI  RTYGFRGEAL
Spn   GLKKVQITDN  GHGIAHDEVE  LALRRHATSK  IKNQADLFRI  RTLGFRGEAL
Eco   GAKLIRIRDN  GCGIKKDELA  LALARHATSK  IASLDDLEAI  ISLGFRGEAL 101                                                       150
Apy   YSISSVSKFR  LRSRFYQEKE  GREIEVEGGT  LK.SVRRVGM  EVGTEVEVYD
Tma   ASIVQVSRAK  IVTKTEKDAL  ATQLMIAGGK  VE.EISETHR  DTGTTVEVRD
Spn   PSIASVSVLT  LLTAVDGASH  GTKLVARGGE  VE.EVIPATS  PVGTKVCVED
Eco   ASISSVSRLT  LTSRTAEQQE  AWQAYAEGRD  MNVTVKPAAH  PVGTTLEVLD 151                                                       200
Apy   LFFNLPARKK  FLRKEDTERR  KITELVKEYA  ITNPQVDFHL  FSEGKETLNL
Tma   LFFNLPVRRK  SLKSSAIELR  MCREMFERFV  LVRNDVDFVF  TSDGKIVHSF
Spn   LFFNTPARLK  YMKSQQAELS  HIIDIVNRLG  LAHPEISFSL  ISDGKEMTRT
Eco   LFYNTPARRK  FLRTEKTEFN  HIDEIIRRIA  LARFDVTINL  SHNGKIVRQY 201                                                       250
Apy   ...KKKDLKG  RIEEIFESI.  .....FEEES  SEREGIKVRA  FISRNQ....
Tma   ..PRTQNIFE  RALLILEDLR  KGYITFEEEL  S...GLRIKG  IVSSREVTRS
Spn   ..AGTGQLRQ  AIAGIY.GLV  SAKKMIEIEN  SD.LDFEISG  FVSLPELTRA
Eco   RAVPEGGQKE  RRLGAICGTA  FLEQALAIE.  WQHGDLTLRG  WVADPNHTTP 251                                                       300
Apy   KRGKY.YLFV  NSRPVYNKNL  KEYLKKTFG.  .YK....TIV  VLFIDIPPFL
Tma   SRTGE.YFYV  NGRFVVSEEL  HEVLMKVYD.  .LPKRSYPVA  VLFIEVNPEE
Spn   NRNYI.SLFI  NGRYIKNFLL  NRAILDGFGS  KLMVGRFPLA  VIHIHIDPYL
Eco   ALAEIQYCYV  NGRMMRDRLI  NHAIRQACED  KLGADQQPAF  VLYLEIDPHQ 301                                                       350
Apy   VDFNVHPKKK  EVKFLKERKI  .....YELIR  ELSSRKHTIL  EIPTLNQKTE
Tma   LDVNIHPSKI  VVKFLNEEKV  KKSLEETLKR  NLARKWYRSV  AYEEISSRAL
Spn   ADVNVHPTKQ  EVRISKEKEL  MTLVSEAIAN  SLKEQTLIPD  ALENLAKSTV
Eco   VDVNVHPAKH  EVRFHQSRLV  HDFIYQGVLS  VLQQQLETPL  PLDDEPQPAP
```

FIG. 11A

```
            351                                                          400
Apy    SY.K......  ..........  ..........  ..........  ..........
Tma    SVAE......  ..........  ..........  ..........  ..........
Spn    RNREKVEQTI  LPLKENTLYY  EKTEPSRPSQ  TEVADYQVEL  TDEGQDLTLF
Eco    RSIPENRVAA  GRNHFAEPAA  REPVAPRYTP  APASGSRPAA  P.........

401                                                          450
Apy    ..........  ..........  ..........  ..........  ..........
Tma    ..........  ..........  ..........  ..........  ..........
Spn    AKETLDRLTK  PAKLHFAERK  PANYDQLDHP  ELDLASIDKA  YDKLEREEAS
Eco    ........WP  NAQPGYQKQQ  GEVYRQLLQT  PAPMQKLKAP  EPQEPALAAN 451                                                          500
Apy    ..PTYEVIGQ  LNETFILVSD  GNFLYFIDQH  LLDERINY..  ..........
Tma    ..APSHRWFL  VKGKYAVVEV  EDGLLFVDLH  ALHERTIYEE  ILSKKSWGKR
Spn    SFPELEFFGQ  MHGTYLFAQG  RDGLYIIDQH  AAQERVKYEE  YRESIGNVDQ
Eco    SQSFGRVLTI  VHSDCALLER  DGNISLLSLP  VAERWLRQAQ  LTPGEAPV..

501                                                          550
Apy    ..........  ..........  ...EKNGNEE  LACRISV.KA  G........E
Tma    RVKRNITVVL  S.........  .REEKQKLEE  YGFSFQG.EE  GALKVIEIPE
Spn    SQQQLLVPYI  FEFPADDALR  LKERMPLLEE  VGVFLAEYGE  NQFILREHPI
Eco    CAQPLLIPLR  LKVSAEEKSA  LEKAQSALAE  LGIDFQS.DA  QHVTIRAVPL 551                                                          600
Apy    KLTNEKIKE.  .........L  IKEW...KKL  ENP.......  ..........
Tma    FLTEDVVEE.  .........F  FRDFPVDEKL  KERIALAACK  LATKSGEFDE
Spn    WMAEEEIESG  IYEMCDMLLL  TKEVSIKKYR  AELAIMMSCK  RSIKANHRID
Eco    PLRQQNLQIL  IPELIG..YL  AKQSVFEP..  GNIAQWIARN  LMSEHAQWSM 601                                                          650
Apy    ..........  .....HV..C  PHG...RPIY  YKLPLKEVYE  KLGRSF*...
Tma    EIASKLLDVF  FKKRFER..C  PHG...RPIS  FKIS....YE  DMDRFFER*.
Spn    DHSARQLLYQ  LSQCDNPYNC  PHG...RPVL  VHFTKSDM.E  KMFRRIQENH
Eco    AQAITLLADV  ERLCPQLVKT  PPGGLLQSVD  LHPAIKALKD  E*........

651
Apy    ..........
Tma    ..........
Spn    TSLRELGKY*
Eco    ..........
```

FIG. 11B

Tma MutS PROTEIN INITIATION & TERMINATION

INITIATION:

End of orf:
R  E  F  Y  E  R  L  G  Y  R  A  E  G  E  I  F  F  Y  E  R  T  F  H  T  *
                                                                        =

Initiation of Tma MutS:
*  E  S  S  T  R  D  S  V  T  G  Q  K  E  R  S  S  T  N  E  H  S  T  R  E  D  G  E  G  G  E  T  V  K  V  T
=                         =                                                                      =     =  =

5' Sequence:
TGAGAGAGTTCTACGAGAGACTCGGTTACAGGGCAGAAGGAGAGATCTTCTACGAACGAACATTCCACACGTGAGGATGGTGAAGGTGGTGAAACGGTGAAGGTAAC 3' end of 16S ribosomal RNA:                                                  ucuUUCCuCCACU

TERMINATION:

Antisense orf:                    *  D  A  F  E  E  R  E  Q  K  I  S  K  I  L  E  V  Y  N  D  N  R  F
                                  =

Termination of Tma MutS:
K  N  N  T  K  K  N  G  K  S  N  R  F  S  Q  Q  I  P  L  F  P  V  *
                                                                  =

3' Sequence:
AAAACAACACGAAGAAAAACGAAAATCGAACAGATTCAGTCAGCAGAAATTCCTCTCTTCCCTGTTTGATGCTCTTATCAGTTCAAGTAATTGTCGTTTCTGAA Antisense orf identification:

Sma.dod  KLRQVRKLIDDSGRDIRLEVDGGVKVDNIAEIAAAGADMFVAGSAIFGQPDYRK*
         |:::|||:::::: ||||: :|||||:|||||:||||:||||||||||||||||*
Anti.tma KIRNLRKMVKELGLETEIMVDGGVNEENASILVKNGATILVMGYGIFRNDNYVELIKSIKQEREEFAD*
         ::::|||::::: ||| ::::||||:|||:|||||:||||:|||||::|:|:||
Aeu.epi  ARARIDRQVDAGGRPVWLEIDGGVKADNIAAIARAGADTFVAGSAVFGAPDADGGYSSILYRLREAATVT*

D-ribulose-5-phosphate 3-epimerase - Alcaligenes eutrophus; dod - Serratia marcescens

FIG. 12

```
  1  GAATTCGATC ACCTGCAAGA AGTCATCAAG CGCCTGGCCC TGGCCCGTTT
 51  CGACGTGGCC TTTCACCTGC GCCACAATGG CAAGACCATC CTCAGCCTGC
101  ACGAAGCCAA CGACGACGCC GCCCGTGCTC GGCGGGTGGC GGCGGTGTGT
151  GGCAGCGGGT TCCTGGAGCA GGCGCTGCCG ATTGAGATCG AGCGCAATGG
201  CTTGAGGTTG TGGGGCTGGG TCGGGTTGCC GACGTTCTCC CGCAGCCAGG
251  CCGATTTGCA GTATTTCTTT GTGAACGGCC GGGCGGTCCG CGACAAACTG
301  GTGGCCCATG CGGTGCGCCA GGCTTATCGC GATGTGCTGT TCAACGGGCG
351  ACACCCGACT TTTGTGCTGT TCTTTGAGGT TGACCCTTCG GTGGTC
```

FIG. 13

```
              151                                                        200
E. coli       LFYNTPARRK FLRTEKTEFN HIDEIIRRIA LARFDVTINL SHNGKIVRQY
T. ther       .......... .......EFD HLQEVIKRLA LARFDVAFHL RHNGKTILSL
S. pneu       LFFNTPARLK YMKSQQAELS HIIDIVNRLG LAHPEISFSL ISDGK...EM 201                                                        250
E. coli       RAVPEGGQKE RRLGAICGTA FLEQALAIEW QHGDLTLRGW VADPNHTTPA
T. ther       HEANDDAARA RRVAAVCGSG FLEQALPIEI ERNGLRLWGW VGLPTF.SRS
S. pneu       TRTAGTGQLR QAIAGIYGLV SAKKMIEIEN SDLDFEISGF VSLPEL.TRA 251                                                        300
E. coli       LAEIQYCYVN GRMMRDRLIN HAIRQACEDK LGADQQPAFV LYLEIDPHQV
T. ther       QADLQYFFVN GRAVRDKLVA HAVRQAYRDV LFNGRHPTFV LFFEVDPSVV
S. pneu       NRNYISLFIN GRYIKNFLLN RAILDGFGSK LMVGRFPLAV IHIHIDPYLA
```

FIG. 14

SEQUENCE LISTING

<160> NUMBER OF SEQ ID NOS: 48

<210> SEQ ID NO 1
<211> LENGTH: 2568
<212> TYPE: DNA
<213> ORGANISM: Aquifex pyrophilus
<220> FEATURE:
<221> NAME/KEY: CDS
<222> LOCATION: (1)...(2565)

<400> SEQUENCE: 1

```
atg gga aaa gag gag aaa gag ctc acc ccc atg ctc gcc cag tat cac      48
Met Gly Lys Glu Glu Lys Glu Leu Thr Pro Met Leu Ala Gln Tyr His
 1               5                  10                  15 cag ttc aag agc atg tat ccc gac tgc ctt ctt tta ttc agg ctc ggg      96
Gln Phe Lys Ser Met Tyr Pro Asp Cys Leu Leu Leu Phe Arg Leu Gly
                20                  25                  30 gac ttt tac gag ctc ttt tac gag gac gcg gtc gtc ggt tct aaa gag     144
Asp Phe Tyr Glu Leu Phe Tyr Glu Asp Ala Val Val Gly Ser Lys Glu
            35                  40                  45 ctc ggt cta gtt cta act tca aga ccc gcg gga aag gga agg gaa agg     192
Leu Gly Leu Val Leu Thr Ser Arg Pro Ala Gly Lys Gly Arg Glu Arg
        50                  55                  60 att ccc atg tgc ggt gtt ccc tac cat tct gca aac aac tat ata gca     240
Ile Pro Met Cys Gly Val Pro Tyr His Ser Ala Asn Asn Tyr Ile Ala
    65                  70                  75                  80 aag ctc gtt aat aag gga tac aag gta gca ata tgc gag cag gtt gag     288
Lys Leu Val Asn Lys Gly Tyr Lys Val Ala Ile Cys Glu Gln Val Glu
                85                  90                  95 gac ccc tca aag gca aag gga ata gta aag agg gac gta ata aga gtt     336
Asp Pro Ser Lys Ala Lys Gly Ile Val Lys Arg Asp Val Ile Arg Val
               100                 105                 110 ata aca cct ggg acc ttt ttt gag agg gaa acg gga ggg ctt tgc tcc     384
```

-continued

| | | | | | | | | | | | | | | |
|---|---|---|---|---|---|---|---|---|---|---|---|---|---|---|
| Ile | Thr | Pro | Gly | Thr | Phe | Phe | Glu | Arg | Glu | Thr | Gly | Gly | Leu | Cys | Ser |
| | | 115 | | | | | 120 | | | | 125 | | | | |

| ctt | tac | agg | aag | gga | aag | agc | tat | ctc | gtt | tct | tat | ctt | aac | ctc | tcg | 432 |
|---|---|---|---|---|---|---|---|---|---|---|---|---|---|---|---|---|
| Leu | Tyr | Arg | Lys | Gly | Lys | Ser | Tyr | Leu | Val | Ser | Tyr | Leu | Asn | Leu | Ser | |
| | 130 | | | | 135 | | | | 140 | | | | | | | |

| gta | ggt | gag | ttc | ata | ggt | gca | aag | gta | aag | gag | gaa | gag | ctc | ata | gac | 480 |
|---|---|---|---|---|---|---|---|---|---|---|---|---|---|---|---|---|
| Val | Gly | Glu | Phe | Ile | Gly | Ala | Lys | Val | Lys | Glu | Glu | Glu | Leu | Ile | Asp | |
| 145 | | | | 150 | | | | 155 | | | | 160 | | | | |

| ttc | ctc | tca | aag | ttc | aac | ata | agg | gag | gtt | ctt | gta | aag | aag | gga | gaa | 528 |
|---|---|---|---|---|---|---|---|---|---|---|---|---|---|---|---|---|
| Phe | Leu | Ser | Lys | Phe | Asn | Ile | Arg | Glu | Val | Leu | Val | Lys | Lys | Gly | Glu | |
| | | | 165 | | | | 170 | | | | 175 | | | | | |

| aag | ctc | ccc | gaa | aag | ctt | gag | aag | gtt | cta | aag | ctc | cac | ata | acg | gag | 576 |
|---|---|---|---|---|---|---|---|---|---|---|---|---|---|---|---|---|
| Lys | Leu | Pro | Glu | Lys | Leu | Glu | Lys | Val | Leu | Lys | Leu | His | Ile | Thr | Glu | |
| | | 180 | | | | 185 | | | | 190 | | | | | | |

| ctt | gaa | gag | gag | ttc | ttt | gag | gag | gga | aag | gag | gag | ctt | ctt | aag | gat | 624 |
|---|---|---|---|---|---|---|---|---|---|---|---|---|---|---|---|---|
| Leu | Glu | Glu | Glu | Phe | Phe | Glu | Glu | Gly | Lys | Glu | Glu | Leu | Leu | Lys | Asp | |
| | 195 | | | | 200 | | | | 205 | | | | | | | |

| tac | gga | gtt | ccg | tcg | ata | aaa | gcc | ttc | ggc | ttt | cag | gat | gag | gat | tta | 672 |
|---|---|---|---|---|---|---|---|---|---|---|---|---|---|---|---|---|
| Tyr | Gly | Val | Pro | Ser | Ile | Lys | Ala | Phe | Gly | Phe | Gln | Asp | Glu | Asp | Leu | |
| 210 | | | | 215 | | | | 220 | | | | | | | | |

| tcc | ctt | tcc | ctc | ggg | gct | gtt | tac | agg | tat | gca | aag | gcg | aca | cag | aaa | 720 |
|---|---|---|---|---|---|---|---|---|---|---|---|---|---|---|---|---|
| Ser | Leu | Ser | Leu | Gly | Ala | Val | Tyr | Arg | Tyr | Ala | Lys | Ala | Thr | Gln | Lys | |
| 225 | | | | 230 | | | | 235 | | | | 240 | | | | |

| tct | ttt | acc | cct | ctc | att | cca | aag | ccc | aaa | cct | tac | gtt | gac | gag | gga | 768 |
|---|---|---|---|---|---|---|---|---|---|---|---|---|---|---|---|---|
| Ser | Phe | Thr | Pro | Leu | Ile | Pro | Lys | Pro | Lys | Pro | Tyr | Val | Asp | Glu | Gly | |
| | | | 245 | | | | 250 | | | | 255 | | | | | |

| tac | gta | aag | ctt | gac | ctc | aag | gca | gtc | aaa | ggt | ctt | gag | att | acc | gaa | 816 |
|---|---|---|---|---|---|---|---|---|---|---|---|---|---|---|---|---|
| Tyr | Val | Lys | Leu | Asp | Leu | Lys | Ala | Val | Lys | Gly | Leu | Glu | Ile | Thr | Glu | |
| | | 260 | | | | 265 | | | | 270 | | | | | | |

| agc | ata | gaa | gga | aga | aag | gat | tta | tcc | ctg | ttt | aag | gtc | gtt | gac | aga | 864 |
|---|---|---|---|---|---|---|---|---|---|---|---|---|---|---|---|---|
| Ser | Ile | Glu | Gly | Arg | Lys | Asp | Leu | Ser | Leu | Phe | Lys | Val | Val | Asp | Arg | |
| | 275 | | | | 280 | | | | 285 | | | | | | | |

| acc | ctc | acg | ggt | atg | ggg | aga | agg | agg | ctg | agg | ttc | agg | ctt | cta | aac | 912 |
|---|---|---|---|---|---|---|---|---|---|---|---|---|---|---|---|---|
| Thr | Leu | Thr | Gly | Met | Gly | Arg | Arg | Arg | Leu | Arg | Phe | Arg | Leu | Leu | Asn | |
| 290 | | | | 295 | | | | 300 | | | | | | | | |

| ccc | ttc | agg | agc | ata | gag | aga | ata | agg | aag | gtt | cag | gaa | gca | gtt | gag | 960 |
|---|---|---|---|---|---|---|---|---|---|---|---|---|---|---|---|---|
| Pro | Phe | Arg | Ser | Ile | Glu | Arg | Ile | Arg | Lys | Val | Gln | Glu | Ala | Val | Glu | |
| 305 | | | | 310 | | | | 315 | | | | 320 | | | | |

| gag | cta | ata | aac | aag | agg | gag | gtt | ctg | aac | gag | ata | agg | aaa | acc | ctt | 1008 |
|---|---|---|---|---|---|---|---|---|---|---|---|---|---|---|---|---|
| Glu | Leu | Ile | Asn | Lys | Arg | Glu | Val | Leu | Asn | Glu | Ile | Arg | Lys | Thr | Leu | |
| | | | 325 | | | | 330 | | | | 335 | | | | | |

| gag | ggt | atg | tcc | gac | ctt | gag | aga | ctc | gta | tcc | agg | ata | agc | tca | aac | 1056 |
|---|---|---|---|---|---|---|---|---|---|---|---|---|---|---|---|---|
| Glu | Gly | Met | Ser | Asp | Leu | Glu | Arg | Leu | Val | Ser | Arg | Ile | Ser | Ser | Asn | |
| | | 340 | | | | 345 | | | | 350 | | | | | | |

| atg | gca | agc | cca | aga | gaa | ctt | ata | cac | ctc | aaa | aac | tcc | cta | agg | aag | 1104 |
|---|---|---|---|---|---|---|---|---|---|---|---|---|---|---|---|---|
| Met | Ala | Ser | Pro | Arg | Glu | Leu | Ile | His | Leu | Lys | Asn | Ser | Leu | Arg | Lys | |
| | 355 | | | | 360 | | | | 365 | | | | | | | |

| gcg | gag | gag | cta | agg | aaa | att | tta | tct | ttg | ctt | gat | tcc | gaa | ata | ttt | 1152 |
|---|---|---|---|---|---|---|---|---|---|---|---|---|---|---|---|---|
| Ala | Glu | Glu | Leu | Arg | Lys | Ile | Leu | Ser | Leu | Leu | Asp | Ser | Glu | Ile | Phe | |
| 370 | | | | 375 | | | | 380 | | | | | | | | |

| aaa | gag | ata | gaa | ggt | tct | ctc | ctt | aac | ctg | aat | aaa | gtt | gcg | gac | ctc | 1200 |
|---|---|---|---|---|---|---|---|---|---|---|---|---|---|---|---|---|
| Lys | Glu | Ile | Glu | Gly | Ser | Leu | Leu | Asn | Leu | Asn | Lys | Val | Ala | Asp | Leu | |
| 385 | | | | 390 | | | | 395 | | | | 400 | | | | |

| att | gat | aaa | acg | ctt | gtt | gac | gac | cct | ccc | ctg | cac | gta | aaa | gaa | ggg | 1248 |
|---|---|---|---|---|---|---|---|---|---|---|---|---|---|---|---|---|
| Ile | Asp | Lys | Thr | Leu | Val | Asp | Asp | Pro | Pro | Leu | His | Val | Lys | Glu | Gly | |
| | | | 405 | | | | 410 | | | | 415 | | | | | |

| ggg | ctt | ata | aaa | ccc | ggt | gtt | aac | gca | tac | ctt | gat | gag | ctt | cgc | ttc | 1296 |
|---|---|---|---|---|---|---|---|---|---|---|---|---|---|---|---|---|
| Gly | Leu | Ile | Lys | Pro | Gly | Val | Asn | Ala | Tyr | Leu | Asp | Glu | Leu | Arg | Phe | |
| | | 420 | | | | 425 | | | | 430 | | | | | | |

```
                                                    -continued ata agg gag aat gcg gaa aag ctc ctg aag gag tat gaa aag aag ctg      1344
Ile Arg Glu Asn Ala Glu Lys Leu Leu Lys Glu Tyr Glu Lys Lys Leu
            435                 440                 445 aaa aaa gaa acg gga att cag agc tta aag att gga tac aac aag gtt      1392
Lys Lys Glu Thr Gly Ile Gln Ser Leu Lys Ile Gly Tyr Asn Lys Val
    450                 455                 460 atg gga tac tac ata gag gta acg aag gct aac gta aaa tac gtt ccc      1440
Met Gly Tyr Tyr Ile Glu Val Thr Lys Ala Asn Val Lys Tyr Val Pro
465                 470                 475                 480 gaa cac ttc aga aga aga cag acc ctt tca aac gcg gag aga tac aca      1488
Glu His Phe Arg Arg Arg Gln Thr Leu Ser Asn Ala Glu Arg Tyr Thr
                485                 490                 495 acc gag gag ctc cag aga ctt gag gaa aag ata ctt tcc gcc cag acc      1536
Thr Glu Glu Leu Gln Arg Leu Glu Glu Lys Ile Leu Ser Ala Gln Thr
            500                 505                 510 cgc ata aac gag ctt gag tat gag ctt tac agg gag ctc agg gaa gag      1584
Arg Ile Asn Glu Leu Glu Tyr Glu Leu Tyr Arg Glu Leu Arg Glu Glu
        515                 520                 525 gtt gtt aag gag ctt gat aag gta ggg aat aac gca acc ctc ata ggg      1632
Val Val Lys Glu Leu Asp Lys Val Gly Asn Asn Ala Thr Leu Ile Gly
    530                 535                 540 gag gtg gac tac atc cag tcc ctc gcc tgg ctt gcc ctt gag aag gga      1680
Glu Val Asp Tyr Ile Gln Ser Leu Ala Trp Leu Ala Leu Glu Lys Gly
545                 550                 555                 560 tgg gta aag ccg gaa gtt cac gag gga tat gag ctg ata ata gag gag      1728
Trp Val Lys Pro Glu Val His Glu Gly Tyr Glu Leu Ile Ile Glu Glu
                565                 570                 575 gga aag cat ccc gta ata gag gag ttc acg aaa aac tac gtc cca aac      1776
Gly Lys His Pro Val Ile Glu Glu Phe Thr Lys Asn Tyr Val Pro Asn
            580                 585                 590 gat acg aag cta acg gaa gag gag ttc ata cac gta atc acg ggc cct      1824
Asp Thr Lys Leu Thr Glu Glu Glu Phe Ile His Val Ile Thr Gly Pro
        595                 600                 605 aac atg gcg gga aag tcg agc tac ata aga cag gtg ggc gtc ctc acg      1872
Asn Met Ala Gly Lys Ser Ser Tyr Ile Arg Gln Val Gly Val Leu Thr
    610                 615                 620 ctc ctt gct cat aca ggt agc ttc ctt ccc gta aag agt gca agg ata      1920
Leu Leu Ala His Thr Gly Ser Phe Leu Pro Val Lys Ser Ala Arg Ile
625                 630                 635                 640 ccg ctg gtt gat gcg ata ttc acg aga ata ggc tcg ggg gac gtt ctg      1968
Pro Leu Val Asp Ala Ile Phe Thr Arg Ile Gly Ser Gly Asp Val Leu
                645                 650                 655 gct ctg ggt gtt tca acc ttc atg aac gag atg ctt gac gtg tca aac      2016
Ala Leu Gly Val Ser Thr Phe Met Asn Glu Met Leu Asp Val Ser Asn
            660                 665                 670 ata ctc aac aac gca acg aag agg agc tta ata ata ctc gac gag gtg      2064
Ile Leu Asn Asn Ala Thr Lys Arg Ser Leu Ile Ile Leu Asp Glu Val
        675                 680                 685 gga agg gga acc tca acc tac gac ggg ata gcg ata agc aag gcg ata      2112
Gly Arg Gly Thr Ser Thr Tyr Asp Gly Ile Ala Ile Ser Lys Ala Ile
    690                 695                 700 gtg aaa tac ata agc gag aag ata ggg gcg aaa acg cta ctc gca acc      2160
Val Lys Tyr Ile Ser Glu Lys Ile Gly Ala Lys Thr Leu Leu Ala Thr
705                 710                 715                 720 cac tac ctt gag cta acc gag ctt gag aga aag gta aag gga gta aag      2208
His Tyr Leu Glu Leu Thr Glu Leu Glu Arg Lys Val Lys Gly Val Lys
                725                 730                 735 aac tac cac atg gag gtt gag gaa acg gat gag gga ata agg ttc tta      2256
Asn Tyr His Met Glu Val Glu Glu Thr Asp Glu Gly Ile Arg Phe Leu
            740                 745                 750
```

```
tac ata ctg aag gag gga agg gcg aag gga agc ttc ggc ata gac gtc    2304
Tyr Ile Leu Lys Glu Gly Arg Ala Lys Gly Ser Phe Gly Ile Asp Val
        755                 760                 765 gca aaa ctc gcg gga ctg ccc gag gaa gtt gta agg gaa gca aaa aag    2352
Ala Lys Leu Ala Gly Leu Pro Glu Glu Val Val Arg Glu Ala Lys Lys
    770                 775                 780 ata ctg aag gag ctt gaa ggg gaa aaa gga aag cag gaa gtt ctc ccc    2400
Ile Leu Lys Glu Leu Glu Gly Glu Lys Gly Lys Gln Glu Val Leu Pro
785                 790                 795                 800 ttc ctt gag gag acc tat aaa aag tcc gtt gat gaa gag aag ctg aac    2448
Phe Leu Glu Glu Thr Tyr Lys Lys Ser Val Asp Glu Glu Lys Leu Asn
                805                 810                 815 ttt tac gaa gag ata ata aag gag ata gag gag ata gat ata ggg aac    2496
Phe Tyr Glu Glu Ile Ile Lys Glu Ile Glu Glu Ile Asp Ile Gly Asn
            820                 825                 830 acg act cct gtt aaa gcc ctg ctc atc ctt gcg gag tta aag gaa agg    2544
Thr Thr Pro Val Lys Ala Leu Leu Ile Leu Ala Glu Leu Lys Glu Arg
        835                 840                 845 ata aag agc ttt ata aag agg tga                                    2568
Ile Lys Ser Phe Ile Lys Arg
    850                 855

<210> SEQ ID NO 2
<211> LENGTH: 855
<212> TYPE: PRT
<213> ORGANISM: Aquifex pyrophilus

<400> SEQUENCE: 2

Met Gly Lys Glu Glu Lys Glu Leu Thr Pro Met Leu Ala Gln Tyr His
1               5                   10                  15

Gln Phe Lys Ser Met Tyr Pro Asp Cys Leu Leu Leu Phe Arg Leu Gly
            20                  25                  30

Asp Phe Tyr Glu Leu Phe Tyr Glu Asp Ala Val Val Gly Ser Lys Glu
        35                  40                  45

Leu Gly Leu Val Leu Thr Ser Arg Pro Ala Gly Lys Gly Arg Glu Arg
    50                  55                  60

Ile Pro Met Cys Gly Val Pro Tyr His Ser Ala Asn Asn Tyr Ile Ala
65                  70                  75                  80

Lys Leu Val Asn Lys Gly Tyr Lys Val Ala Ile Cys Glu Gln Val Glu
                85                  90                  95

Asp Pro Ser Lys Ala Lys Gly Ile Val Lys Arg Asp Val Ile Arg Val
            100                 105                 110

Ile Thr Pro Gly Thr Phe Phe Glu Arg Glu Thr Gly Gly Leu Cys Ser
        115                 120                 125

Leu Tyr Arg Lys Gly Lys Ser Tyr Leu Val Ser Tyr Leu Asn Leu Ser
    130                 135                 140

Val Gly Glu Phe Ile Gly Ala Lys Val Lys Glu Glu Leu Ile Asp
145                 150                 155                 160

Phe Leu Ser Lys Phe Asn Ile Arg Glu Val Leu Val Lys Lys Gly Glu
                165                 170                 175

Lys Leu Pro Glu Lys Leu Glu Lys Val Leu Lys Leu His Ile Thr Glu
            180                 185                 190

Leu Glu Glu Glu Phe Phe Glu Glu Gly Lys Glu Glu Leu Leu Lys Asp
        195                 200                 205

Tyr Gly Val Pro Ser Ile Lys Ala Phe Gly Phe Gln Asp Glu Asp Leu
    210                 215                 220
```

```
Ser Leu Ser Leu Gly Ala Val Tyr Arg Tyr Ala Lys Ala Thr Gln Lys
225                 230                 235                 240

Ser Phe Thr Pro Leu Ile Pro Lys Pro Lys Pro Tyr Val Asp Glu Gly
            245                 250                 255

Tyr Val Lys Leu Asp Leu Lys Ala Val Lys Gly Leu Glu Ile Thr Glu
            260                 265                 270

Ser Ile Glu Gly Arg Lys Asp Leu Ser Leu Phe Lys Val Val Asp Arg
        275                 280                 285

Thr Leu Thr Gly Met Gly Arg Arg Leu Arg Phe Arg Leu Leu Asn
290                 295                 300

Pro Phe Arg Ser Ile Glu Arg Ile Arg Lys Val Gln Glu Ala Val Glu
305                 310                 315                 320

Glu Leu Ile Asn Lys Arg Glu Val Leu Asn Glu Ile Arg Lys Thr Leu
                325                 330                 335

Glu Gly Met Ser Asp Leu Glu Arg Leu Val Ser Arg Ile Ser Ser Asn
                340                 345                 350

Met Ala Ser Pro Arg Glu Leu Ile His Leu Lys Asn Ser Leu Arg Lys
            355                 360                 365

Ala Glu Glu Leu Arg Lys Ile Leu Ser Leu Leu Asp Ser Glu Ile Phe
370                 375                 380

Lys Glu Ile Glu Gly Ser Leu Leu Asn Leu Asn Lys Val Ala Asp Leu
385                 390                 395                 400

Ile Asp Lys Thr Leu Val Asp Asp Pro Pro Leu His Val Lys Glu Gly
                405                 410                 415

Gly Leu Ile Lys Pro Gly Val Asn Ala Tyr Leu Asp Glu Leu Arg Phe
            420                 425                 430

Ile Arg Glu Asn Ala Glu Lys Leu Leu Lys Glu Tyr Glu Lys Lys Leu
        435                 440                 445

Lys Lys Glu Thr Gly Ile Gln Ser Leu Lys Ile Gly Tyr Asn Lys Val
450                 455                 460

Met Gly Tyr Tyr Ile Glu Val Thr Lys Ala Asn Val Lys Tyr Val Pro
465                 470                 475                 480

Glu His Phe Arg Arg Arg Gln Thr Leu Ser Asn Ala Glu Arg Tyr Thr
                485                 490                 495

Thr Glu Glu Leu Gln Arg Leu Glu Glu Lys Ile Leu Ser Ala Gln Thr
            500                 505                 510

Arg Ile Asn Glu Leu Glu Tyr Glu Leu Tyr Arg Glu Leu Arg Glu Glu
        515                 520                 525

Val Val Lys Glu Leu Asp Lys Val Gly Asn Asn Ala Thr Leu Ile Gly
530                 535                 540

Glu Val Asp Tyr Ile Gln Ser Leu Ala Trp Leu Ala Leu Glu Lys Gly
545                 550                 555                 560

Trp Val Lys Pro Glu Val His Glu Gly Tyr Glu Leu Ile Ile Glu Glu
                565                 570                 575

Gly Lys His Pro Val Ile Glu Glu Phe Thr Lys Asn Tyr Val Pro Asn
            580                 585                 590

Asp Thr Lys Leu Thr Glu Glu Phe Ile His Val Ile Thr Gly Pro
        595                 600                 605

Asn Met Ala Gly Lys Ser Ser Tyr Ile Arg Gln Val Gly Val Leu Thr
            610                 615                 620

Leu Leu Ala His Thr Gly Ser Phe Leu Pro Val Lys Ser Ala Arg Ile
625                 630                 635                 640

Pro Leu Val Asp Ala Ile Phe Thr Arg Ile Gly Ser Gly Asp Val Leu
```

```
                    645                 650                 655
Ala Leu Gly Val Ser Thr Phe Met Asn Glu Met Leu Asp Val Ser Asn
                660                 665                 670

Ile Leu Asn Asn Ala Thr Lys Arg Ser Leu Ile Ile Leu Asp Glu Val
            675                 680                 685

Gly Arg Gly Thr Ser Thr Tyr Asp Gly Ile Ala Ile Ser Lys Ala Ile
        690                 695                 700

Val Lys Tyr Ile Ser Glu Lys Ile Gly Ala Lys Thr Leu Leu Ala Thr
705                 710                 715                 720

His Tyr Leu Glu Leu Thr Glu Leu Glu Arg Lys Val Lys Gly Val Lys
                725                 730                 735

Asn Tyr His Met Glu Val Glu Glu Thr Asp Glu Gly Ile Arg Phe Leu
                740                 745                 750

Tyr Ile Leu Lys Glu Gly Arg Ala Lys Gly Ser Phe Gly Ile Asp Val
            755                 760                 765

Ala Lys Leu Ala Gly Leu Pro Glu Glu Val Val Arg Glu Ala Lys Lys
        770                 775                 780

Ile Leu Lys Glu Leu Glu Gly Glu Lys Gly Lys Gln Glu Val Leu Pro
785                 790                 795                 800

Phe Leu Glu Glu Thr Tyr Lys Lys Ser Val Asp Glu Glu Lys Leu Asn
                805                 810                 815

Phe Tyr Glu Glu Ile Ile Lys Glu Ile Glu Glu Ile Asp Ile Gly Asn
                820                 825                 830

Thr Thr Pro Val Lys Ala Leu Leu Ile Leu Ala Glu Leu Lys Glu Arg
            835                 840                 845

Ile Lys Ser Phe Ile Lys Arg
    850                 855

<210> SEQ ID NO 3
<211> LENGTH: 853
<212> TYPE: PRT
<213> ORGANISM: Escherichia coli

<400> SEQUENCE: 3

Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
            20                  25                  30

Met Gly Asp Phe Tyr Glu Leu Phe Tyr Asp Asp Ala Lys Arg Ala Ser
        35                  40                  45

Gln Leu Leu Asp Ile Ser Leu Thr Lys Arg Gly Ala Ser Ala Gly Glu
    50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
        115                 120                 125

Gln Asp Asn Leu Leu Ala Ala Ile Trp Gln Asp Ser Lys Gly Phe Gly
    130                 135                 140

Tyr Ala Thr Leu Asp Ile Ser Ser Gly Arg Phe Arg Leu Ser Glu Pro
145                 150                 155                 160
```

```
Ala Asp Arg Glu Thr Met Ala Ala Glu Leu Gln Arg Thr Asn Pro Ala
                165                 170                 175
Glu Leu Leu Tyr Ala Glu Asp Phe Ala Glu Met Ser Leu Ile Glu Gly
            180                 185                 190
Arg Arg Gly Leu Arg Arg Pro Leu Trp Glu Phe Glu Ile Asp Thr
        195                 200                 205
Ala Arg Gln Gln Leu Asn Leu Gln Phe Gly Thr Arg Asp Leu Val Gly
210                 215                 220
Phe Gly Val Glu Asn Ala Pro Arg Gly Leu Cys Ala Ala Gly Cys Leu
225                 230                 235                 240
Leu Gln Tyr Ala Lys Asp Thr Gln Arg Thr Thr Leu Pro His Ile Arg
                245                 250                 255
Ser Ile Thr Met Glu Arg Glu Gln Asp Ser Ile Ile Met Asp Ala Ala
            260                 265                 270
Thr Arg Arg Asn Leu Glu Ile Thr Gln Asn Leu Ala Gly Gly Ala Glu
        275                 280                 285
Asn Thr Leu Ala Ser Val Leu Asp Cys Thr Val Thr Pro Met Gly Ser
290                 295                 300
Arg Met Leu Lys Arg Trp Leu His Met Pro Val Arg Asp Thr Arg Val
305                 310                 315                 320
Leu Leu Glu Arg Gln Gln Thr Ile Gly Ala Leu Gln Asp Phe Thr Ala
                325                 330                 335
Gly Leu Gln Pro Val Leu Arg Gln Val Gly Asp Leu Glu Arg Ile Leu
            340                 345                 350
Ala Arg Leu Ala Leu Arg Thr Ala Arg Pro Arg Asp Leu Ala Arg Met
        355                 360                 365
Arg His Ala Phe Gln Gln Leu Pro Glu Leu Arg Ala Gln Leu Glu Thr
370                 375                 380
Val Asp Ser Ala Pro Val Gln Ala Leu Arg Glu Lys Met Gly Glu Phe
385                 390                 395                 400
Ala Glu Leu Arg Asp Leu Leu Glu Arg Ala Ile Ile Asp Thr Pro Pro
                405                 410                 415
Val Leu Val Arg Asp Gly Gly Val Ile Ala Ser Gly Tyr Asn Glu Glu
            420                 425                 430
Leu Asp Glu Trp Arg Ala Leu Ala Asp Gly Ala Thr Asp Tyr Leu Glu
        435                 440                 445
Arg Leu Glu Val Arg Glu Arg Glu Arg Thr Gly Leu Asp Thr Leu Lys
450                 455                 460
Val Gly Phe Asn Ala Val His Gly Tyr Tyr Ile Gln Ile Ser Arg Gly
465                 470                 475                 480
Gln Ser His Leu Ala Pro Ile Asn Tyr Met Arg Arg Gln Thr Leu Lys
                485                 490                 495
Asn Ala Glu Arg Tyr Ile Ile Pro Glu Leu Lys Glu Tyr Glu Asp Lys
            500                 505                 510
Val Leu Thr Ser Lys Gly Lys Ala Leu Ala Leu Glu Lys Gln Leu Tyr
        515                 520                 525
Glu Glu Leu Phe Asp Leu Leu Leu Pro His Leu Glu Ala Leu Gln Gln
530                 535                 540
Ser Ala Ser Ala Leu Ala Glu Leu Asp Val Leu Val Asn Leu Ala Glu
545                 550                 555                 560
Arg Ala Tyr Thr Leu Asn Tyr Thr Cys Pro Thr Phe Ile Asp Lys Pro
                565                 570                 575
Gly Ile Arg Ile Thr Glu Gly Arg His Pro Val Val Glu Gln Val Leu
```

```
                    580                     585                     590
Asn Glu Pro Phe Ile Ala Asn Pro Leu Asn Leu Ser Pro Gln Arg Arg
        595                     600                     605

Met Leu Ile Ile Thr Gly Pro Asn Met Gly Gly Lys Ser Thr Tyr Met
    610                     615                     620

Arg Gln Thr Ala Leu Ile Ala Leu Met Ala Tyr Ile Gly Ser Tyr Val
625                     630                     635                     640

Pro Ala Gln Lys Val Glu Ile Gly Pro Ile Asp Arg Ile Phe Thr Arg
                645                     650                     655

Val Gly Ala Ala Asp Asp Leu Ala Ser Gly Arg Ser Thr Phe Met Val
                660                     665                     670

Glu Met Thr Glu Thr Ala Asn Ile Leu His Asn Ala Thr Glu Tyr Ser
            675                     680                     685

Leu Val Leu Met Asp Glu Ile Gly Arg Gly Thr Ser Thr Tyr Asp Gly
        690                     695                     700

Leu Ser Leu Ala Trp Ala Cys Ala Glu Asn Leu Ala Asn Lys Ile Lys
705                     710                     715                     720

Ala Leu Thr Leu Phe Ala Thr His Tyr Phe Glu Leu Thr Gln Leu Pro
                725                     730                     735

Glu Lys Met Glu Gly Val Ala Asn Val His Leu Asp Ala Leu Glu His
            740                     745                     750

Gly Asp Thr Ile Ala Phe Met His Ser Val Gln Asp Gly Ala Ala Ser
        755                     760                     765

Lys Ser Tyr Gly Leu Ala Val Ala Leu Ala Gly Val Pro Lys Glu
770                     775                     780

Val Ile Lys Arg Ala Arg Gln Lys Leu Arg Glu Leu Glu Ser Ile Ser
785                     790                     795                     800

Pro Asn Ala Ala Ala Thr Gln Val Asp Gly Thr Gln Met Ser Leu Leu
                805                     810                     815

Ser Val Pro Glu Glu Thr Ser Pro Ala Val Glu Ala Leu Glu Asn Leu
            820                     825                     830

Asp Pro Asp Ser Leu Thr Pro Arg Gln Ala Leu Glu Trp Ile Tyr Arg
        835                     840                     845

Leu Lys Ser Leu Val
    850

<210> SEQ ID NO 4
<211> LENGTH: 2382
<212> TYPE: DNA
<213> ORGANISM: Thermotoga maritima
<220> FEATURE:
<221> NAME/KEY: CDS
<222> LOCATION: (1)...(2379)

<400> SEQUENCE: 4 gtg aag gta act ccc ctc atg gaa cag tac ctg aga ata aaa gaa cag      48
Val Lys Val Thr Pro Leu Met Glu Gln Tyr Leu Arg Ile Lys Glu Gln
1               5                   10                  15 tac aaa gat tcc att ctg ctg ttt cga ctg gga gat ttt tac gag gcg      96
Tyr Lys Asp Ser Ile Leu Leu Phe Arg Leu Gly Asp Phe Tyr Glu Ala
                20                  25                  30 ttt ttc gaa gac gca aag atc gtt tcg aag gtt ctg aac ata gtt ctc     144
Phe Phe Glu Asp Ala Lys Ile Val Ser Lys Val Leu Asn Ile Val Leu
            35                  40                  45 aca aga agg cag gac gct ccc atg gcg ggc atc ccg tac cac gcg ctg     192
Thr Arg Arg Gln Asp Ala Pro Met Ala Gly Ile Pro Tyr His Ala Leu
        50                  55                  60
```

```
aac acc tac ctg aaa aag ctc gtc gaa gcg ggc tac aag gtg gca atc      240
Asn Thr Tyr Leu Lys Lys Leu Val Glu Ala Gly Tyr Lys Val Ala Ile
 65                  70                  75                  80 tgc gat caa atg gaa gaa cct tcg aag tcg aag aaa ttg atc aga agg      288
Cys Asp Gln Met Glu Glu Pro Ser Lys Ser Lys Lys Leu Ile Arg Arg
                 85                  90                  95 gaa gtc acg cgc gtt gtc act ccc ggc tcc atc gta gag gat gag ttt      336
Glu Val Thr Arg Val Val Thr Pro Gly Ser Ile Val Glu Asp Glu Phe
            100                 105                 110 ctc agc gaa acg aac aac tac atg gcc gtt gtc tca gaa gag aaa gga      384
Leu Ser Glu Thr Asn Asn Tyr Met Ala Val Val Ser Glu Glu Lys Gly
        115                 120                 125 cgg tac tgt acg gtt ttc tgt gat gtc tcg aca ggt gag gtc ctg gtt      432
Arg Tyr Cys Thr Val Phe Cys Asp Val Ser Thr Gly Glu Val Leu Val
    130                 135                 140 cat gaa agt tca gac gaa cag gaa act ttg gac ctg ctg aag aat tac      480
His Glu Ser Ser Asp Glu Gln Glu Thr Leu Asp Leu Leu Lys Asn Tyr
145                 150                 155                 160 tcc att tcc cag atc atc tgt cca gag cac ctg aaa tct tct ttg aag      528
Ser Ile Ser Gln Ile Ile Cys Pro Glu His Leu Lys Ser Ser Leu Lys
                165                 170                 175 gaa cgc ttt cca ggt gtt tac aca gaa acc ata agc gag tgg tat ttc      576
Glu Arg Phe Pro Gly Val Tyr Thr Glu Thr Ile Ser Glu Trp Tyr Phe
            180                 185                 190 tca gat ctg gaa gaa gtg gaa aaa gcc tac aat ctg aaa gac att cat      624
Ser Asp Leu Glu Glu Val Glu Lys Ala Tyr Asn Leu Lys Asp Ile His
        195                 200                 205 cat ttc gag ctt tcg ccc ctt gcg ctg aaa gcc ctt gcg gcg ctg ata      672
His Phe Glu Leu Ser Pro Leu Ala Leu Lys Ala Leu Ala Ala Leu Ile
    210                 215                 220 aag tat gtc aag tac acg atg atc ggg gaa gat ctg aat ctg aaa ccc      720
Lys Tyr Val Lys Tyr Thr Met Ile Gly Glu Asp Leu Asn Leu Lys Pro
225                 230                 235                 240 cct ctt ctc atc tcc cag aga gac tac atg ata ctc gat tcc gca acg      768
Pro Leu Leu Ile Ser Gln Arg Asp Tyr Met Ile Leu Asp Ser Ala Thr
                245                 250                 255 gtg gaa aat ctt tct tgg att ccc ggt gac agg gga aag aat ctt ttc      816
Val Glu Asn Leu Ser Trp Ile Pro Gly Asp Arg Gly Lys Asn Leu Phe
            260                 265                 270 gat gtc ctg aac aac acg gaa act cct atg ggg gct cgt ctt ggg aaa      864
Asp Val Leu Asn Asn Thr Glu Thr Pro Met Gly Ala Arg Leu Gly Lys
        275                 280                 285 aag tgg att ctc cac cct ctg gtc gac aga aaa cag atc gaa gaa agg      912
Lys Trp Ile Leu His Pro Leu Val Asp Arg Lys Gln Ile Glu Glu Arg
    290                 295                 300 ctc aag gct gtg gaa aga ctg gtg aac gac agg gtg agc ctg gag gag      960
Leu Lys Ala Val Glu Arg Leu Val Asn Asp Arg Val Ser Leu Glu Glu
305                 310                 315                 320 atg agg aac ctt ctt tcg aac gtg agg gat gtg gag cgg atc gtt tcg     1008
Met Arg Asn Leu Leu Ser Asn Val Arg Asp Val Glu Arg Ile Val Ser
                325                 330                 335 cgg gtg gag tac aac aga tcc gtt ccc agg gac tta gtg gca ctc aga     1056
Arg Val Glu Tyr Asn Arg Ser Val Pro Arg Asp Leu Val Ala Leu Arg
            340                 345                 350 gag aca ctg gag atc atc ccg aaa ctg aac gaa gtt ctt tca acc ttc     1104
Glu Thr Leu Glu Ile Ile Pro Lys Leu Asn Glu Val Leu Ser Thr Phe
        355                 360                 365 ggt gtg ttc aag aaa ctc gct ttc ccg gaa gga ctg gtt gat ctg ctt     1152
Gly Val Phe Lys Lys Leu Ala Phe Pro Glu Gly Leu Val Asp Leu Leu
```

-continued

```
        370                 375                 380
cga aaa gcc att gaa gat gat ccg gtg gga agc ccc ggc gag gga aaa    1200
Arg Lys Ala Ile Glu Asp Asp Pro Val Gly Ser Pro Gly Glu Gly Lys
385                 390                 395                 400 gtt ata aag aga gga ttc tca tct gaa ctc gac gaa tac agg gat ctt    1248
Val Ile Lys Arg Gly Phe Ser Ser Glu Leu Asp Glu Tyr Arg Asp Leu
                405                 410                 415 ctg gaa cat gcc gaa gag agg ctc aaa gag ttc gag gag aag gag aga    1296
Leu Glu His Ala Glu Glu Arg Leu Lys Glu Phe Glu Glu Lys Glu Arg
            420                 425                 430 gaa aga aca ggc atc caa aaa ctg cgg gtt gga tac aac cag gtt ttt    1344
Glu Arg Thr Gly Ile Gln Lys Leu Arg Val Gly Tyr Asn Gln Val Phe
        435                 440                 445 ggt tac tac ata gag gtg acg aag gcg aat ctg gat aag att ccc gac    1392
Gly Tyr Tyr Ile Glu Val Thr Lys Ala Asn Leu Asp Lys Ile Pro Asp
    450                 455                 460 gat tac gaa aga aaa caa aca ctc gtc aat tct gaa aga ttc atc aca    1440
Asp Tyr Glu Arg Lys Gln Thr Leu Val Asn Ser Glu Arg Phe Ile Thr
465                 470                 475                 480 ccc gaa ttg aag gag ttc gag aca aag ata atg gcc gct aaa gag aga    1488
Pro Glu Leu Lys Glu Phe Glu Thr Lys Ile Met Ala Ala Lys Glu Arg
                485                 490                 495 ata gaa gaa ctg gaa aag gaa ctc ttc aca agc gtg tgc gaa gag gtg    1536
Ile Glu Glu Leu Glu Lys Glu Leu Phe Thr Ser Val Cys Glu Glu Val
            500                 505                 510 aaa aag cac aaa gaa gtt ctc ctt gag atc tcg gag gat ctg gca aag    1584
Lys Lys His Lys Glu Val Leu Leu Glu Ile Ser Glu Asp Leu Ala Lys
        515                 520                 525 ata gat gcg ctt tcg acg tta gca tac gac gct att atg tac aac tac    1632
Ile Asp Ala Leu Ser Thr Leu Ala Tyr Asp Ala Ile Met Tyr Asn Tyr
    530                 535                 540 aca aaa ccc gtc ttt tca gaa gac aga ctg gag atc aaa ggt gga aga    1680
Thr Lys Pro Val Phe Ser Glu Asp Arg Leu Glu Ile Lys Gly Gly Arg
545                 550                 555                 560 cac ccg gtc gtt gaa agg ttc aca cag aat ttt gtt gaa aac gat att    1728
His Pro Val Val Glu Arg Phe Thr Gln Asn Phe Val Glu Asn Asp Ile
                565                 570                 575 tac atg gac aac gag aag aga ttt gtg gta ata acg ggt ccc aac atg    1776
Tyr Met Asp Asn Glu Lys Arg Phe Val Val Ile Thr Gly Pro Asn Met
            580                 585                 590 agc ggg aag tcc act ttc atc aga cag gtg ggt ctc ata tcc ctc atg    1824
Ser Gly Lys Ser Thr Phe Ile Arg Gln Val Gly Leu Ile Ser Leu Met
        595                 600                 605 gcg cag ata gga tcg ttt gtg ccg gcg cag aag gcg att ctt cca gtg    1872
Ala Gln Ile Gly Ser Phe Val Pro Ala Gln Lys Ala Ile Leu Pro Val
    610                 615                 620 ttc gac agg att ttc acg cga atg ggt gcc aga gac gat ctc gct ggt    1920
Phe Asp Arg Ile Phe Thr Arg Met Gly Ala Arg Asp Asp Leu Ala Gly
625                 630                 635                 640 ggt aga agt acg ttc ctt gtc gag atg aac gag atg gcg ctc atc ctt    1968
Gly Arg Ser Thr Phe Leu Val Glu Met Asn Glu Met Ala Leu Ile Leu
                645                 650                 655 ctg aaa tca aca aat aag agt ctg gtt ctc ctg gac gag gtg gga aga    2016
Leu Lys Ser Thr Asn Lys Ser Leu Val Leu Leu Asp Glu Val Gly Arg
            660                 665                 670 ggt aca agc acc cag gac ggc gtc agc ata gcc tgg gca atc tca gag    2064
Gly Thr Ser Thr Gln Asp Gly Val Ser Ile Ala Trp Ala Ile Ser Glu
        675                 680                 685 gaa ctc ata aag aga gga tgt aag gtg ctg ttt gcc act cat ttc acg    2112
```

-continued

```
Glu Leu Ile Lys Arg Gly Cys Lys Val Leu Phe Ala Thr His Phe Thr
        690                 695                 700
gaa ctc acg gaa ctc gaa aaa cac ttt ccg cag gtt cag aac aaa acc    2160
Glu Leu Thr Glu Leu Glu Lys His Phe Pro Gln Val Gln Asn Lys Thr
705                 710                 715                 720
att ctg gta aaa gaa gaa ggc aaa aac gtg ata ttc acc cac aag gtg    2208
Ile Leu Val Lys Glu Glu Gly Lys Asn Val Ile Phe Thr His Lys Val
                725                 730                 735
gtg gac ggt gtg gca gac aga agt tac gga ata gag gtc gca aag ata    2256
Val Asp Gly Val Ala Asp Arg Ser Tyr Gly Ile Glu Val Ala Lys Ile
            740                 745                 750
gcg ggt att cct gac agg gtt ata aac aga gcc tat gaa att ctg gag    2304
Ala Gly Ile Pro Asp Arg Val Ile Asn Arg Ala Tyr Glu Ile Leu Glu
        755                 760                 765
agg aat ttc aaa aac aac acg aag aaa aac gga aaa tcg aac aga ttc    2352
Arg Asn Phe Lys Asn Asn Thr Lys Lys Asn Gly Lys Ser Asn Arg Phe
770                 775                 780
agt cag caa att cct ctc ttt cct gtt tga                            2382
Ser Gln Gln Ile Pro Leu Phe Pro Val
785                 790
```

<210> SEQ ID NO 5
<211> LENGTH: 793
<212> TYPE: PRT
<213> ORGANISM: Thermotoga maritima

<400> SEQUENCE: 5

```
Val Lys Val Thr Pro Leu Met Glu Gln Tyr Leu Arg Ile Lys Glu Gln
1               5                   10                  15
Tyr Lys Asp Ser Ile Leu Leu Phe Arg Leu Gly Asp Phe Tyr Glu Ala
                20                  25                  30
Phe Phe Glu Asp Ala Lys Ile Val Ser Lys Val Leu Asn Ile Val Leu
            35                  40                  45
Thr Arg Arg Gln Asp Ala Pro Met Ala Gly Ile Pro Tyr His Ala Leu
        50                  55                  60
Asn Thr Tyr Leu Lys Lys Leu Val Glu Ala Gly Tyr Lys Val Ala Ile
65                  70                  75                  80
Cys Asp Gln Met Glu Glu Pro Ser Lys Ser Lys Lys Leu Ile Arg Arg
                85                  90                  95
Glu Val Thr Arg Val Val Thr Pro Gly Ser Ile Val Glu Asp Glu Phe
            100                 105                 110
Leu Ser Glu Thr Asn Asn Tyr Met Ala Val Val Ser Glu Glu Lys Gly
        115                 120                 125
Arg Tyr Cys Thr Val Phe Cys Asp Val Ser Thr Gly Glu Val Leu Val
    130                 135                 140
His Glu Ser Ser Asp Glu Gln Glu Thr Leu Asp Leu Leu Lys Asn Tyr
145                 150                 155                 160
Ser Ile Ser Gln Ile Ile Cys Pro Glu His Leu Lys Ser Ser Leu Lys
                165                 170                 175
Glu Arg Phe Pro Gly Val Tyr Thr Glu Thr Ile Ser Glu Trp Tyr Phe
            180                 185                 190
Ser Asp Leu Glu Glu Val Glu Lys Ala Tyr Asn Leu Lys Asp Ile His
        195                 200                 205
His Phe Glu Leu Ser Pro Leu Ala Leu Lys Ala Leu Ala Ala Leu Ile
    210                 215                 220
Lys Tyr Val Lys Tyr Thr Met Ile Gly Glu Asp Leu Asn Leu Lys Pro
225                 230                 235                 240
```

-continued

```
Pro Leu Leu Ile Ser Gln Arg Asp Tyr Met Ile Leu Asp Ser Ala Thr
            245                 250                 255

Val Glu Asn Leu Ser Trp Ile Pro Gly Asp Arg Gly Lys Asn Leu Phe
        260                 265                 270

Asp Val Leu Asn Asn Thr Glu Thr Pro Met Gly Ala Arg Leu Gly Lys
        275                 280                 285

Lys Trp Ile Leu His Pro Leu Val Asp Arg Lys Gln Ile Glu Glu Arg
        290                 295                 300

Leu Lys Ala Val Glu Arg Leu Val Asn Asp Arg Val Ser Leu Glu Glu
305                 310                 315                 320

Met Arg Asn Leu Leu Ser Asn Val Arg Asp Val Glu Arg Ile Val Ser
                325                 330                 335

Arg Val Glu Tyr Asn Arg Ser Val Pro Arg Asp Leu Val Ala Leu Arg
                340                 345                 350

Glu Thr Leu Glu Ile Ile Pro Lys Leu Asn Glu Val Leu Ser Thr Phe
            355                 360                 365

Gly Val Phe Lys Lys Leu Ala Phe Pro Glu Gly Leu Val Asp Leu Leu
        370                 375                 380

Arg Lys Ala Ile Glu Asp Asp Pro Val Gly Ser Pro Gly Glu Gly Lys
385                 390                 395                 400

Val Ile Lys Arg Gly Phe Ser Ser Glu Leu Asp Glu Tyr Arg Asp Leu
                405                 410                 415

Leu Glu His Ala Glu Glu Arg Leu Lys Glu Phe Glu Glu Lys Glu Arg
                420                 425                 430

Glu Arg Thr Gly Ile Gln Lys Leu Arg Val Gly Tyr Asn Gln Val Phe
            435                 440                 445

Gly Tyr Tyr Ile Glu Val Thr Lys Ala Asn Leu Asp Lys Ile Pro Asp
        450                 455                 460

Asp Tyr Glu Arg Lys Gln Thr Leu Val Asn Ser Glu Arg Phe Ile Thr
465                 470                 475                 480

Pro Glu Leu Lys Glu Phe Glu Thr Lys Ile Met Ala Ala Lys Glu Arg
                485                 490                 495

Ile Glu Glu Leu Glu Lys Glu Leu Phe Thr Ser Val Cys Glu Glu Val
            500                 505                 510

Lys Lys His Lys Glu Val Leu Leu Glu Ile Ser Glu Asp Leu Ala Lys
        515                 520                 525

Ile Asp Ala Leu Ser Thr Leu Ala Tyr Asp Ala Ile Met Tyr Asn Tyr
        530                 535                 540

Thr Lys Pro Val Phe Ser Glu Asp Arg Leu Glu Ile Lys Gly Gly Arg
545                 550                 555                 560

His Pro Val Val Glu Arg Phe Thr Gln Asn Phe Val Glu Asn Asp Ile
                565                 570                 575

Tyr Met Asp Asn Glu Lys Arg Phe Val Val Ile Thr Gly Pro Asn Met
                580                 585                 590

Ser Gly Lys Ser Thr Phe Ile Arg Gln Val Gly Leu Ile Ser Leu Met
        595                 600                 605

Ala Gln Ile Gly Ser Phe Val Pro Ala Gln Lys Ala Ile Leu Pro Val
        610                 615                 620

Phe Asp Arg Ile Phe Thr Arg Met Gly Ala Arg Asp Asp Leu Ala Gly
625                 630                 635                 640

Gly Arg Ser Thr Phe Leu Val Glu Met Asn Glu Met Ala Leu Ile Leu
                645                 650                 655
```

```
Leu Lys Ser Thr Asn Lys Ser Leu Val Leu Asp Glu Val Gly Arg
            660                 665                 670

Gly Thr Ser Thr Gln Asp Gly Val Ser Ile Ala Trp Ala Ile Ser Glu
        675                 680                 685

Glu Leu Ile Lys Arg Gly Cys Lys Val Leu Phe Ala Thr His Phe Thr
    690                 695                 700

Glu Leu Thr Glu Leu Glu Lys His Phe Pro Gln Val Gln Asn Lys Thr
705                 710                 715                 720

Ile Leu Val Lys Glu Glu Gly Lys Asn Val Ile Phe Thr His Lys Val
                725                 730                 735

Val Asp Gly Val Ala Asp Arg Ser Tyr Gly Ile Glu Val Ala Lys Ile
            740                 745                 750

Ala Gly Ile Pro Asp Arg Val Ile Asn Arg Ala Tyr Glu Ile Leu Glu
        755                 760                 765

Arg Asn Phe Lys Asn Asn Thr Lys Lys Asn Gly Lys Ser Asn Arg Phe
    770                 775                 780

Ser Gln Gln Ile Pro Leu Phe Pro Val
785                 790

<210> SEQ ID NO 6
<211> LENGTH: 102
<212> TYPE: DNA
<213> ORGANISM: Thermus thermophilus

<400> SEQUENCE: 6
aagtccacct tcctccgccg gaccgccctc atcgccctcc tcgcccagat cgggagcttc      60
gcgcccgccg aggggctgct gcttcccctc tttgacggga tc                       102

<210> SEQ ID NO 7
<211> LENGTH: 102
<212> TYPE: DNA
<213> ORGANISM: Thermus aquaticus

<400> SEQUENCE: 7
aagtccacct ttctgcgcca gacggccctc atcgccctcc tggcccaggt ggggagcttc      60
gtgcccgccg aggaggccca tcttcccctc tttgacggca tc                       102

<210> SEQ ID NO 8
<211> LENGTH: 34
<212> TYPE: PRT
<213> ORGANISM: Thermus aquaticus

<400> SEQUENCE: 8

Lys Ser Thr Phe Leu Arg Gln Thr Ala Leu Ile Ala Leu Leu Ala Gln
1               5                   10                  15

Val Gly Ser Phe Val Pro Ala Glu Glu Ala His Leu Pro Leu Phe Asp
            20                  25                  30

Gly Ile

<210> SEQ ID NO 9
<211> LENGTH: 34
<212> TYPE: PRT
<213> ORGANISM: Thermus thermophilus

<400> SEQUENCE: 9

Lys Ser Thr Phe Leu Arg Arg Thr Ala Leu Ile Ala Leu Leu Ala Gln
1               5                   10                  15

Ile Gly Ser Phe Ala Pro Ala Glu Gly Leu Leu Leu Pro Leu Phe Asp
```

```
                    20                  25                  30
Gly Ile

<210> SEQ ID NO 10
<211> LENGTH: 10
<212> TYPE: DNA
<213> ORGANISM: Escherichia coli

<400> SEQUENCE: 10
ggggatcctc                                                              10

<210> SEQ ID NO 11
<211> LENGTH: 9
<212> TYPE: DNA
<213> ORGANISM: Artificial Sequence
<220> FEATURE:
<223> OTHER INFORMATION: Oligonucleotide

<400> SEQUENCE: 11 gggaccctc                                                               9

<210> SEQ ID NO 12
<211> LENGTH: 12
<212> TYPE: DNA
<213> ORGANISM: Artificial Sequence
<220> FEATURE:
<223> OTHER INFORMATION: Oligonucleotide

<400> SEQUENCE: 12
gggggatccc tc                                                           12

<210> SEQ ID NO 13
<211> LENGTH: 13
<212> TYPE: DNA
<213> ORGANISM: Artificial Sequence
<220> FEATURE:
<223> OTHER INFORMATION: Oligonucleotide

<400> SEQUENCE: 13
ggggatcccc ctc                                                          13

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
tacgccagct ggcgaaaggg                                                   20

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
aatgcagctg gcacgacagg                                                   20

<210> SEQ ID NO 16
<211> LENGTH: 19
<212> TYPE: DNA
<213> ORGANISM: Artificial Sequence
```

```
<220> FEATURE:
<223> OTHER INFORMATION: Oligonucleotide

<400> SEQUENCE: 16
gactctagag gatccatgt                                                        19

<210> SEQ ID NO 17
<211> LENGTH: 35
<212> TYPE: DNA
<213> ORGANISM: Artificial Sequence
<220> FEATURE:
<223> OTHER INFORMATION: PCR primer

<400> SEQUENCE: 17
augaugauga ugaucgcaca tttccccgaa aagtg                                      35

<210> SEQ ID NO 18
<211> LENGTH: 33
<212> TYPE: DNA
<213> ORGANISM: Artificial Sequence
<220> FEATURE:
<223> OTHER INFORMATION: PCR primer

<400> SEQUENCE: 18
aucaucauca ucaugcgcgg aaccccuauu ugu                                        33

<210> SEQ ID NO 19
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(25)
<223> OTHER INFORMATION: n = A,T,C or G

<400> SEQUENCE: 19
gcggaattcc saacatgggs ggnaa                                                 25

<210> SEQ ID NO 20
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(26)
<223> OTHER INFORMATION: n = A,T,C or G

<400> SEQUENCE: 20
gcgagatcta agtagtgsgt ngcraa                                                26

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
gcgagatctc acctgtctta tgtagctcga                                            30

<210> SEQ ID NO 22
<211> LENGTH: 30
<212> TYPE: DNA
<213> ORGANISM: Artificial Sequence
<220> FEATURE:
```

<223> OTHER INFORMATION: primer

<400> SEQUENCE: 22
gcgagatctc atctcgacaa ggaacgtact                              30

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
gcggaattca tgggggaytt ytayga                                  26

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
gcggaattcg ggaaaggatt cccatgttcg                              30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
gcgagatctc ctttccagcg ggtcttgaag                              30

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gcggaattcc gggcatcccg taccactcgc                              30

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
gcgagatctg gagcgtccct gcccttcttg                              30

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
gcggaattct caaccttcat gaacgagatg                              30

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
gcgagatctc gagcctattc tcatgaatat                              30

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
gcggaattcg aggtgggaag aggtacaagc                              30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
gcgagatctc atctcgacaa ggaacgtact                              30

<210> SEQ ID NO 32
<211> LENGTH: 30
<212> TYPE: DNA
<213> ORGANISM: Artificial Sequence
<220> FEATURE:
<223> OTHER INFORMATION: PCR primer

<400> SEQUENCE: 32
gcgaagctta tgaaggtaac tcccctcatg                              30

<210> SEQ ID NO 33
<211> LENGTH: 30
<212> TYPE: DNA
<213> ORGANISM: Artificial Sequence
<220> FEATURE:
<223> OTHER INFORMATION: PCR primer

<400> SEQUENCE: 33
gcgggatcca cgcatcgata ctggttaaaa                              30

<210> SEQ ID NO 34
<211> LENGTH: 30
<212> TYPE: DNA
<213> ORGANISM: Artificial Sequence
<220> FEATURE:
<223> OTHER INFORMATION: PCR primer

<400> SEQUENCE: 34
gcgccatggg aaaagaggag aaagagctca                              30

<210> SEQ ID NO 35
<211> LENGTH: 30
<212> TYPE: DNA
<213> ORGANISM: Artificial Sequence
<220> FEATURE:
<223> OTHER INFORMATION: PCR primer

```
<400> SEQUENCE: 35
gcgagatctg atactccaga ggtattacaa                                        30

<210> SEQ ID NO 36
<211> LENGTH: 20
<212> TYPE: DNA
<213> ORGANISM: Artificial Sequence
<220> FEATURE:
<223> OTHER INFORMATION: PCR primer

<400> SEQUENCE: 36
aatgcagctg gcacgacagg                                                   20

<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37
ggtacccggg gatcctctag                                                   20

<210> SEQ ID NO 38
<211> LENGTH: 20
<212> TYPE: DNA
<213> ORGANISM: Artificial Sequence
<220> FEATURE:
<223> OTHER INFORMATION: PCR primer

<400> SEQUENCE: 38
tacccgggga tcctctagag                                                   20

<210> SEQ ID NO 39
<211> LENGTH: 1380
<212> TYPE: DNA
<213> ORGANISM: Aquifex pyrophilus
<220> FEATURE:
<221> NAME/KEY: CDS
<222> LOCATION: (61)...(1338)

<400> SEQUENCE: 39
gaattcttaa ggttctcaag ggctgttctt ttctcttttt ccttcctaat ttaataacctc      60 atg ttt gtc aaa atc ctg ccc cca gag gta agg aga aag att gca gcg        108
Met Phe Val Lys Ile Leu Pro Pro Glu Val Arg Arg Lys Ile Ala Ala
 1               5                  10                  15 gga gag gtt ata gac gct ccc gtt gac gtt gta aaa gag ctt ata gag        156
Gly Glu Val Ile Asp Ala Pro Val Asp Val Val Lys Glu Leu Ile Glu
             20                  25                  30 aac tcc ctt gac gct aag gca acg agg att gag att gag gtc gta aaa        204
Asn Ser Leu Asp Ala Lys Ala Thr Arg Ile Glu Ile Glu Val Val Lys
         35                  40                  45 ggg ggg aaa aga ctt atc aga gtt aag gat aac ggg ata ggc att cat        252
Gly Gly Lys Arg Leu Ile Arg Val Lys Asp Asn Gly Ile Gly Ile His
     50                  55                  60 ccc gag gat ata gaa aag gtc gtt tta tcg gga gct acg agc aag ata        300
Pro Glu Asp Ile Glu Lys Val Val Leu Ser Gly Ala Thr Ser Lys Ile
 65                  70                  75                  80 gag aag gaa acg gac ctc ctc aat gtg gaa acc tac gga ttc agg ggg        348
Glu Lys Glu Thr Asp Leu Leu Asn Val Glu Thr Tyr Gly Phe Arg Gly
                 85                  90                  95 gaa gcc ctg tat tcc atc tca agc gta agc aag ttc agg cta agg tca        396
Glu Ala Leu Tyr Ser Ile Ser Ser Val Ser Lys Phe Arg Leu Arg Ser
```

```
agg ttt tac cag gaa aag gaa gga agg gag ata gaa gtt gag ggg gga       444
Arg Phe Tyr Gln Glu Lys Glu Gly Arg Glu Ile Glu Val Glu Gly Gly
        115                 120                 125 acg cta aaa agc gtc aga aga gta gga atg gaa gtt ggg acg gaa gtt       492
Thr Leu Lys Ser Val Arg Arg Val Gly Met Glu Val Gly Thr Glu Val
130                 135                 140 gag gtt tac gac ctc ttt ttt aac ctc ccc gca agg aag aaa ttt tta       540
Glu Val Tyr Asp Leu Phe Phe Asn Leu Pro Ala Arg Lys Lys Phe Leu
145                 150                 155                 160 aga aag gaa gac acc gaa agg aga aag ata acg gag ctc gta aag gag       588
Arg Lys Glu Asp Thr Glu Arg Arg Lys Ile Thr Glu Leu Val Lys Glu
                165                 170                 175 tat gcc ata aca aac ccc cag gtt gac ttt cac ctc ttt tcc gaa gga       636
Tyr Ala Ile Thr Asn Pro Gln Val Asp Phe His Leu Phe Ser Glu Gly
                180                 185                 190 aag gaa acc ctt aac ctg aag aag aag gac cta aaa ggg aga att gag       684
Lys Glu Thr Leu Asn Leu Lys Lys Lys Asp Leu Lys Gly Arg Ile Glu
                195                 200                 205 gaa atc ttt gag tca att ttt gaa gaa gaa agc tcg gaa agg gaa gga       732
Glu Ile Phe Glu Ser Ile Phe Glu Glu Glu Ser Ser Glu Arg Glu Gly
        210                 215                 220 ata aag gta aga gcc ttc ata tca aga aac cag aaa agg gga aag tat       780
Ile Lys Val Arg Ala Phe Ile Ser Arg Asn Gln Lys Arg Gly Lys Tyr
225                 230                 235                 240 tac ctc ttc gta aac tca aga cca gtt tac aac aaa aac tta aaa gaa       828
Tyr Leu Phe Val Asn Ser Arg Pro Val Tyr Asn Lys Asn Leu Lys Glu
                245                 250                 255 tac cta aag aaa acc ttc ggt tat aaa acg ata gtc gtg ctg ttc att       876
Tyr Leu Lys Lys Thr Phe Gly Tyr Lys Thr Ile Val Val Leu Phe Ile
                260                 265                 270 gat att ccc ccc ttt ctc gtt gac ttt aac gtt cac ccc aaa aag aaa       924
Asp Ile Pro Pro Phe Leu Val Asp Phe Asn Val His Pro Lys Lys Lys
                275                 280                 285 gag gta aag ttt tta aaa gag cga aag att tac gaa ctc ata agg gaa       972
Glu Val Lys Phe Leu Lys Glu Arg Lys Ile Tyr Glu Leu Ile Arg Glu
        290                 295                 300 ctc tct tcc aga aaa cac aca atc ctt gag ata cct aca ctt aat cag      1020
Leu Ser Ser Arg Lys His Thr Ile Leu Glu Ile Pro Thr Leu Asn Gln
305                 310                 315                 320 aaa acc gaa agt tat aaa ccg aca tac gag gtt ata ggt caa cta aac      1068
Lys Thr Glu Ser Tyr Lys Pro Thr Tyr Glu Val Ile Gly Gln Leu Asn
                325                 330                 335 gaa acc ttt att ctc gta agc gac ggg aac ttt tta tac ttc ata gac      1116
Glu Thr Phe Ile Leu Val Ser Asp Gly Asn Phe Leu Tyr Phe Ile Asp
                340                 345                 350 cag cac ctt ctt gat gag aga ata aac tac gag aaa aat gga aac gaa      1164
Gln His Leu Leu Asp Glu Arg Ile Asn Tyr Glu Lys Asn Gly Asn Glu
                355                 360                 365 gaa ctt gcc tgc aga att tcc gta aaa gcg ggg gaa aaa tta aca aac      1212
Glu Leu Ala Cys Arg Ile Ser Val Lys Ala Gly Glu Lys Leu Thr Asn
        370                 375                 380 gaa aag ata aaa gaa ctc ata aag gaa tgg aaa aag ctt gaa aac ccc      1260
Glu Lys Ile Lys Glu Leu Ile Lys Glu Trp Lys Lys Leu Glu Asn Pro
385                 390                 395                 400 cac gta tgt ccc cac ggc aga cct ata tac tac aaa ctc ccc tta aag      1308
His Val Cys Pro His Gly Arg Pro Ile Tyr Tyr Lys Leu Pro Leu Lys
                405                 410                 415 gaa gta tac gaa aag ctc gga agg agt ttt taaggtaaaa ttctatagac        1358
Glu Val Tyr Glu Lys Leu Gly Arg Ser Phe
```

```
Glu Val Tyr Glu Lys Leu Gly Arg Ser Phe
            420                 425 ccaatgttca gcattaagtt ct                                          1380

<210> SEQ ID NO 40
<211> LENGTH: 426
<212> TYPE: PRT
<213> ORGANISM: Aquifex pyrophilus

<400> SEQUENCE: 40

Met Phe Val Lys Ile Leu Pro Pro Glu Val Arg Arg Lys Ile Ala Ala
  1               5                  10                  15

Gly Glu Val Ile Asp Ala Pro Val Asp Val Lys Glu Leu Ile Glu
             20                  25                  30

Asn Ser Leu Asp Ala Lys Ala Thr Arg Ile Glu Ile Glu Val Val Lys
             35                  40                  45

Gly Gly Lys Arg Leu Ile Arg Val Lys Asp Asn Gly Ile Gly Ile His
 50                  55                  60

Pro Glu Asp Ile Glu Lys Val Val Leu Ser Gly Ala Thr Ser Lys Ile
 65                  70                  75                  80

Glu Lys Glu Thr Asp Leu Leu Asn Val Glu Thr Tyr Gly Phe Arg Gly
             85                  90                  95

Glu Ala Leu Tyr Ser Ile Ser Ser Val Ser Lys Phe Arg Leu Arg Ser
            100                 105                 110

Arg Phe Tyr Gln Glu Lys Glu Gly Arg Glu Ile Glu Val Glu Gly Gly
            115                 120                 125

Thr Leu Lys Ser Val Arg Arg Val Gly Met Glu Val Gly Thr Glu Val
130                 135                 140

Glu Val Tyr Asp Leu Phe Phe Asn Leu Pro Ala Arg Lys Lys Phe Leu
145                 150                 155                 160

Arg Lys Glu Asp Thr Glu Arg Arg Lys Ile Thr Glu Leu Val Lys Glu
                165                 170                 175

Tyr Ala Ile Thr Asn Pro Gln Val Asp Phe His Leu Phe Ser Glu Gly
                180                 185                 190

Lys Glu Thr Leu Asn Leu Lys Lys Lys Asp Leu Lys Gly Arg Ile Glu
                195                 200                 205

Glu Ile Phe Glu Ser Ile Phe Glu Glu Ser Ser Glu Arg Glu Gly
            210                 215                 220

Ile Lys Val Arg Ala Phe Ile Ser Arg Asn Gln Lys Arg Gly Lys Tyr
225                 230                 235                 240

Tyr Leu Phe Val Asn Ser Arg Pro Val Tyr Asn Lys Asn Leu Lys Glu
                245                 250                 255

Tyr Leu Lys Lys Thr Phe Gly Tyr Lys Thr Ile Val Val Leu Phe Ile
                260                 265                 270

Asp Ile Pro Pro Phe Leu Val Asp Phe Asn Val His Pro Lys Lys Lys
            275                 280                 285

Glu Val Lys Phe Leu Lys Glu Arg Lys Ile Tyr Glu Leu Ile Arg Glu
            290                 295                 300

Leu Ser Ser Arg Lys His Thr Ile Leu Glu Ile Pro Thr Leu Asn Gln
305                 310                 315                 320

Lys Thr Glu Ser Tyr Lys Pro Thr Tyr Glu Val Ile Gly Gln Leu Asn
                325                 330                 335

Glu Thr Phe Ile Leu Val Ser Asp Gly Asn Phe Leu Tyr Phe Ile Asp
            340                 345                 350
```

```
Gln His Leu Leu Asp Glu Arg Ile Asn Tyr Glu Lys Asn Gly Asn Glu
        355                 360                 365

Glu Leu Ala Cys Arg Ile Ser Val Lys Ala Gly Glu Lys Leu Thr Asn
        370                 375                 380

Glu Lys Ile Lys Glu Leu Ile Lys Glu Trp Lys Lys Leu Glu Asn Pro
385                 390                 395                 400

His Val Cys Pro His Gly Arg Pro Ile Tyr Tyr Lys Leu Pro Leu Lys
                405                 410                 415

Glu Val Tyr Glu Lys Leu Gly Arg Ser Phe
        420                 425

<210> SEQ ID NO 41
<211> LENGTH: 1640
<212> TYPE: DNA
<213> ORGANISM: Thermotoga maritima
<220> FEATURE:
<221> NAME/KEY: CDS
<222> LOCATION: (51)...(1583)

<400> SEQUENCE: 41
```

| | | |
|---|---|---|
| tttttctgg atgttaaaat tttcagggag atcgagtgga gaggtgttct gtt ttg<br>                                                                                                                         Val Leu<br>                                                                                                                                                    1 | | 56 |

```
aga ata aaa aga ctt ccc gag agc ctc gtc aga aaa atc gcc gcg ggt      104
Arg Ile Lys Arg Leu Pro Glu Ser Leu Val Arg Lys Ile Ala Ala Gly
        5                   10                  15 gag gtg att cac aat cca tct ttc gtt ctg aaa gag ctt gta gaa aac      152
Glu Val Ile His Asn Pro Ser Phe Val Leu Lys Glu Leu Val Glu Asn
    20                  25                  30 agt ctg gac gcg cag gcc gac agg ata gtt gtt gag ata gaa aac ggt      200
Ser Leu Asp Ala Gln Ala Asp Arg Ile Val Val Glu Ile Glu Asn Gly
 35                  40                  45                  50 gga aag aac atg gta aga gta tcc gac aat gga atc ggg atg acc aga      248
Gly Lys Asn Met Val Arg Val Ser Asp Asn Gly Ile Gly Met Thr Arg
                 55                  60                  65 gaa gag gca ctt ctg gca ata gaa cct tac acg acg agc aag ata gag      296
Glu Glu Ala Leu Leu Ala Ile Glu Pro Tyr Thr Thr Ser Lys Ile Glu
         70                  75                  80 agc gag gaa gat ctg cac agg atc aga act tac ggt ttc aga ggt gaa      344
Ser Glu Glu Asp Leu His Arg Ile Arg Thr Tyr Gly Phe Arg Gly Glu
     85                  90                  95 gcg ctt gct tcg att gtg cag gtc agc aga gcc aag atc gtg aca aaa      392
Ala Leu Ala Ser Ile Val Gln Val Ser Arg Ala Lys Ile Val Thr Lys
100                 105                 110 acg gaa aaa gac gca ctc gca aca cag ttg atg att gct ggg ggg aaa      440
Thr Glu Lys Asp Ala Leu Ala Thr Gln Leu Met Ile Ala Gly Gly Lys
115                 120                 125                 130 gtg gaa gaa atc tcg gaa acc cac agg gat acc ggc acc acc gtt gag      488
Val Glu Glu Ile Ser Glu Thr His Arg Asp Thr Gly Thr Thr Val Glu
                135                 140                 145 gtg aga gat ctc ttc ttc aac cta ccc gtc cgg aga aaa tct ctg aag      536
Val Arg Asp Leu Phe Phe Asn Leu Pro Val Arg Arg Lys Ser Leu Lys
            150                 155                 160 tcc tct gcc atc gag ttg aga atg tgt cgt gag atg ttt gaa aga ttc      584
Ser Ser Ala Ile Glu Leu Arg Met Cys Arg Glu Met Phe Glu Arg Phe
                165                 170                 175 gtc ctt gta cga aac gac gtt gat ttt gta ttc acc tca gat gga aag      632
Val Leu Val Arg Asn Asp Val Asp Phe Val Phe Thr Ser Asp Gly Lys
            180                 185                 190 ata gtc cat tcc ttt cca aga aca cag aac atc ttt gaa aga gct ctc      680
```

```
                                                        -continued

Ile Val His Ser Phe Pro Arg Thr Gln Asn Ile Phe Glu Arg Ala Leu
195                 200                 205                 210 ctg atc ctt gaa gat ctg aga aaa ggt tac atc acg ttc gaa gag gaa           728
Leu Ile Leu Glu Asp Leu Arg Lys Gly Tyr Ile Thr Phe Glu Glu Glu
                215                 220                 225 tta tcc ggc ctg agg ata aag gga ata gtt tca tcc cgc gag gtg aca           776
Leu Ser Gly Leu Arg Ile Lys Gly Ile Val Ser Ser Arg Glu Val Thr
    230                 235                 240 aga tcc agc aga acg gga gag tat ttc tac gtg aac ggt cgt ttt gtg           824
Arg Ser Ser Arg Thr Gly Glu Tyr Phe Tyr Val Asn Gly Arg Phe Val
245                 250                 255 gtt tcc gaa gaa ctc cac gaa gta ctc atg aaa gtt tac gat ctt cca           872
Val Ser Glu Glu Leu His Glu Val Leu Met Lys Val Tyr Asp Leu Pro
        260                 265                 270 aag aga agc tat ccc gtc gcg gtt ctt ttc ata gag gta aat ccg gaa           920
Lys Arg Ser Tyr Pro Val Ala Val Leu Phe Ile Glu Val Asn Pro Glu
275                 280                 285                 290 gaa ctc gac gtg aac ata cac cct tcg aaa atc gtg gtg aaa ttt ctc           968
Glu Leu Asp Val Asn Ile His Pro Ser Lys Ile Val Val Lys Phe Leu
                295                 300                 305 aac gaa gaa aag gtg aaa aag agt ttg gaa gaa acc ctc aaa aga aat          1016
Asn Glu Glu Lys Val Lys Lys Ser Leu Glu Glu Thr Leu Lys Arg Asn
            310                 315                 320 ctg gca cgg aaa tgg tac agg tcg gtt gcg tac gaa gaa ata tcc tcc          1064
Leu Ala Arg Lys Trp Tyr Arg Ser Val Ala Tyr Glu Glu Ile Ser Ser
            325                 330                 335 cgt gcg ctg agc gtg gca gaa gca cca tcc cac aga tgg ttt ttg gtc          1112
Arg Ala Leu Ser Val Ala Glu Ala Pro Ser His Arg Trp Phe Leu Val
        340                 345                 350 aag ggt aag tac gct gtc gtt gaa gtg gaa gat ggt ttg ctc ttt gtg          1160
Lys Gly Lys Tyr Ala Val Val Glu Val Glu Asp Gly Leu Leu Phe Val
355                 360                 365                 370 gat ctt cat gct ctc cac gaa cga acg att tac gaa gaa atc ctt tcg          1208
Asp Leu His Ala Leu His Glu Arg Thr Ile Tyr Glu Glu Ile Leu Ser
                375                 380                 385 aaa aaa agc tgg ggg aaa aga cgg gtg aaa agg aac ata aca gtt gtg          1256
Lys Lys Ser Trp Gly Lys Arg Arg Val Lys Arg Asn Ile Thr Val Val
            390                 395                 400 cta tca agg gaa gaa aaa caa aaa ctg gaa gaa tac gga ttc tcc ttt          1304
Leu Ser Arg Glu Glu Lys Gln Lys Leu Glu Glu Tyr Gly Phe Ser Phe
        405                 410                 415 caa gga gaa gaa gga gct ttg aaa gtc att gaa atc cct gag ttc ctc          1352
Gln Gly Glu Glu Gly Ala Leu Lys Val Ile Glu Ile Pro Glu Phe Leu
    420                 425                 430 acc gaa gac gtt gtg gag gaa ttt ttc agg gac ttc cca gtt gat gaa          1400
Thr Glu Asp Val Val Glu Glu Phe Phe Arg Asp Phe Pro Val Asp Glu
435                 440                 445                 450 aaa ctg aag gaa aga ata gcc ctt gcc gct tgt aaa ctt gcc act aaa          1448
Lys Leu Lys Glu Arg Ile Ala Leu Ala Ala Cys Lys Leu Ala Thr Lys
                455                 460                 465 tcc gga gaa ttc gac gaa gag atc gca tcg aaa ctg ctg gat gtc ttt          1496
Ser Gly Glu Phe Asp Glu Glu Ile Ala Ser Lys Leu Leu Asp Val Phe
            470                 475                 480 ttc aag aag cgg ttt gaa aga tgt cct cac gga agg ccg att tct ttc          1544
Phe Lys Lys Arg Phe Glu Arg Cys Pro His Gly Arg Pro Ile Ser Phe
            485                 490                 495 aag atc agc tat gag gac atg gac cga ttt ttc gag cgt taacccattt          1593
Lys Ile Ser Tyr Glu Asp Met Asp Arg Phe Phe Glu Arg
500                 505                 510
```

-continued

```
tcaccacgtt gacgtcagcg gtgaaaacca ggccatcgaa gtctatg            1640
```

<210> SEQ ID NO 42
<211> LENGTH: 511
<212> TYPE: PRT
<213> ORGANISM: Thermotoga maritima

<400> SEQUENCE: 42

| | | | | | | | | | | | | | | |
|---|---|---|---|---|---|---|---|---|---|---|---|---|---|---|
| Val | Leu | Arg | Ile | Lys | Arg | Leu | Pro | Glu | Ser | Leu | Val | Arg | Lys | Ile | Ala |
| 1 | | | | 5 | | | | | 10 | | | | | 15 | |
| Ala | Gly | Glu | Val | Ile | His | Asn | Pro | Ser | Phe | Val | Leu | Lys | Glu | Leu | Val |
| | | | 20 | | | | | 25 | | | | | 30 | | |
| Glu | Asn | Ser | Leu | Asp | Ala | Gln | Ala | Asp | Arg | Ile | Val | Val | Glu | Ile | Glu |
| | | 35 | | | | 40 | | | | | 45 | | | | |
| Asn | Gly | Gly | Lys | Asn | Met | Val | Arg | Val | Ser | Asp | Asn | Gly | Ile | Gly | Met |
| | 50 | | | | | 55 | | | | | 60 | | | | |
| Thr | Arg | Glu | Glu | Ala | Leu | Leu | Ala | Ile | Glu | Pro | Tyr | Thr | Thr | Ser | Lys |
| 65 | | | | | 70 | | | | | 75 | | | | | 80 |
| Ile | Glu | Ser | Glu | Glu | Asp | Leu | His | Arg | Ile | Arg | Thr | Tyr | Gly | Phe | Arg |
| | | | | 85 | | | | | 90 | | | | | 95 | |
| Gly | Glu | Ala | Leu | Ala | Ser | Ile | Val | Gln | Val | Ser | Arg | Ala | Lys | Ile | Val |
| | | | 100 | | | | | 105 | | | | | 110 | | |
| Thr | Lys | Thr | Glu | Lys | Asp | Ala | Leu | Ala | Thr | Gln | Leu | Met | Ile | Ala | Gly |
| | | 115 | | | | 120 | | | | | 125 | | | | |
| Gly | Lys | Val | Glu | Glu | Ile | Ser | Glu | Thr | His | Arg | Asp | Thr | Gly | Thr | Thr |
| | 130 | | | | | 135 | | | | | 140 | | | | |
| Val | Glu | Val | Arg | Asp | Leu | Phe | Phe | Asn | Leu | Pro | Val | Arg | Arg | Lys | Ser |
| 145 | | | | | 150 | | | | | 155 | | | | | 160 |
| Leu | Lys | Ser | Ser | Ala | Ile | Glu | Leu | Arg | Met | Cys | Arg | Glu | Met | Phe | Glu |
| | | | | 165 | | | | | 170 | | | | | 175 | |
| Arg | Phe | Val | Leu | Val | Arg | Asn | Asp | Val | Asp | Phe | Val | Phe | Thr | Ser | Asp |
| | | | 180 | | | | | 185 | | | | | 190 | | |
| Gly | Lys | Ile | Val | His | Ser | Phe | Pro | Arg | Thr | Gln | Asn | Ile | Phe | Glu | Arg |
| | | 195 | | | | 200 | | | | | 205 | | | | |
| Ala | Leu | Leu | Ile | Leu | Glu | Asp | Leu | Arg | Lys | Gly | Tyr | Ile | Thr | Phe | Glu |
| | 210 | | | | | 215 | | | | | 220 | | | | |
| Glu | Glu | Leu | Ser | Gly | Leu | Arg | Ile | Lys | Gly | Ile | Val | Ser | Ser | Arg | Glu |
| 225 | | | | | 230 | | | | | 235 | | | | | 240 |
| Val | Thr | Arg | Ser | Ser | Arg | Thr | Gly | Glu | Tyr | Phe | Tyr | Val | Asn | Gly | Arg |
| | | | | 245 | | | | | 250 | | | | | 255 | |
| Phe | Val | Val | Ser | Glu | Glu | Leu | His | Glu | Val | Leu | Met | Lys | Val | Tyr | Asp |
| | | | 260 | | | | | 265 | | | | | 270 | | |
| Leu | Pro | Lys | Arg | Ser | Tyr | Pro | Val | Ala | Val | Leu | Phe | Ile | Glu | Val | Asn |
| | | 275 | | | | 280 | | | | | 285 | | | | |
| Pro | Glu | Glu | Leu | Asp | Val | Asn | Ile | His | Pro | Ser | Lys | Ile | Val | Val | Lys |
| | 290 | | | | | 295 | | | | | 300 | | | | |
| Phe | Leu | Asn | Glu | Glu | Lys | Val | Lys | Ser | Leu | Glu | Glu | Thr | Leu | Lys |
| 305 | | | | | 310 | | | | | 315 | | | | | 320 |
| Arg | Asn | Leu | Ala | Arg | Lys | Trp | Tyr | Arg | Ser | Val | Ala | Tyr | Glu | Glu | Ile |
| | | | | 325 | | | | | 330 | | | | | 335 | |
| Ser | Ser | Arg | Ala | Leu | Ser | Val | Ala | Glu | Ala | Pro | Ser | His | Arg | Trp | Phe |
| | | | 340 | | | | | 345 | | | | | 350 | | |
| Leu | Val | Lys | Gly | Lys | Tyr | Ala | Val | Val | Glu | Val | Glu | Asp | Gly | Leu | Leu |
| | | 355 | | | | 360 | | | | | 365 | | | | |

```
Phe Val Asp Leu His Ala Leu His Glu Arg Thr Ile Tyr Glu Glu Ile
        370                 375                 380

Leu Ser Lys Lys Ser Trp Gly Lys Arg Arg Val Lys Arg Asn Ile Thr
385                 390                 395                 400

Val Val Leu Ser Arg Glu Lys Gln Lys Leu Glu Tyr Gly Phe
                405                 410                 415

Ser Phe Gln Gly Glu Gly Ala Leu Lys Val Ile Glu Ile Pro Glu
                420                 425                 430

Phe Leu Thr Glu Asp Val Val Glu Glu Phe Phe Arg Asp Phe Pro Val
            435                 440                 445

Asp Glu Lys Leu Lys Glu Arg Ile Ala Leu Ala Ala Cys Lys Leu Ala
            450                 455                 460

Thr Lys Ser Gly Glu Phe Asp Glu Glu Ile Ala Ser Lys Leu Leu Asp
465                 470                 475                 480

Val Phe Phe Lys Lys Arg Phe Glu Arg Cys Pro His Gly Arg Pro Ile
                485                 490                 495

Ser Phe Lys Ile Ser Tyr Glu Asp Met Asp Arg Phe Phe Glu Arg
                500                 505                 510

<210> SEQ ID NO 43
<211> LENGTH: 649
<212> TYPE: PRT
<213> ORGANISM: Streptococcus pneumoniae

<400> SEQUENCE: 43

Met Ser His Ile Ile Glu Leu Pro Glu Met Leu Ala Asn Gln Ile Ala
1               5                   10                  15

Ala Gly Glu Val Ile Glu Arg Pro Ala Ser Val Cys Lys Glu Leu Val
                20                  25                  30

Glu Asn Ala Ile Asp Ala Gly Ser Ser Gln Ile Ile Glu Ile Glu
            35                  40                  45

Glu Ala Gly Leu Lys Lys Val Gln Ile Thr Asp Asn Gly His Gly Ile
    50                  55                  60

Ala His Asp Glu Val Glu Leu Ala Leu Arg Arg His Ala Thr Ser Lys
65                  70                  75                  80

Ile Lys Asn Gln Ala Asp Leu Phe Arg Ile Arg Thr Leu Gly Phe Arg
                85                  90                  95

Gly Glu Ala Leu Pro Ser Ile Ala Ser Val Ser Val Leu Thr Leu Leu
                100                 105                 110

Thr Ala Val Asp Gly Ala Ser His Gly Thr Lys Leu Val Ala Arg Gly
            115                 120                 125

Gly Glu Val Glu Glu Val Ile Pro Ala Thr Ser Pro Val Gly Thr Lys
    130                 135                 140

Val Cys Val Glu Asp Leu Phe Phe Asn Thr Pro Ala Arg Leu Lys Tyr
145                 150                 155                 160

Met Lys Ser Gln Gln Ala Glu Leu Ser His Ile Ile Asp Ile Val Asn
                165                 170                 175

Arg Leu Gly Leu Ala His Pro Glu Ile Ser Phe Ser Leu Ile Ser Asp
                180                 185                 190

Gly Lys Glu Met Thr Arg Thr Ala Gly Thr Gly Gln Leu Arg Gln Ala
            195                 200                 205

Ile Ala Gly Ile Tyr Gly Leu Val Ser Ala Lys Lys Met Ile Glu Ile
    210                 215                 220

Glu Asn Ser Asp Leu Asp Phe Glu Ile Ser Gly Phe Val Ser Leu Pro
225                 230                 235                 240
```

```
Glu Leu Thr Arg Ala Asn Arg Asn Tyr Ile Ser Leu Phe Ile Asn Gly
                245                 250                 255
Arg Tyr Ile Lys Asn Phe Leu Leu Asn Arg Ala Ile Leu Asp Gly Phe
                260                 265                 270
Gly Ser Lys Leu Met Val Gly Arg Phe Pro Leu Ala Val Ile His Ile
                275                 280                 285
His Ile Asp Pro Tyr Leu Ala Asp Val Asn Val His Pro Thr Lys Gln
                290                 295                 300
Glu Val Arg Ile Ser Lys Glu Lys Glu Leu Met Thr Leu Val Ser Glu
305                 310                 315                 320
Ala Ile Ala Asn Ser Leu Lys Glu Gln Thr Leu Ile Pro Asp Ala Leu
                325                 330                 335
Glu Asn Leu Ala Lys Ser Thr Val Arg Asn Arg Glu Lys Val Glu Gln
                340                 345                 350
Thr Ile Leu Pro Leu Lys Glu Asn Thr Leu Tyr Tyr Glu Lys Thr Glu
                355                 360                 365
Pro Ser Arg Pro Ser Gln Thr Glu Val Ala Asp Tyr Gln Val Glu Leu
                370                 375                 380
Thr Asp Glu Gly Gln Asp Leu Thr Leu Phe Ala Lys Glu Thr Leu Asp
385                 390                 395                 400
Arg Leu Thr Lys Pro Ala Lys Leu His Phe Ala Glu Arg Lys Pro Ala
                405                 410                 415
Asn Tyr Asp Gln Leu Asp His Pro Glu Leu Asp Leu Ala Ser Ile Asp
                420                 425                 430
Lys Ala Tyr Asp Lys Leu Glu Arg Glu Glu Ala Ser Ser Phe Pro Glu
                435                 440                 445
Leu Glu Phe Phe Gly Gln Met His Gly Thr Tyr Leu Phe Ala Gln Gly
                450                 455                 460
Arg Asp Gly Leu Tyr Ile Ile Asp Gln His Ala Ala Gln Glu Arg Val
465                 470                 475                 480
Lys Tyr Glu Glu Tyr Arg Glu Ser Ile Gly Asn Val Asp Gln Ser Gln
                485                 490                 495
Gln Gln Leu Leu Val Pro Tyr Ile Phe Glu Phe Pro Ala Asp Asp Ala
                500                 505                 510
Leu Arg Leu Lys Glu Arg Met Pro Leu Leu Glu Glu Val Gly Val Phe
                515                 520                 525
Leu Ala Glu Tyr Gly Glu Asn Gln Phe Ile Leu Arg Glu His Pro Ile
                530                 535                 540
Trp Met Ala Glu Glu Glu Ile Glu Ser Gly Ile Tyr Glu Met Cys Asp
545                 550                 555                 560
Met Leu Leu Leu Thr Lys Glu Val Ser Ile Lys Lys Tyr Arg Ala Glu
                565                 570                 575
Leu Ala Ile Met Met Ser Cys Lys Arg Ser Ile Lys Ala Asn His Arg
                580                 585                 590
Ile Asp Asp His Ser Ala Arg Gln Leu Leu Tyr Gln Leu Ser Gln Cys
                595                 600                 605
Asp Asn Pro Tyr Asn Cys Pro His Gly Arg Pro Val Leu Val His Phe
                610                 615                 620
Thr Lys Ser Asp Met Glu Lys Met Phe Arg Arg Ile Gln Glu Asn His
625                 630                 635                 640
Thr Ser Leu Arg Glu Leu Gly Lys Tyr
                645
```

-continued

```
<210> SEQ ID NO 44
<211> LENGTH: 615
<212> TYPE: PRT
<213> ORGANISM: Escherichia coli

<400> SEQUENCE: 44
```

| Met | Pro | Ile | Gln | Val | Leu | Pro | Pro | Gln | Leu | Ala | Asn | Gln | Ile | Ala | Ala |
|---|---|---|---|---|---|---|---|---|---|---|---|---|---|---|---|
| 1 | | | | 5 | | | | | 10 | | | | | 15 | |

| Gly | Glu | Val | Val | Glu | Arg | Pro | Ala | Ser | Val | Val | Lys | Glu | Leu | Val | Glu |
|---|---|---|---|---|---|---|---|---|---|---|---|---|---|---|---|
| | | | 20 | | | | | 25 | | | | | 30 | | |

| Asn | Ser | Leu | Asp | Ala | Gly | Ala | Thr | Arg | Ile | Asp | Ile | Asp | Ile | Glu | Arg |
|---|---|---|---|---|---|---|---|---|---|---|---|---|---|---|---|
| | | 35 | | | | | 40 | | | | | 45 | | | |

| Gly | Gly | Ala | Lys | Leu | Ile | Arg | Ile | Arg | Asp | Asn | Gly | Cys | Gly | Ile | Lys |
|---|---|---|---|---|---|---|---|---|---|---|---|---|---|---|---|
| | 50 | | | | | 55 | | | | | 60 | | | | |

| Lys | Asp | Glu | Leu | Ala | Leu | Ala | Leu | Ala | Arg | His | Ala | Thr | Ser | Lys | Ile |
|---|---|---|---|---|---|---|---|---|---|---|---|---|---|---|---|
| 65 | | | | | 70 | | | | | 75 | | | | | 80 |

| Ala | Ser | Leu | Asp | Asp | Leu | Glu | Ala | Ile | Ile | Ser | Leu | Gly | Phe | Arg | Gly |
|---|---|---|---|---|---|---|---|---|---|---|---|---|---|---|---|
| | | | | 85 | | | | | 90 | | | | | 95 | |

| Glu | Ala | Leu | Ala | Ser | Ile | Ser | Ser | Val | Ser | Arg | Leu | Thr | Leu | Thr | Ser |
|---|---|---|---|---|---|---|---|---|---|---|---|---|---|---|---|
| | | | | 100 | | | | | 105 | | | | | 110 | |

| Arg | Thr | Ala | Glu | Gln | Gln | Glu | Ala | Trp | Gln | Ala | Tyr | Ala | Glu | Gly | Arg |
|---|---|---|---|---|---|---|---|---|---|---|---|---|---|---|---|
| | | | 115 | | | | | 120 | | | | | 125 | | |

| Asp | Met | Asn | Val | Thr | Val | Lys | Pro | Ala | Ala | His | Pro | Val | Gly | Thr | Thr |
|---|---|---|---|---|---|---|---|---|---|---|---|---|---|---|---|
| | 130 | | | | | 135 | | | | | 140 | | | | |

| Leu | Glu | Val | Leu | Asp | Leu | Phe | Tyr | Asn | Thr | Pro | Ala | Arg | Arg | Lys | Phe |
|---|---|---|---|---|---|---|---|---|---|---|---|---|---|---|---|
| 145 | | | | | 150 | | | | | 155 | | | | | 160 |

| Leu | Arg | Thr | Glu | Lys | Thr | Glu | Phe | Asn | His | Ile | Asp | Glu | Ile | Ile | Arg |
|---|---|---|---|---|---|---|---|---|---|---|---|---|---|---|---|
| | | | | 165 | | | | | 170 | | | | | 175 | |

| Arg | Ile | Ala | Leu | Ala | Arg | Phe | Asp | Val | Thr | Ile | Asn | Leu | Ser | His | Asn |
|---|---|---|---|---|---|---|---|---|---|---|---|---|---|---|---|
| | | | | 180 | | | | | 185 | | | | | 190 | |

| Gly | Lys | Ile | Val | Arg | Gln | Tyr | Arg | Ala | Val | Pro | Glu | Gly | Gly | Gln | Lys |
|---|---|---|---|---|---|---|---|---|---|---|---|---|---|---|---|
| | | | 195 | | | | | 200 | | | | | 205 | | |

| Glu | Arg | Arg | Leu | Gly | Ala | Ile | Cys | Gly | Thr | Ala | Phe | Leu | Glu | Gln | Ala |
|---|---|---|---|---|---|---|---|---|---|---|---|---|---|---|---|
| | 210 | | | | | 215 | | | | | 220 | | | | |

| Leu | Ala | Ile | Glu | Trp | Gln | His | Gly | Asp | Leu | Thr | Leu | Arg | Gly | Trp | Val |
|---|---|---|---|---|---|---|---|---|---|---|---|---|---|---|---|
| 225 | | | | | 230 | | | | | 235 | | | | | 240 |

| Ala | Asp | Pro | Asn | His | Thr | Thr | Pro | Ala | Leu | Ala | Glu | Ile | Gln | Tyr | Cys |
|---|---|---|---|---|---|---|---|---|---|---|---|---|---|---|---|
| | | | | 245 | | | | | 250 | | | | | 255 | |

| Tyr | Val | Asn | Gly | Arg | Met | Met | Arg | Asp | Arg | Leu | Ile | Asn | His | Ala | Ile |
|---|---|---|---|---|---|---|---|---|---|---|---|---|---|---|---|
| | | | 260 | | | | | 265 | | | | | 270 | | |

| Arg | Gln | Ala | Cys | Glu | Asp | Lys | Leu | Gly | Ala | Asp | Gln | Gln | Pro | Ala | Phe |
|---|---|---|---|---|---|---|---|---|---|---|---|---|---|---|---|
| | | 275 | | | | | 280 | | | | | 285 | | | |

| Val | Leu | Tyr | Leu | Glu | Ile | Asp | Pro | His | Gln | Val | Asp | Val | Asn | Val | His |
|---|---|---|---|---|---|---|---|---|---|---|---|---|---|---|---|
| | 290 | | | | | 295 | | | | | 300 | | | | |

| Pro | Ala | Lys | His | Glu | Val | Arg | Phe | His | Gln | Ser | Arg | Leu | Val | His | Asp |
|---|---|---|---|---|---|---|---|---|---|---|---|---|---|---|---|
| 305 | | | | | 310 | | | | | 315 | | | | | 320 |

| Phe | Ile | Tyr | Gln | Gly | Val | Leu | Ser | Val | Leu | Gln | Gln | Gln | Leu | Glu | Thr |
|---|---|---|---|---|---|---|---|---|---|---|---|---|---|---|---|
| | | | | 325 | | | | | 330 | | | | | 335 | |

| Pro | Leu | Pro | Leu | Asp | Asp | Glu | Pro | Gln | Pro | Ala | Pro | Arg | Ser | Ile | Pro |
|---|---|---|---|---|---|---|---|---|---|---|---|---|---|---|---|
| | | | 340 | | | | | 345 | | | | | 350 | | |

| Glu | Asn | Arg | Val | Ala | Ala | Gly | Arg | Asn | His | Phe | Ala | Glu | Pro | Ala | Ala |
|---|---|---|---|---|---|---|---|---|---|---|---|---|---|---|---|
| | | 355 | | | | | 360 | | | | | 365 | | | |

| Arg | Glu | Pro | Val | Ala | Pro | Arg | Tyr | Thr | Pro | Ala | Pro | Ala | Ser | Gly | Ser |
|---|---|---|---|---|---|---|---|---|---|---|---|---|---|---|---|
| 370 | | | | 375 | | | | | 380 | | | | | | |

Arg Pro Ala Ala Pro Trp Pro Asn Ala Gln Pro Gly Tyr Gln Lys Gln
385                 390                 395                 400

Gln Gly Glu Val Tyr Arg Gln Leu Leu Gln Thr Pro Ala Pro Met Gln
            405                 410                 415

Lys Leu Lys Ala Pro Glu Pro Gln Glu Pro Ala Leu Ala Ala Asn Ser
        420                 425                 430

Gln Ser Phe Gly Arg Val Leu Thr Ile Val His Ser Asp Cys Ala Leu
    435                 440                 445

Leu Glu Arg Asp Gly Asn Ile Ser Leu Leu Ser Leu Pro Val Ala Glu
    450                 455                 460

Arg Trp Leu Arg Gln Ala Gln Leu Thr Pro Gly Glu Ala Pro Val Cys
465                 470                 475                 480

Ala Gln Pro Leu Leu Ile Pro Leu Arg Leu Lys Val Ser Ala Glu Glu
            485                 490                 495

Lys Ser Ala Leu Glu Lys Ala Gln Ser Ala Leu Ala Glu Leu Gly Ile
        500                 505                 510

Asp Phe Gln Ser Asp Ala Gln His Val Thr Ile Arg Ala Val Pro Leu
    515                 520                 525

Pro Leu Arg Gln Gln Asn Leu Gln Ile Leu Ile Pro Glu Leu Ile Gly
    530                 535                 540

Tyr Leu Ala Lys Gln Ser Val Phe Glu Pro Gly Asn Ile Ala Gln Trp
545                 550                 555                 560

Ile Ala Arg Asn Leu Met Ser Glu His Ala Gln Trp Ser Met Ala Gln
            565                 570                 575

Ala Ile Thr Leu Leu Ala Asp Val Glu Arg Leu Cys Pro Gln Leu Val
        580                 585                 590

Lys Thr Pro Pro Gly Gly Leu Leu Gln Ser Val Asp Leu His Pro Ala
    595                 600                 605

Ile Lys Ala Leu Lys Asp Glu
    610                 615

<210> SEQ ID NO 45
<211> LENGTH: 396
<212> TYPE: DNA
<213> ORGANISM: Thermus thermophilus

<400> SEQUENCE: 45
gaattcgatc acctgcaaga agtcatcaag cgcctggccc tggcccgttt cgacgtggcc        60
tttcacctgc gccacaatgg caagaccatc ctcagcctgc acgaagccaa cgacgacgcc       120
gcccgtgctc ggcgggtggc ggcggtgtgt ggcagcgggt tcctggagca ggcgctgccg       180
attgagatcg agcgcaatgg cttgaggttg tggggctggg tcgggttgcc gacgttctcc       240
cgcagccagg ccgatttgca gtatttcttt gtgaacggcc gggcggtccg cgacaaactg       300
gtggcccatg cggtgcgcca ggcttatcgc gatgtgctgt tcaacgggcg acacccgact       360
tttgtgctgt tctttgaggt tgacccttcg gtggtc                                 396

<210> SEQ ID NO 46
<211> LENGTH: 150
<212> TYPE: PRT
<213> ORGANISM: Escherichia coli

<400> SEQUENCE: 46

Leu Phe Tyr Asn Thr Pro Ala Arg Arg Lys Phe Leu Arg Thr Glu Lys
1               5                   10                  15

```
Thr Glu Phe Asn His Ile Asp Glu Ile Ile Arg Arg Ile Ala Leu Ala
            20                  25                  30

Arg Phe Asp Val Thr Ile Asn Leu Ser His Asn Gly Lys Ile Val Arg
        35                  40                  45

Gln Tyr Arg Ala Val Pro Glu Gly Gln Lys Glu Arg Arg Leu Gly
50                      55                  60

Ala Ile Cys Gly Thr Ala Phe Leu Glu Gln Ala Leu Ala Ile Glu Trp
65                  70                  75                  80

Gln His Gly Asp Leu Thr Leu Arg Gly Trp Val Ala Asp Pro Asn His
                85                  90                  95

Thr Thr Pro Ala Leu Ala Glu Ile Gln Tyr Cys Tyr Val Asn Gly Arg
                100                 105                 110

Met Met Arg Asp Arg Leu Ile Asn His Ala Ile Arg Gln Ala Cys Glu
                115                 120                 125

Asp Lys Leu Gly Ala Asp Gln Gln Pro Ala Phe Val Leu Tyr Leu Glu
                130                 135                 140

Ile Asp Pro His Gln Val
145                 150

<210> SEQ ID NO 47
<211> LENGTH: 132
<212> TYPE: PRT
<213> ORGANISM: Thermus thermophilus

<400> SEQUENCE: 47

Glu Phe Asp His Leu Gln Glu Val Ile Lys Arg Leu Ala Leu Ala Arg
1               5                   10                  15

Phe Asp Val Ala Phe His Leu Arg His Asn Gly Lys Thr Ile Leu Ser
            20                  25                  30

Leu His Glu Ala Asn Asp Asp Ala Ala Arg Ala Arg Val Ala Ala
        35                  40                  45

Val Cys Gly Ser Gly Phe Leu Glu Gln Ala Leu Pro Ile Glu Ile Glu
50                  55                  60

Arg Asn Gly Leu Arg Leu Trp Gly Trp Val Gly Leu Pro Thr Phe Ser
65                  70                  75                  80

Arg Ser Gln Ala Asp Leu Gln Tyr Phe Phe Val Asn Gly Arg Ala Val
                85                  90                  95

Arg Asp Lys Leu Val Ala His Ala Val Arg Gln Ala Tyr Arg Asp Val
                100                 105                 110

Leu Phe Asn Gly Arg His Pro Thr Phe Val Leu Phe Glu Val Asp
                115                 120                 125

Pro Ser Val Val
        130

<210> SEQ ID NO 48
<211> LENGTH: 146
<212> TYPE: PRT
<213> ORGANISM: Streptococcus pneumoniae

<400> SEQUENCE: 48

Leu Phe Phe Asn Thr Pro Ala Arg Leu Lys Tyr Met Lys Ser Gln Gln
1               5                   10                  15

Ala Glu Leu Ser His Ile Ile Asp Ile Val Asn Arg Leu Gly Leu Ala
            20                  25                  30

His Pro Glu Ile Ser Phe Ser Leu Ile Ser Asp Gly Lys Glu Met Thr
        35                  40                  45
```

```
Arg Thr Ala Gly Thr Gly Gln Leu Arg Gln Ala Ile Ala Gly Ile Tyr
    50              55                  60

Gly Leu Val Ser Ala Lys Lys Met Ile Glu Ile Glu Asn Ser Asp Leu
65              70                  75                      80

Asp Phe Glu Ile Ser Gly Phe Val Ser Leu Pro Glu Leu Thr Arg Ala
                85              90                  95

Asn Arg Asn Tyr Ile Ser Leu Phe Ile Asn Gly Arg Tyr Ile Lys Asn
            100                 105                 110

Phe Leu Leu Asn Arg Ala Ile Leu Asp Gly Phe Gly Ser Lys Leu Met
        115             120                 125

Val Gly Arg Phe Pro Leu Ala Val Ile His Ile His Ile Asp Pro Tyr
    130             135                 140

Leu Ala
145
```

CLONING AND EXPRESSION OF THERMOSTABLE MULTI GENES AND PROTEINS AND USES THEREOF

GOVERNMENT SUPPORT

This work was supported by Grant No. HG 00446 from the National Institutes of Health. The United States government has certain rights to this invention.

BACKGROUND OF THE INVENTION

The polymerase chain reaction (PCR) is one of the most important technologies for genome analysis. One of the weaknesses of PCR is that primer extension from mismatched primers occurs. Extension from mismatched primers limits allele-specific amplification and detection of mutations and polymorphisms to some extent with homogeneous DNA samples (e.g. for genotyping), but to a greater extent for heterogeneous DNA samples (e.g. for detection of cancer mutations). Another of the weaknesses of PCR is much poorer fidelity than observed during in vivo DNA replication, as reflected in (1) a rather high rate of nucleotide misincorporation, leading to difficulty in using PCR for faithful cloning and (2) the production of multiple bands when di- and trinucleotide repeats are amplified. An order of magnitude improvement in PCR specificity and fidelity could increase accuracy in genotyping and somatic mutation detection and open up new uses for PCR, including the reproducible and faithful cloning of genomic DNA fragments up to several kilobases in length. The present invention provides such an improvement in PCR.

The ligase chain reaction (LCR) and its variations (e.g., oligonucleotide ligation assay (OLA), ligase detection reaction (LDR)) are alternative techniques for genome analysis. A commonly recognized source of spurious background signal in LCR and its variations, as well as in PCR and its variations, is the hybridization of an oligonucleotide such as a probe or a primer, to regions of the nucleic acid not intended to be amplified. Generally, these hybridizations occur because the target sample contains, in addition to the target sequence itself, other sequences with some similarity to the target nucleic acid. Although hybridization of probe or primer to these similar sequences is not as probable as to the target sequence, some hybridization can occur. When such unintended non-specific hybridization occurs, it is possible that sequences other than the targeted sequence will be amplified. If these limitations of PCR and LCR could be reduced or eliminated, the methods would be even more useful than they presently are.

SUMMARY OF THE INVENTION

The invention relates to isolated nucleic acids which encode a thermostable protein that enhances specific binding of a thermostable mismatch binding protein to bulge loops in a heteroduplex nucleic acid. As used herein, bulge loops include mispaired bases and frameshifts of 1–4 nucleotides or more. A protein which enhances specific binding of a thermostable mismatch binding protein to bulge loops in a heteroduplex nucleic acid is defined herein to include proteins which increase the occurrence of binding to bulge loops in a heteroduplex nucleic acid by a thermostable mismatch binding protein and proteins which increase the stability of complexes produced by binding of a thermostable mismatch binding protein to a bulge loop in a heteroduplex nucleic acid. A complex produced by binding of a thermostable mismatch binding protein to a bulge loop in a heteroduplex nucleic acid is referred to herein as a "thermostable bulge loop-binding protein-heteroduplex nucleic acid complex".

In one embodiment, the invention relates to nucleic acids which encode thermostable MutL proteins. Such nucleic acids include, for example, nucleic acids encoding *Aquifex pyrophilus* MutL, *Thermotoga maritima* MutL or *Thermus thermophilus* MutL, and nucleic acids which hybridize to these nucleic acids and encode a thermostable protein that enhances binding of a thermostable mismatch binding protein to bulge loops in a heteroduplex nucleic acid. In another embodiment, the invention relates to nucleic acids which hybridize to nucleic acids encoding *Aquifex pyrophilus* MutL, *Thermotoga maritima* MutL or *Thermus thermophilus* MutL and are useful as probes or primers to detect and/or recover homologous genes from other hyperthermophilic or thermophilic bacteria, including homologous genes from members of the genus Aquifex other than *Aquifex pyrophilus*, from members of the genus Thermotoga other than *Thermotoga maritima* and from members of the genus Thermus other than *Thermus thermophilus*. The invention further relates to recombinant constructs and vectors comprising nucleic acids that encode *Aquifex pyrophilus* MutL, *Thermotoga maritima* MutL or *Thermus thermophilus* MutL, or nucleic acids which hybridize thereto.

The invention also relates to proteins isolated from hyperthermophilic and thermophilic bacteria that enhance binding of thermostable mismatch binding proteins to bulge loops in a heteroduplex nucleic acid. As used herein, the phrase "isolated from" or "isolated nucleic acid" refers to nucleic acid obtained from (isolated from) naturally occurring sources as well as nucleic acids produced by recombinant methods or chemical synthesis, or by combinations of biological and chemical methods. Isolated nucleic acids produced by recombinant methods (e.g., genetic engineering methods) or synthesized chemically can also be referred to, respectively, as recombinantly produced nucleic acids and chemically synthesized or synthetic nucleic acids.

The invention further relates to isolated MutL proteins from hyperthermophilic or thermophilic bacteria. "Isolated" MutL proteins from hyperthermophilic or thermophilic bacteria include those obtained from naturally-occurring sources, as well as those produced by recombinant methods or chemical synthesis, or by combinations of biological and chemical methods.

The invention also relates to isolated thermostable proteins or polypeptides that enhance binding of thermostable mismatch binding proteins to bulge loops in a heteroduplex nucleic acid. Recombinant thermostable proteins that enhance binding of thermostable mismatch binding proteins to bulge loops in a heteroduplex nucleic acid can be produced in host cells using cells and methods described herein.

Another embodiment of the invention relates to a method of reducing DNA misincorporation (i.e., improving fidelity of DNA replication) in an amplification reaction by including a thermostable mismatch binding protein with a thermostable protein that enhances binding of the thermostable mismatch binding protein to bulge loops in the reaction. The thermostable mismatch binding protein binds to bulge loops in a heteroduplex nucleic acid formed as a result of misincorporation of deoxynucleoside triphosphates during the amplification reaction. This results in formation of a thermostable bulge loop-binding protein-heteroduplex nucleic acid complex. Binding of the thermostable protein prevents nucleic acids which include misincorporated deoxynucleoside triphosphates from acting as templates in subsequent rounds of the amplification reaction. Thus, amplification of nucleic acids which include misincorporated deoxynucleoside triphosphates is prevented, resulting in a reduction in overall DNA misincorporation. The thermostable protein that enhances binding of the thermostable mismatch binding protein to bulge loops in a heteroduplex nucleic acid improves this reaction. As used herein, "thermostable bulge loop-binding protein" refers to a thermostable mismatch binding protein.

The present invention further relates to a method for detecting a target nucleic acid which includes a specific sequence comprising combining a thermostable mismatch binding protein which binds specifically to bulge loops in a heteroduplex nucleic acid, a thermostable protein that enhances binding of the thermostable mismatch binding protein to the bulge loops, and an amplification reaction mixture, to produce a test combination. The individual components of an amplification reaction mixture can each be added, together or separately (e.g., individually), in any order, prior to, subsequent to or simultaneously with the thermostable mismatch binding protein which binds specifically to bulge loops in a heteroduplex nucleic acid, and/or the thermostable protein that enhances binding of the thermostable mismatch binding protein to the bulge loops. The resulting test combination is maintained under conditions appropriate for nucleic acid amplification to occur (i.e., synthesis of extension product). The amount of extension product synthesized in the test combination is determined and compared with the amount of product synthesized in a corresponding negative control (the control amount) to determine if the specific sequence suspected of being present in the nucleic acids being assessed is present. If the amount of product synthesized in the test combination is the same as or less than the amount of product synthesized in the corresponding negative control, then the nucleic acids being assessed do not include the specific sequence. If the amount of product synthesized in the test combination is greater than the amount of product synthesized in the corresponding control, then the nucleic acids being assessed include the specific sequence.

In one embodiment, the amplification reaction mixture comprises (1) a nucleic acid to be assessed for a specific sequence of interest; (2) four different nucleoside triphosphates; (3) two oligonucleotide primers where each primer is selected to be complementary to different strands of the nucleic acid which includes the specific sequence of interest, such that the extension product synthesized from one primer, when separated from its complement, can serve as a template for synthesis of the extension product of the other primer, at a temperature which promotes hybridization of each primer to its complementary strand; (4) a blocking oligonucleotide completely complementary to the sequence of interest; (5) a thermostable enzyme which catalyzes combination of the nucleoside triphosphates to form primer extension products complementary to each strand of the nucleic acid which includes the sequence of interest; and (6) an amplification buffer suitable for the activity of the enzyme. Thus, for example, one or more of the different nucleoside triphosphates can be added prior to, subsequent to or simultaneously with the thermostable mismatch binding protein which binds specifically to bulge loops in a heteroduplex nucleic acid and/or the thermostable protein that enhances binding of the thermostable mismatch binding protein to the bulge loops. One or more of the primers can be added prior to, subsequent to or simultaneously with one or more of the different nucleoside triphosphates, the thermostable mismatch binding protein and/or the thermostable protein that enhances binding of the thermostable mismatch binding protein to the bulge loops. Similarly, the blocking oligonucleotide, the thermostable enzyme, the nucleic acid to be assessed for the specific sequence of interest and/or the amplification buffer can each be added prior to, subsequent to or simultaneously with one or more of the different nucleoside triphosphates, one or more of the primer, the thermostable mismatch binding protein and/or the thermostable protein that enhances binding of the thermostable mismatch binding protein to the bulge loops. The blocking oligonucleotide, the thermostable enzyme, the nucleic acid to be assessed for the specific sequence of interest, and the amplification buffer can also be added in any order relative to each other. As used herein, the term "blocking oligonucleotide" refers to an oligonucleotide, whether occurring naturally as in a purified restriction digest or produced synthetically, which is capable of inhibiting propagation of polymerization of a primer extension product (i.e., inhibiting elongation of the extension product) when placed under conditions in which primer extension product is elongated. The blocking oligonucleotide is modified at the 3' end to prevent it from functioning as a primer. Such a blocking oligonucleotide is also referred to herein as an "unextendable oligonucleotide". For example, the oligonucleotide can be modified with a 3' phosphate to prevent it from functioning as a primer in the presence of Taq polymerase.

In another embodiment, the amplification reaction mixture comprises (1) a nucleic acid to be assessed for a specific sequence of interest; (2) four different nucleoside triphosphates; (3) two oligonucleotide primers where each primer is selected to be complementary to different strands of the nucleic acid which includes the specific sequence of interest, with one primer completely complementary to the sequence of interest, such that the extension product synthesized from one primer, when separated from its complement, can serve as a template for synthesis of the extension product of the other primer, at a temperature which promotes hybridization of each primer to its complementary strand; (4) a thermostable enzyme which catalyzes combination of the nucleoside triphosphates to form primer extension products complementary to each strand of the nucleic acid which includes the specific sequence of interest; and (5) an amplification buffer suitable for the activity of the enzyme. In a particular embodiment, the amplification reaction mixture further comprises a blocking oligonucleotide completely complementary to the complementary strand of the sequence of interest.

In a further embodiment, the amplification reaction mixture comprises (1) a nucleic acid to be assessed for a specific sequence of interest; (2) four oligonucleotide probes, two primary and two secondary probes, with one primary probe completely complementary to the specific sequence of interest and one secondary probe completely complementary to the complementary strand of the specific sequence of interest; (3) a thermostable enzyme which catalyzes fusion of oligonucleotide probes to form amplified products complementary to each strand of the nucleic acid which includes the specific sequence of interest; and (4) an amplification buffer suitable for the activity of the enzyme. In a particular embodiment, one of the probes which is completely complementary to the specific sequence of interest is omitted. As used herein, the term "probe" is defined to include an oligonucleotide, whether occurring naturally as in a purified restriction digest for example, or produced synthetically, which is capable of being covalently fused or ligated together into a product which is complementary to a nucleic acid strand of the target template when placed under conditions in which product formation is initiated.

As a negative control, a mixture containing (1) a nucleic acid which does not have the specific sequence thought to be included in the template being evaluated (i.e., containing only mismatched versions of the template being evaluated) and (2) the oligonucleotide designed to be completely complementary to the specific sequence thought to be included in the template being evaluated, is maintained under (a) conditions in which primer extension is initiated in the case where the oligonucleotide is a primer or under (b) conditions in which primer extension product is elongated in the case where the oligonucleotide is a blocking oligonucleotide or under (c) conditions in which target template is amplified in the case where the oligonucleotide is a probe. The amount of amplification product synthesized in the control is compared to the amount of amplification product synthesized in a sample which comprises template nucleic acids assessed for the specific sequence of interest. If the amount of amplification product synthesized in the sample which comprises template nucleic acids assessed for the specific sequence of interest is the same as or less than the amount of amplification product synthesized in the control, the specific sequence of interest is likely not included in the template nucleic acid. In the case of the opposite result (if the amount of amplification product synthesized in the sample which comprises template nucleic acids assessed for the specific sequence of interest is greater than the amount of amplification product synthesized in the control), the specific sequence of interest is likely included in the template nucleic acid.

In a particular embodiment, the specific sequence of interest is a mutation.

The present invention also relates to a method for amplifying a nucleic acid comprising a specific sequence of interest. The method comprises (a) combining a thermostable mismatch binding protein which binds specifically to bulge loops in a heteroduplex nucleic acid, and a thermostable protein that enhances binding of the thermostable mismatch binding protein to bulge loops and an amplification reaction mixture, thereby producing a test combination; and (b) maintaining the test combination of step (a) under conditions appropriate for amplification of nucleic acids to occur, resulting in synthesis of the nucleic acid comprising the sequence of interest. In a particular embodiment, the amplification reaction mixture includes (1) a nucleic acid comprising a specific sequence to be amplified; (2) four different nucleoside triphosphates; (3) two oligonucleotide primers where each primer is selected to be completely complementary to different strands of the nucleic acid comprising the specific sequence to be amplified; (4) blocking oligonucleotides which form heteroduplexes with a strand of the nucleic acids being selected against; (5) a thermostable enzyme which catalyzes combination of the nucleoside triphosphates to form primer extension products complementary to each strand of the nucleic acid comprising the specific sequence to be amplified; and (6) an amplification buffer suitable for the activity of the enzyme. The individual components of the amplification reaction mixture can each be added, together or individually and separately in any order, prior to, subsequent to or simultaneously with the thermostable mismatch binding protein which binds specifically to bulge loops in a heteroduplex nucleic acid and/or the thermostable protein that enhances binding of the thermostable mismatch binding protein to the bulge loops.

The invention further relates to a method for selecting against (i.e., reducing or preventing amplification of) a nucleic acid comprising a specific sequence of interest. The method comprises (a) combining a thermostable mismatch binding protein which binds specifically to bulge loops in a heteroduplex nucleic acid, a thermostable protein that enhances binding of the thermostable mismatch binding protein to bulge loops, and an amplification reaction mixture, thereby producing a test combination and (b) maintaining the test combination of step (a) under conditions appropriate for amplification of nucleic acids to occur. The thermostable mismatch binding protein binds heteroduplexes containing the nucleic acids to be selected against, preventing them from acting as templates in subsequent rounds of the amplification reaction and thereby selecting against a nucleic acid comprising the specific sequence. The thermostable protein which enhances binding of the thermostable mismatch binding protein to bulge loops improves this reaction. In a particular embodiment, the amplification reaction mixture comprises (1) nucleic acids comprising a specific sequence to be amplified or detected and nucleic acids whose synthesis is to be prevented or reduced (nucleic acids to be selected against); (2) four different nucleoside triphosphates; (3) two oligonucleotide primers where each primer is selected to be complementary to different strands of the nucleic acid comprising the specific sequence to be amplified or detected; (4) blocking oligonucleotides which form heteroduplexes with a strand of the nucleic acid whose synthesis is to be prevented or reduced (the nucleic acid being selected against); (5) a thermostable enzyme which catalyzes combination of the nucleoside triphosphates to form primer extension products complementary to each strand of the nucleic acid comprising the specific sequence to be amplified or detected; and (6) an amplification buffer suitable for the activity of the enzyme. The individual components of the amplification reaction mixture can each be added, together or separately (e.g., individually) in any order, prior to, subsequent to or simultaneously with the thermostable mismatch binding protein which binds specifically to bulge loops in a heteroduplex nucleic acid and/or the thermostable protein that enhances binding of the thermostable mismatch binding protein to the bulge loops.

In each particular embodiment, the amplification reaction mixture can further include additional components, such as, for example, components which enhance the activity of thermostable enzymes to catalyze combination of nucleoside triphosphates to form primer extension products or components which enhance and/or improve the amplification reaction and/or the utility of the amplification procedure.

The invention further relates to an improvement in a method of amplification wherein the improvement comprises adding a thermostable protein that enhances specific binding of a thermostable mismatch binding protein to bulge loops in a heteroduplex nucleic acid to a solution comprising an amplification reaction mixture and the thermostable mismatch binding protein. Thermostable MutL protein is an example of a thermostable protein that enhances specific binding of a thermostable mismatch binding protein to bulge loops that can be added.

The methods of the invention can further comprise including a stabilizer. As used herein, a stabilizer increases the lifetime of a thermostable bulge loop-binding protein-heteroduplex nucleic acid complex. A thermostable bulge loop-binding-heteroduplex nucleic acid complex is a complex formed when the thermostable mismatch binding protein is bound to a bulge loop in a heteroduplex nucleic acid. ATPγS is an example of a stabilizer.

Oligonucleotides which are designed so that they form heteroduplexes with a strand of the nucleic acid differ at one or more base pairs, at one or more sites, from the nucleic acid to be selected against. Oligonucleotides which are designed to be completely complementary to a specific sequence of interest or are designed to form heteroduplexes with a strand of the nucleic acid can be primers, blocking oligonucleotides or probes.

The components of an amplification reaction mixture and amplification conditions depend upon the particular amplification procedure being employed and can be determined from readily available sources. The components of an amplification mixture further depend on whether the specific sequence of interest is in, for example, a region of high GC content or a region of high AT content. Amplification procedures include, for example, PCR, LCR and their variations.

BRIEF DESCRIPTION OF THE DRAWINGS

FIG. 1 depicts the DNA sequence (SEQ ID NO:1) of the coding region of *Aquifex pyrophilus* (Apy) MutS.

FIG. 2 depicts the amino acid sequence (SEQ ID NO:2) of *Aquifex pyrophilus* MutS.

FIG. 3 depicts the DNA sequence (SEQ ID NO:4) of the coding region of *Thermotoga maritima* (Tma) MutS.

FIG. 4 depicts the amino acid sequence (SEQ ID NO:5) of *Thermotoga maritima* MutS.

FIG. 5 depicts the partial DNA sequence (SEQ ID NO:6) of the coding region of *Thermus thermophilus* MutS.

FIG. 6 depicts the partial DNA sequence (SEQ ID NO:7) of the coding region of *Thermus aquaticus* MutS.

FIG. 7 depicts the alignment of partial amino acid sequences for the coding regions of *Aquifex pyrophilus* MutS (SEQ ID NO:2), *Thermus aquaticus* (Taq) MutS (SEQ ID NO:8), *Thermus thermophilus* (Tth) MutS (SEQ ID NO:9) and *Thermotoga maritima* MutS (SEQ ID NO:5). The numbers "613" and "595" correspond to amino acid position 613 in Apy MutS and amino acid position 595 in Tma MutS, respectively.

FIG. 8 depicts the DNA sequence (SEQ ID NO:39) of the coding region of *Aquifex pyrophilus* MutL.

FIG. 9 depicts the DNA sequence (SEQ ID NO:41) of the coding region of *Thermotoga maritima* MutL.

FIGS. 10A–10B depicts the amino acid sequences of *Escherichia* (E.) *coli* (Eco) MutS (SEQ ID NO:3), *Aquifex* (A.) *pyrophilus* MutS (SEQ ID NO:2) and *Thermotoga* (T.) *maritima* MutS (SEQ ID NO:5), with (|) indicating identical amino acids and (:) indicating similar amino acids (TFASTA).

FIGS. 11A–11B depicts the amino acid sequences of *Aquifex pyrophilus* (Apy) MutL (SEQ ID NO:40), *Thermotoga maritima* (Tma) MutL (SEQ ID NO:42), *Streptococcus* (S.) *pneumoniae* (Spn) HexB (SEQ ID NO:43) and *Escherichia* (E.) *coli* (Eco) MutL (SEQ ID NO:44) (PILEUP).

FIG. 12 depicts an analysis of the 5' and 3' untranslated regions of Tma MutS. Initiation : Double underlines indicate, in order, an in frame termination codon (TGA), a valine codon (GTN), a termination codon (TGA) for an upstream open reading frame (orf), the region of similarity to the 3' end of Tma 16S rRNA, and two additional valine codons. Termination : Double underlines indicate the antisense termination codon (TCA) for a downstream, antisense open reading frame (orf) and the termination codon (TGA) for Tma MutS. Proteins with identical (|) or similar (:) amino acids (TFASTA) to the open reading frame are shown.

FIG. 13 depicts the partial DNA sequence (SEQ ID NO:45) of the coding region of *Thermus thermophilus* MutL.

FIG. 14 depicts the alignment of partial amino acid sequences for the coding regions of *E. coli* MutL (SEQ ID NO:46), *Thermus thermophilus* MutL (SEQ ID NO:47) and *S. pneumoniae* HexB (SEQ ID NO:48). The numbers refer to the positions of the amino acids in *E. coli* MutL.

DETAILED DESCRIPTION OF THE INVENTION

Mismatch correction in prokaryotic and eukaryotic species may be initiated by the mismatch binding of a homolog of the product of one of several *E. coli* mutator genes, mutS. In *E. coli*, mismatch correction also requires MutL, the endonucleolytic activity of MutH, and the activities of several additional enzymes (Modrich, P., *Annu. Rev. Genet.* 25: 229–253 (1991); Modrich, P., *Science* 266: 1959–1960 (1994)). Insertions into mutS lead to a high frequency of spontaneous mutation which may easily be detected as an increased frequency of streptomycin resistant cells (Siegel, E. C. et al., *Mutat. Res.* 93: 25–33 (1982)). The MutHSL system selectively removes mismatches from daughter strands following incorrect incorporation of nucleotides during DNA replication (Au, K. G. et al., *J. Biol. Chem.* 267: 12142–12148 (1992)). In *E. coli*, GATC sites are methylated by the dam methylase. Hemimethylation at GATC permits differentiation of template from daughter strands. The repair of a mismatch is bidirectional with respect to the hemimethylated site (Cooper, D. L. et al., *J. Biol. Chem.* 268: 11823–11829 (1993)). In addition, the same mismatch correction system is responsible for removing frameshifts of up to four nucleotides which may be the result of the presence of an intercalating agent during DNA replication (Rene, B. et al., *Mutat. Res.* 193: 269–273 (1988)) or of polymerase slippage at di- or tri-nucleotide repeats (Parker, B. O. and Marinus, M. G., *Proc. Natl. Acad. Sci. USA* 89: 1730–1734 (1992)). Transition and frameshift mutations are increased about 275- and 1500-fold, respectively, in mutS⁻ *E. coli* cells (Schaaper, R. M. and Dunn, R. L., *Genetics* 129: 317–326 (1991)).

In man, the mutS homolog (MSH2) is a mutator gene involved in hereditary nonpolyposis colorectal cancer (Leach, F. S. et al., *Cell* 75: 1215–1225 (1993); Fishel, R. et al., *Cell* 75: 1027–1038 (1993)), and there are now phenotypes for a growing list of human mismatch repair proteins. Cells deficient in MutS homolog-dependent mismatch repair fail to accumulate single-strand breaks and are resistant to killing by alkylating agents (Branch, P. et al., *Nature* 362: 652–654 (1993)), suggesting that in wild-type cells, introduction of alkylated sites reactivates mismatch repair and that MutS homologs find target sites, whether they be mismatches or other small lesions. In fact, the replication of alkylated DNA in mutS⁻ *E. coli* cells may contribute to the hypermutation phenotype.

Purified *E. coli* MutS protein binds specifically to oligonucleotide heteroduplexes (Su, S.-S. and Modrich, P., *Proc. Natl. Acad. Sci. USA* 83: 5057–5061 (1985)). Gel-shift assays may be carried-out with *E. coli* MutS protein and a heteroduplex with a GT mismatch (less efficiently an AC mismatch) (Jiricny, J. et al., *Nucleic Acids Res.* 16: 7843–7853 (1988)) or a 3-nucleotide bulge loop (Lishanski, A. et al., *Proc. Natl. Acad. Sci. USA* 91: 2674–2678 (1994)) to detect MutS protein binding. *E. coli* MutS protein also binds specifically to heteroduplexes containing IC mismatches (Jiricny, J. et al., *Nucleic Acids Res.* 16: 7843–7853 (1988)). Human MSH2 also binds to GT mismatches (Fishel, R. et al., *Cancer Res.* 54: 5539–5542 (1994)). However, binding to bulge loops is not limited to 1–4 nucleotides but occurs with loops as large as 14 nucleotides in length (Fishel, R. et al., *Science* 266: 1403–1405 (1994)). The binding of *E. coli* MutS protein to mismatches in the presence of *E. coli* MutL protein is sufficiently strong that it will block RecA-mediated strand displacement reactions (Worth, L., Jr. et al., *Proc. Natl. Acad. Sci. USA* 91: 3238–3241 (1994)) and by itself the exonuclease activity of T7 DNA polymerase (Ellis, L. A. et al., *Nucleic Acids Res.* 22: 2710–2711 (1994)).

Applicant has cloned and expressed thermostable MutL proteins from hyperthermophilic eubacteria and demonstrated that specific binding of thermostable MutS proteins to bulge loops in a heteroduplex nucleic acid is enhanced in the presence of a thermostable MutL protein. Until Applicant's cloning and isolation of thermostable MutL proteins, all of the studies of MutL and MutL-homolog proteins have involved proteins from mesophilic organisms.

As used herein, the term "thermostable protein" refers to protein of thermophilic bacterial origin or hyperthermophilic bacterial origin. Such thermostable proteins can be obtained from an organism in which they occur in nature, can be produced by recombinant methods or can be synthesized chemically.

As used herein, the terms "heteroduplex nucleic acid" and "heteroduplex" refer to a double-stranded nucleic acid which is formed by a mismatch (e.g., C-A or G-T nucleotide pairs as opposed to the naturally-occurring C-G or A-T nucleotide pairs or frameshifts of 1–4 nucleotides or more) between complementary strands. As used herein, the terms "homoduplex nucleic acid" and "homoduplex" refer to a double-stranded nucleic acid which is formed by perfectly matched complementary strands. As defined herein, a bulge loop is a distortion in double-stranded nucleic acids. A bulge loop arises as a result of, for example, a frameshift or a mispairing between strands in a limited region, i.e., a mismatch between complementary strands, and comprises a mismatch of at least a single nucleotide.

NUCLEIC ACIDS, CONSTRUCTS AND VECTORS

The present invention relates to isolated nucleic acids which encode a thermostable protein that enhances specific binding of thermostable mismatch binding proteins to bulge loops in a heteroduplex nucleic acid. A protein which enhances specific binding of a thermostable mismatch binding protein to bulge loops in a heteroduplex nucleic acid is defined herein to include proteins which increase the occurrence of binding to bulge loops in a heteroduplex nucleic acid by a thermostable mismatch binding protein and proteins which increase the stability of complexes produced by binding of a thermostable mismatch binding protein to a bulge loop in a heteroduplex nucleic acid. A complex produced by binding of a thermostable mismatch binding protein to a bulge loop in a heteroduplex nucleic acid is referred to herein as a "thermostable bulge loop-binding protein-heteroduplex nucleic acid complex". As used herein, "thermostable mismatch binding proteins" are proteins, polypeptides or protein fragments which are stable to heat, bind specifically to bulge loops in a heteroduplex nucleic acid, have heat resistant nucleic acid binding activity and do not become irreversibly denatured (inactivated) when subjected to the elevated temperatures for the time periods necessary, for example, for PCR amplification. Examples of thermostable mismatch binding proteins include thermostable MutS proteins from *Aquifex pyrophilus, Thermotoga maritima, Thermus thermophilus* and *Thermus aguaticus*, and variants (e.g. mutants) of those proteins and/or portions thereof. Thermostable MutS proteins and methods for their production are described herein, and in U.S. Application Ser. No. 08/468,558 (filed Jun. 6, 1995; now U.S. Pat. No. 5,877,280) and International Application No. PCT/US96/08677 (filed Jun. 4, 1996). The teachings of U.S. Application Ser. No. 08/468,558 (filed Jun. 6, 1995; now U.S. Pat. No. 5,877,280) and International Application No. PCT/US96/08677 (filed Jun. 4, 1996) are both entirely incorporated herein by reference. A thermostable MutS protein from *Thermus aquaticus* is described by Biswas, I. and Hsieh, P. (*J. Biol. Chem.* 271(9):5040–5048 (1996)), the teachings of which are entirely incorporated herein by reference. A thermostable MutS protein from *Thermus thermophilus* is described by Takamatsu, S. et al. (*Nucleic Acids Research* 24(4):640–647 (1996)), the teachings of which are entirely incorporated herein by reference.

In one embodiment, the nucleic acid encodes a thermostable protein that enhances specific binding of thermostable MutS proteins to bulge loops in a heteroduplex nucleic acid. The present invention also relates more specifically to isolated nucleic acids which encode a thermostable MutL protein from hyperthermophilic or thermophilic bacteria. The present invention further relates to isolated nucleic acids which encode a thermostable MutL protein from *Aquifex pyrophilus* and isolated nucleic acids which encode a thermostable MutL protein from *Thermotoga maritima*. The present invention also relates to isolated nucleic acids which encode a thermostable MutL protein from *Thermus thermophilus*.

The invention also relates to isolated nucleic acids which (1) hybridize to (a) a nucleic acid encoding a thermostable MutL protein, such as a nucleic acid having the sequence of FIG. 8 (SEQ ID NO:39), FIG. 9 (SEQ ID NO:41) or FIG. 13 (SEQ ID NO:45), (b) the complement of any one of (a), or (c) portions of either of the foregoing (e.g., a portion comprising the open reading frame); (2) encode a polypeptide having the amino acid sequence of a thermostable MutL protein (e.g., SEQ ID NO:40 or SEQ ID NO:42), or functional equivalents thereof (e.g., a thermostable polypeptide that enhances specific binding of thermostable mismatch binding proteins to bulge loops in a heteroduplex nucleic acid with a selected amino acid); or (3) have both characteristics. Portions of the isolated nucleic acids which code for polypeptides having a certain function can be identified and isolated by, for example, the method of Jasin, M., et al., U.S. Pat. No. 4,952,501, which reference is entirely incorporated herein by reference.

Nucleic acids meeting these criteria comprise nucleic acids having sequences identical to sequences of naturally occurring thermostable MutL proteins from *Aquifex pyrophilus, Thermotoga maritima* or *Thermus thermophilus*, or variants of the naturally occurring sequences. Such variants include mutants differing from naturally occurring sequences by the addition, deletion or substitution of one or more residues, modified nucleic acids in which one or more residues are modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are set forth on pages 2.10.1–2.10.16 (see particularly 2.10.8–11) and pages 6.3.1–6 in *Current Protocols in Molecular Biology* (Ausubel, F. M. et al., Vol. 1, Suppl. 26, 1991), the teachings of which are entirely incorporated herein by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity.

Isolated nucleic acids that are characterized by their ability to hybridize to (a) a nucleic acid encoding a thermostable MutL protein (for example, those nucleic acids depicted in FIG. 8 (SEQ ID NO:39), FIG. 9 (SEQ ID NO:41) and FIG. 13 (SEQ ID NO:45), (b) the complement of such nucleic acids, (c) or a portion thereof (e.g. under high or moderate stringency conditions), and which encode a thermostable protein or polypeptide which enhances specific binding of thermostable mismatch binding proteins to bulge loops in a heteroduplex nucleic acid are also the subject of this invention. The binding function of a protein or polypeptide encoded by hybridizing nucleic acid may be detected by standard assays for binding (e.g., mismatch binding assays which demonstrate binding of the protein or polypeptide to a bulge loop in a heteroduplex nucleic acid such as, for example, gel shift assays). Functions characteristic of the thermostable MutL protein may also be assessed by in vivo complementation tests or other suitable methods. Mismatch binding assays, complementation tests, or other suitable methods can also be used in procedures for the identification and/or isolation of nucleic acids which encode a polypeptide such as a polypeptide of the amino acid sequence SEQ ID NO:40 or SEQ ID NO:42, or functional equivalents of these polypeptides. The antigenic properties of proteins or polypeptides encoded by hybridizing nucleic acids can be determined by immunological methods employing antibodies that also bind to a naturally-occurring thermostable MutL protein. These methods can include immunoblot, immunoprecipitation and radioimmunoassay.

Nucleic acids of the present invention can be used in the production of proteins or polypeptides. For example, DNA encoding a thermostable MutL protein, such as a thermostable MutL from *Aquifex pyrophilus*, or DNA which hybridizes to DNA having the sequence SEQ ID NO:39, can be incorporated into various constructs and vectors created for further manipulation of sequences or for production of the encoded polypeptide in suitable host cells. Similarly, DNA containing all or part of the coding sequence for a thermostable MutL protein, such as a thermostable MutL from *Thermotoga maritima*, or DNA which hybridizes to DNA having the sequence SEQ ID NO:41, can be incorporated into various constructs and vectors created for further manipulation of sequences or for production of the encoded polypeptide in suitable host cells. For expression in *E. coli* and other organisms, a GTG initiation codon can be altered to ATG as appropriate.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" 1 nucleic acids are also those that result from recombination events that occur through the natural mechanisms of cells, but are selected for after the introduction to the cells of nucleic acids designed to allow and make probable a desired recombination event.

MutL proteins from hyperthermophiles such as *Aquifex pyrophilus, Thermotoga maritima* and *Thermus thermophilus* can be used in methods for allele-specific amplification and in methods for enhancing amplification reactions because they are stable to heat, are heat resistant and do not become irreversibly denatured (inactivated) when subjected to the elevated temperatures for the length of time necessary for the denaturation and annealing steps of amplification techniques such as the polymerase chain reaction and its variations or the ligase chain reaction and its variations.

As described in the Examples, MutL genes were cloned into *E. coli* from two distantly-related hyperthermophilic eubacteria, *Aquifex pyrophilus* (Apy) and *Thermotoga maritima* (Tma). All cloning was carried out using PCR technology without the need for library construction. Inverse PCR is a rapid method for obtaining sequence data for the 5'- and 3'-flanking regions of bacterial genes, the prerequisite for generation of primers for PCR cloning into an expression vector. Because of the inherent error frequency of in vitro DNA replication, care was taken to demonstrate that sequences of independently-derived expression clones were identical. A MutL protein from each species was expressed and purified to homogeneity. The proteins were thermoresistant to $\geq 90°$ C. and enhanced binding of thermostable mismatch binding proteins to bulge loops in a heteroduplex nucleic acid.

The approaches described herein, including, but not limited to, the approaches to isolate and manipulate the MutL genes of *Aquifex pyrophilus* and *Thermotoga maritima*, to construct vectors and host strains, and to produce and use the proteins, to produce antibodies, etc., can be applied to other members of the genus Aquifex or other members of the genus Thermotoga. For example, the Apy MutL gene described here, or sufficient portions thereof, including fragments produced by PCR, can be used as probes or primers to detect and/or recover homologous genes of the other Aquifex species (e.g., by hybridization, PCR or other suitable techniques). Similarly, genes encoding Apy MutL and other Aquifex species MutL proteins can be isolated from genomic libraries according to methods described herein or other suitable methods. The Tma MutL gene described here, or sufficient portions thereof, including fragments produced by PCR, can be used as probes or primers to detect and/or recover homologous genes of the other Thermotoga species (e.g., by hybridization, PCR or other suitable techniques). Similarly, genes encoding Tma MutL and other Thermotoga species MutL proteins can be isolated from genomic libraries according to methods described herein or other suitable methods. Aquifex and Thermotoga species MutL proteins can be evaluated for their ability to enhance binding of thermostable mismatch binding proteins to bulge loops in a heteroduplex nucleic acid using methods described herein for evaluating the ability of Apy and Tma MutL proteins to enhance binding of thermostable mismatch binding proteins to bulge loops in a heteroduplex nucleic acid (e.g., gel shift binding assays).

The approaches described herein, including, but not limited to, the approaches to isolate and manipulate the MutL genes of *Aquifex pyrophilus* and *Thermotoga maritima*, to construct vectors and host strains, and to produce and use the proteins, to produce antibodies, etc., can also be applied to other hyperthermophilic bacteria and to thermophilic bacteria. Hyperthermophilic bacteria include species of the archaebacteria, which include the most hyperthermophilic species known. Hyperthermophilic archaebacteria include members of the genus Pyrodictium, including, but not limited to, *Pyrodictium abyssi* (Pab) and *Pyrodictium occultum* (Poc). Thermophilic bacteria include members of the genus Thermus, including, but not limited to, *Thermus aquaticus* (Taq) and *Thermus thermophilus* (Tth). Thermophilic bacteria also include hyperthermophilic bacteria. As used herein, "thermophilic bacteria" is meant to include hyperthermophilic and thermophilic bacteria.

For example, the partial DNA sequence (SEQ ID NO:45) of the coding region of Tth MutL protein was isolated according to methods described herein to isolate and munipulate the MutL genes of *Aquifex pyrophilus* and *Thermotoga maritima*. The partial Tth MutL DNA sequence described herein, or sufficient portions thereof, including fragments produced by PCR, can be used as probes or primers to detect and/or recover homologous DNA sequences and/or genes of the other Thermus species (e.g., by hybridization, PCR or other suitable techniques). Genomic DNA from several Thermus species (e.g., *Thermus thermophilus* and *Thermus aquaticus*) can be obtained, for example, from the American Type Culture Collection.

Hyperthermophilic archaebacteria *Pyrodictium abyssi* and *Pyrodictium occultum*, both from cells supplied by Professor Karl Stetter, Universitat Regensburg, can be used as templates for degenerate priming. Once Pab and Poc fragment sequences have been found which encode an amino acid sequence similar to other MutL proteins, unique inverse primers can be synthesized and tested by Southern hybridization to verify that these sequences originated from Pab and Poc genomic DNAs.

The 5' coding and 3' downstream noncoding sequences for Pab, Poc and Thermus species (e.g., Taq and Tth) mutL can be obtained by inverse PCR walking. The 5' coding sequence can be verified by cycle sequencing. These coding sequences can be used to design expression primers. Independently-derived PCR products resulting from each pair of expression primers can be ligated into one or more expression plasmids, including pDG160/pDG182/pDG184 and/or the pET series from Novagen, Inc., and electroporated into the appropriate hosts. Plasmids from several clones expressing each thermostable MutL can be sequenced.

The PCR amplifications of Pab, Poc and Thermus species genomic DNAs can be carried out in 50–100 Al containing 1 $\mu$M of each primer, 10 mM Tris buffer, pH 8.3, 50 mM KCl, 25–50 units/ml Taq DNA polymerase, and 200 $\mu$M of each dNTP (Saiki, R. K. et al., Science 239: 487–491 (1988)). Simultaneous reactions can be initiated by addition of a $MgCl_2$ solution to $Mg^{++}$-free PCR mixtures at >80° C. to yield final concentrations of 0.8–2 mM followed by denaturation for 30 seconds at 95° C.

When using degenerate primers and 50 ng of a genomic DNA template, the first 5 cycles will employ a 30 second annealing step at 45° C. followed by a 2 minute ramp to 72° C. before denaturation. An additional 30–35 cycles can be carried out with a 55° C. annealing temperature. For inverse PCR (Ochman, H. et al., In PCR Protocols. A Guide to Methods and Applications, Innis, M. A. et al., Eds. (San Diego: Academic Press, Inc.) pp. 219–227 (1990)), genomic DNA can be digested to completion with a restriction endonuclease leaving a 3' or 5' 4-base overhang, phenol extracted, and ligated overnight at a DNA concentration of less than 50 $\mu$g/ml. When using unique direct or inverse PCR primers, 50 ng of genomic or circularized genomic DNA template, respectively, can be employed, and the first 5 cycles omitted.

Thermostable protein mixtures from bacteria expressing Pab, Poc or a Thermus species MutL can be prepared and purified as described in the Examples pertaining to the preparation and purification of Apy and Tma MutL. The purification scheme can be optimized for each protein using routine experimentation. The proteins can be concentrated, and the solvent can be changed by dialysis. The final products can be analyzed for purity by SDS-PAGE. Protein concentrations can be determined using the Bio-Rad Protein Assay kit (Bradford) and by analysis of complete absorbance spectra, which will document removal of nucleic acids.

These purified MutL proteins can be evaluated for the ability to enhance binding of thermostable mismatch binding proteins to bulge loops in a heteroduplex nucleic acid using the methods described herein in evaluating the ability of the Apy and Tma MutL proteins to enhance binding of Apy and Tma MutS proteins to a bulge loop in a heteroduplex nucleic acid (see, e.g., gel shift assays).

PROTEINS

The invention also relates to thermostable proteins or polypeptides encoded by nucleic acids of the present invention. The thermostable proteins and polypeptides of the present invention enhance specific binding of thermostable mismatch binding proteins to bulge loops in a heteroduplex nucleic acid. As used herein, "thermostable proteins or polypeptides" are proteins, polypeptides or protein fragments which are stable to heat, have heat resistant activity (e.g., the ability to enhance specific binding of thermostable mismatch binding proteins to bulge loops in a heteroduplex nucleic acid), and do not become irreversibly denatured (inactivated) when subjected to the elevated temperatures for the time periods necessary, for example, for PCR amplification. Thermostable proteins are also proteins of thermophilic bacterial origin or hyperthermophilic bacterial origin. Such proteins can be obtained from (isolated from) an organism in which they occur in nature, can be produced by recombinant methods or can be synthesized chemically.

The thermostable proteins described herein are thermoresistant to $\geq 90°$ C. The thermostable proteins are known to enhance specific binding of thermostable mismatch binding proteins to bulge loops in a heteroduplex nucleic acid at temperatures of from about room temperature to about 90° C. However, specificity of binding to bulge loops is greatest at the high end of this temperature range. With decreasing temperature from about 60° C., an increasing proportion of protein is found to bind nonspecifically to nucleic acids forming perfect homoduplexes.

The thermostable proteins and polypeptides of the present invention can be isolated and/or recombinant.

Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, including essentially pure proteins or polypeptides, proteins or polypeptides produced by chemical synthesis, by recombinant methods, or by combinations of biological and chemical methods, and recombinant proteins or polypeptides which are isolated. Proteins or polypeptides referred to herein as "recombinant" or "recombinantly produced" are proteins or polypeptides produced by the expression of recombinant nucleic acids.

In one embodiment, the thermostable protein enhances specific binding of thermostable mismatch binding proteins to bulge loops in a heteroduplex nucleic acid. These thermostable proteins include, for example, naturally occurring thermostable MutL proteins from *Aquifex pyrophilus, Thermotoga maritima* and *Thermus thermophilus*, variants (e.g. mutants) of those proteins and/or portions thereof. Thermostable mismatch binding proteins include, for example, thermostable MutS proteins from naturally occurring, isolated and recombinant *Aquifex pyrophilus, Thermotoga maritima, Thermus thermophilus* and *Thermus aquaticus*, variants (e.g. mutants) of those proteins and/or portions thereof. As used herein, "variants" include mutants differing by the addition, deletion or substitution of one or more amino acid residues, or modified polypeptides in which one or more residues are modified, and mutants comprising one or more modified residues.

In another embodiment, like naturally occurring thermostable MutL proteins from *Aquifex pyrophilus, Thermotoga maritima* and *Thermus thermophilus*, isolated and/or recombinant thermostable MutL proteins of the present invention enhance specific binding of thermostable mismatch binding proteins to bulge loops in heteroduplex nucleic acids. For example, in the case of *Aquifex pyrophilus*, an isolated, recombinant thermostable MutL enhances specific binding of thermostable MutS proteins to bulge loops in a heteroduplex nucleic acid.

The invention further relates to fusion proteins, comprising a thermostable MutL protein (as described above) as a first moiety, linked to second moiety not occurring in the thermostable MutL protein as found in nature. The second moiety can be an amino acid or polypeptide. The first moiety can be in an N-terminal location, C-terminal location or internal to the fusion protein. In one embodiment, the fusion protein comprises a thermostable MutL protein of *Aquifex pyrophilus* origin as the first moiety, and a second moiety comprising a linker sequence and affinity ligand.

Fusion proteins can be produced by a variety of methods. For example, a fusion protein can be produced by the insertion of a thermostable MutL gene or portion thereof into a suitable expression vector, such as Bluescript SK +/− (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., Ausubel, F. M. et al., *Current Protocols in Molecular Biology*, John Wiley & Sons, New York, Vol. 2, Suppl. 26, pp. 16.4.1–16.7.8, 1991).

METHOD OF PRODUCING RECOMBINANT THERMOSTABLE MutL PROTEINS

Another aspect of the invention relates to a method of producing a thermostable MutL protein, and to expression systems and host cells containing a vector appropriate for expression of a thermostable MutL protein.

Cells that express a recombinant thermostable MutL protein can be made and maintained in culture to produce protein for isolation and purification. These cells can be procaryotic or eucaryotic. Examples of procaryotic cells that can be used to express thermostable MutL proteins include *Escherichia coli, Bacillus subtilis* and other bacteria. Examples of eucaryotic cells that can be used to express the thermostable MutL protein include yeasts such as *Saccharomyces (S.) cerevisiae, S. pombe, Pichia pastoris*, and other lower eucaryotic cells, as well as cells of higher eucaryotes, such as those from insects and mammals. (See, e.g., Ausubel, F. M. et al., *Current Protocols in Molecular Biology*, John Wiley & Sons Inc., New York, 1994).

To make host cells that produce a thermostable MutL protein for isolation and purification, as a first step the gene encoding the MutL protein can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for thermostable MutL protein operably linked to one or more expression control sequences whereby the coding sequence is under the control of transcription signals and linked to appropriate translation signals to permit translation of the thermostable MutL protein or of a fusion protein comprising a thermostable MutL protein. As a second step, the vector can be introduced into cells by a method appropriate to the type of host cells (e.g., transformation, transfection, electroporation, infection). In a third step, for expression from the thermostable MutL gene, the host cells can be maintained under appropriate conditions (e.g., in the presence of inducer, normal growth conditions) for expression of the gene and production of the encoded MutL protein.

As a particular example of the above approach to producing active thermostable MutL protein, a gene encoding the *Aquifex pyrophilus* MutL can be integrated into the genome of a virus that enters host cells. By infection of the host cells, the components of a system which permits the transcription and translation of the *Aquifex pyrophilus* MutL gene are introduced into the host cells, in which expression of the encoded product occurs. Alternatively, an RNA polymerase gene, inducer, or other component required to complete such a gene expression system may be introduced into the host cells already containing the Aquifex pyrophilus MutL gene, for example, by means of a virus that enters the host cells and contains the required component. The thermostable MutL gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

MUTATION OR POLYMORPHISM DETECTION

Genome mismatch scanning (GMS) (Brown, P. O., *Current Opinion in Genetics & Development* 4: 366–373 (1994)), a method for whole genome scanning which utilizes *E. coli* MutS and the other enzymes of the mismatch repair system, is one of the new methods being developed for mapping and/or cloning genes based on sequence differences or similarities in two DNA pools (Jonsson, J. J. and Weissman, S. M., *Proc. Natl. Acad. Sci. USA* 92: 83–95 (1995)). If the gene is known, several methods have been developed for scanning the specific DNA sequences for mutations or polymorphisms, including single-strand conformation polymorphism analysis (SSCP) (reviewed by Hayashi, K. and Yandell, D. W., *Human Mutation* 2: 338–346 (1993)), which does not require heteroduplex formation, and chemical and, most recently, endonuclease VII-based cleavage methods, which require heteroduplex formation (Youil, R. et al., *Proc. Natl. Acad. Sci. USA* 92: 87–91 (1995)).

If the mutation or polymorphism is known, several methods are available for identification of specific alleles which rely on identification of internal target sequences following PCR, including allele-specific oligonucleotide hybridization (Saiki, R. K. et al., *Proc. Natl. Acad. Sci. U.S.A.* 86: 6230–6234 (1989)), oligonucleotide ligation assay (Nickerson, D. A. et al., *Proc. Natl. Acad. Sci. U.S.A.* 87: 8923–8927 (1990)) and TaqMan (Livak, K. et al., *Nat. Genet.* 9: 341–342 (1995)). The problem is relatively straightforward for mapping germline genes, somewhat more difficult for detecting cancer-related mutations in tumors with mixed cell populations and quite difficult for screening lymph nodes or other sources (e.g. sputum) for cancer-related mutations. There are comparable problems in the analysis of mutations in pathogens. The methods for identification of specific alleles include allele-specific PCR (Kwok, S. et al., *Nucleic Acids Res.* 18: 999–1005 (1990); Tada, M. et al., *Cancer Res.* 53: 2472–2474 (1993); Bottema, C. D. et al., *Methods Enzymol.* 218: 388–402 (1993)), allele-specific ligase chain reaction (LCR) (Wiedmann, M. et al., *PCR Methods & Applications* 3: S51–64 (1994)), RFLP/PCR (Felley-Bosco, E. et al., *Nucleic Acids Res.* 19: 2913–2919 (1991); Cha, R. S. et al., *PCR. Methods. Appl.* 2: 14–20 (1992)), which requires a restriction endonuclease cleavage site in one allele, and combination methods (Hruban, R. H. et al., *Am. J. Pathol.* 143: 545–554 (1993)). Ras oncogene mutations have been detected by a hybridization technique subsequent to non-specific PCR in stool from patients with colorectal tumors (Sidransky, D. et al., *Science* 256: 102–105 (1992)). Mismatch-specific single-strand cleavage including MutY (Hsu, I.-C. et al., *Carcinogenesis* 15: 1657–1662 (1994)) coupled with ligase-mediated PCR (LMPCR) has permitted detection of certain human p53 mutations at a sensitivity of about 1%. The most complicated and least general methods, such as RFLP-PCR, need to be employed whenever the mutation is present in a small fraction of the templates (<1%). In addition, only RFLP/PCR in its pure form amplifies internal target sequences, permitting subsequent verification of the mutation by sequencing. Mismatch-specific TaqMan PCR, an embodiment of the present invention, also produces a product containing the mutant allele DNA which can be verified by sequencing.

The present invention relates to methods for enhancing allele-specificity, especially for transition and small frameshift mutations. The present invention more specifically relates to inclusion of a thermostable mismatch binding protein and a thermostable protein which enhances specific binding of the thermostable mismatch binding protein to bulge loops in a heteroduplex nucleic acid in a PCR amplification procedure. Examples of thermostable mismatch binding proteins include Apy, Tma, Tth and Taq MutS proteins. Examples of thermostable proteins which enhance specific binding of the thermostable mismatch binding protein to bulge loops in a heteroduplex nucleic acid include Apy, Tma and Tth MutL proteins. A simple assay would be more amendable to automation using highly-parallel "classical" or chip-based amplification technologies. Chip-based technologies can be used to provide an array of blocking oligonucleotides, permitting multiplex mismatch-specific TaqMan PCR.

In one embodiment, the invention relates to a method for enhancing mismatch-specific TaqMan PCR. As used herein, "TaqMan PCR" refers to a PCR assay based on the "Taqman" system described by Holland, P. M. et al., *Proc. Natl. Acad. Sci. U.S.A.* 88: 7276–7280 (1991). In a particular embodiment, Apy MutS or Tma MutS binds specifically to a heteroduplex internal oligonucleotide-template complex containing a GT transition mismatch or a small bulge loop and not to a perfectly matched internal oligonucleotide-template complex, thus interfering with propagation of polymerization (e.g., blocking DNA polymerization) from the mismatched template during each PCR cycle. Addition of Apy MutL or Tma MutL enhances mismatch-specific TaqMan PCR. For example, addition of Apy MutL or Tma MutL enhances binding of Apy MutS and Tma MutS to bulge loops in the heteroduplex internal oligonucleotide-template nucleic acid. Alternatively, addition of Apy MutL or Tma MutL stabilizes complexes produced by binding of Apy MutS or Tma MutS to a bulge loop in a heteroduplex nucleic acid. For detectable types of mutations, mismatch-specific TaqMan PCR is amenable to automation using highly-parallel "classical" or chip-based amplification technologies. Chip-based technologies can be used to provide an array of blocking oligonucleotides, permitting multiplex mismatch-specific TaqMan PCR.

For every AC mismatch on one nucleic acid strand, there is a GT mismatch on the other nucleic acid strand. In fact, a specific GT mismatch can always be formed between a TaqMan oligonucleotide of one polarity and a wild-type sequence, even in the case of transversion mutations. The specificity will then depend upon the extent to which the mutant allele could be amplified with a mismatched primer containing a mismatch other than GT.

Allele-specific oligonucleotides forming a GT mismatch can be synthesized, although thermostable mismatch binding proteins can bind to other types of heteroduplexes, which binding is enhanced in the presence of one or more thermostable proteins that enhance binding of thermostable mismatch binding proteins to bulge loops in a heteroduplex nucleic acid.

In another embodiment, the invention relates to a method for enhancing primer-directed allele-specific PCR. In a particular embodiment, Apy MutS or Tma MutS binds specifically to a heteroduplex primer-template complex containing a GT transition mismatch (for every AC mismatch there is a GT mismatch) or a small bulge loop and not to a perfectly matched primer-template complex, thus interfering with initiation of polymerization from the mismatched template. Addition of Apy MutL or Tma MutL enhances primer-directed allele-specific PCR. For example, addition of Apy MutL or Tma MutL enhances binding of Apy MutS and Tma MutS to bulge loops in the heteroduplex primer-template nucleic acid.

Allele-specific primers forming a GT mismatch can be synthesized, although thermostable mismatch binding proteins, can bind to other types of heteroduplexes, which binding is enhanced in the presence of one or more thermostable proteins that enhance binding of thermostable mismatch binding proteins to bulge loops in a heteroduplex nucleic acid. Of greater importance, any selection against primer-template mismatches throughout the length of a primer-template complex should translate into fewer improper extension products for all PCR reactions. Compatibility between allele-specific amplification conditions and long PCR conditions (Cheng, S. et al., *Proc. Natl. Acad. Sci. USA* 91: 5695–5699 (1994)) is considered.

Isolated, recombinant thermostable MutL protein or a portion thereof, and suitable fusion proteins can be used in methods for enhancing allele-specificity (e.g., in methods for enhancing mismatch-specific TaqMan PCR, such as in methods for detecting mismatches formed between heteroduplex template-oligonucleotide nucleic acids, and in methods for enhancing primer-directed allele-specific PCR).

The present invention also relates to methods for selecting against amplification of mismatches between complementary strands. Specifically, the present invention relates to methods for selecting against amplification of heteroduplex nucleic acid.

FIDELITY OF DNA REPLICATION

The present invention further relates to methods of reducing DNA misincorporation (i.e., improving fidelity of DNA replication) in an amplification reaction.

Replication errors are frequent with all thermostable polymerases, even using the optimum conditions (Eckert, K. A. and Kunkel, T. A., *PCR. Methods. Appl.* 1: 17–24 (1991); Ling, L. L. et al., *PCR. Methods. Appl.* 1: 63–69 (1991)). Comparing optimal conditions, the 3'→5' editing exonuclease activity of a polymerase will decrease PCR errors by no more than 2–5 fold. The majority of errors introduced during PCR amplification are transitions (Keohavong, P. et al., *PCR. Methods. Appl.* 2: 222–292 (1993)). Improvement of fidelity depends upon the ability of MutS to bind heteroduplex nucleic acid tightly and provide a nucleus for renaturation following the strand-separation step of PCR. MutL can enhance MutS binding to heteroduplex nucleic acid. A renatured PCR product would not act as a template for subsequent amplification. Apy and Tma MutS and MutL proteins are ideal candidates for use in PCR because they were cloned from hyperthermophiles.

The ultimate specificity of mismatch-specific TaqMan PCR can be determined by the frequency at which wild-type templates are amplified, in spite of the selection against them, and at which misincorporation produces the mutant sequence.

MISINCORPORATION

Fidelity with and without Apy or Tma MutS and MutL can be assayed by determining the frequency of mutations introduced during amplification of lacI$^q$ which prevent expression of a functional lac repressor protein.

As described in the Examples, a simple blue-white screen was developed for measuring PCR fidelity. A plasmid derived from pUC19 was kindly provided by Dr. Y. Ioannou (Mount Sinai School of Medicine) in which the 880 bp sequence from the AatII site (GACGTC . . . ) to the AflIII site ( . . . ACATGT) was replaced by GACTCTAGAG-GATCCATGT (SEQ ID NO:16), introducing an XbaI site and a BamHI site. pET11a (Novagen, Inc.) was cleaved with BstYI to produce ends compatible with BamHI and ligated into the BamHI-cleaved modified pUC19 vector. A clone was selected which contained the pET11a fragment from 748 to 1961, containing the complete lacI$^q$ gene, and was designated pUC17I. *E. coli* KL318 (K.B. Low) was obtained from the *E. coli* Genetic Stock Center (#4350). This lacI22 strain was constitutive for expression of lacZ and able to cleave 5-bromo-4-chloro-3-indolyl-β-D-galactoside (X-gal) to produce a blue color. Transformation by pUC17I led to expression of lacI$^q$ and repression of lacz. One set of PCR primers, 5' AUGAUGAUGAUGAUCGCACATTTC-CCCGAAAAGTG 3' (SEQ ID NO:17) and 5' AUCAU-CAUCAUCAUGCGCGGAACCCCTATTTGT 5' (SEQ ID NO:18), was used to amplify pUC17I. The products were phenol/chloroform extracted and purified on Millipore Ultrafree MC 30,000 NMWL filters before digestion with one unit uracil-DNA glycosylase (UDG) in 30 mM Tris (pH 8.3), 50 mM KCl, 5 mM MgCl$_2$ for 1 hr at 37° C. The circularized products were introduced into *E. coli* KL318 by electroporation. An alternative set of PCR primers was prepared which required restriction endonuclease cleavage and ligation before electroporation. In both cases, the cells were propagated at several dilutions on plates containing ampicillin, isopropyl-β-D-thiogalactopyranoside (IPTG) and X-gal. In both cases, the presence of a subset of blue colonies indicated failure to produce active LacI$^q$ due to a mutation introduced during PCR. There was little advantage of one set of primers and cloning conditions over the other.

Amplification reactions can be carried out with or without added Apy or Tma MutS±MutL protein. The relative numbers of blue colonies is a measure of the efficacy of the thermostable MutS±MutL proteins in blocking mismatch-containing PCR products, resulting from polymerization errors, from acting as templates in subsequent rounds of PCR.

Several thermostable DNA polymerases (e.g., Taq, Vent) may be suitable in the amplification reaction. Initially, published PCR conditions known to optimize for fidelity of a particular polymerase can be used, and PCR conditions can be varied to verify optimum polymerase fidelity. Subsequently, each of the appropriate variables affecting PCR can be modified to optimize for replication fidelity in the presence of Apy and Tma MutS±MutL, even if polymerase fidelity in the absence of a thermostable MutS±MutL protein is suboptimal. The optimized results in the presence of thermostable MutS±MutL proteins can be compared to the optimized results without MutS±MutL to determine the fold improvement in PCR fidelity for the two MutS and MutL proteins for each of the polymerases.

DECREASED STUTTERING/SLIPPAGE AT DINUCLEOTIDE AND TRINUCLEOTIDE REPEATS

Fidelity with and without Apy or Tma MutS and MutL can also be assayed by determining the extent of frameshift mutation ("stuttering"/"slippage") during amplification of di-and trinucleotide repeats. In the absence of these repeats, most of the replication errors are known to be transitions. For di- and trinucleotide repeats, most of the errors are known to be frameshifts.

Amplification of the highly polymorphic dinucleotide and trinucleotide repeats in human genomic for gene mapping usually results in ladders of bands thought to be due to polymerase "stuttering"/"slippage." D10S183 (MFD200, 124–158 bp) and D4S171 (MFD22, 143–161 bp) were used to amplify human genomic DNA. One primer was labeled with $^{32}$P. The products were separated on DNA sequencing gels and analyzed by autoradiography. The expected ladders of bands were observed. It is reasonable to expect that one or more sets of primers for highly polymorphic trinucleotide repeats can also be found which will give reproducible ladders with a spacing of 3 nucleotides.

Whatever the mechanism of stuttering/slippage, the ladders must reflect denaturation and amplification of PCR intermediates with 2 or 3 nucleotide loops similar to those found in heteroduplexes formed between pUC19Δ3 and pUC19Δ1 or pUC19GC, respectively. In preliminary experiments, MutS alone was ineffective at reducing stuttering. However, if thermostable MutS +MutL proteins prevents extension of slipped templates, these ladders can be reduced or eliminated, thus making the use of these polymorphic markers more convenient for genomic mapping and fingerprinting.

Amplification of representative di- and trinucleotide repeat regions of human DNA can be carried out in the presence and absence of Apy or Tma MutS+MutL to optimize conditions. Each of the appropriate variables affecting PCR can be modified to optimize for replication fidelity in the presence of Apy and Tma MutS+MutL, as measured by reduction or elimination of stuttering/slippage.

HETERODUPLEX BINDING AND DETECTION

Many of the DNA manipulations described herein involve standard techniques and procedures (Sambrook, J. et al., *Molecular Cloning, A Laboratory Manual*, 2nd edition, Cold Spring Harbor University Press, New York, 1989).

As described herein, the mismatch binding assay (also referred to herein as the gel shift binding assay or the gel shift assay) was used to evaluate the MutL proteins of the present invention for the ability to enhance binding of thermostable mismatch binding proteins to bulge loops in a heteroduplex nucleic acid. Proteins other than MutL can also be evaluated for the ability to enhance binding of thermostable mismatch binding proteins to bulge loops in a heteroduplex nucleic acid using this assay. The mismatch binding assay is also used to evaluate thermostable mismatch binding proteins for specific binding to bulge loops in a heteroduplex nucleic acid. Protein complexes can also be evaluated for specific binding to bulge loops in a heteroduplex nucleic acid using the gel shift assay. As used herein, a "protein complex" includes a molecular complex of two or more proteins.

As described in the Examples, to make heteroduplex substrates for use in evaluating thermostable MutS and MutL proteins for specific binding to bulge loops in a heteroduplex nucleic acid, several modifications were introduced into pUC19 by replacing the KpnI to PstI segment of the polylinker. In pUC19GC, the BamHI site GGATCC in the sequence GGGGATCCTC (SEQ ID NO:10) was modified to substitute a C for the first T to yield GGGGACCCTC (SEQ ID NO:11). The resultant plasmid gained an AvaII site. In pUC19Δ1, a T was inserted into the pUC19GC polylinker sequence GGGGACCCTC (SEQ ID NO:11) to yield GGGGATCCCTC (SEQ ID NO:12) and reconstitute the BamHI site. In pUC19Δ3, a T and two Cs were inserted into the pUC19GC polylinker sequence GGGGACCCTC (SEQ ID NO:11) to yield GGGGATCCCCCTC (SEQ ID NO:13) and again reconstitute the BamHI site. The sequences were verified.

In addition to pUC19GC, pUC19CG and pUC19TA can be similarly constructed to study transversion substitutions using the same oligonucleotide probes.

PCR products of 337–340 bp were synthesized from pUC19, pUC19GC, pUC19Δ1 and pUC19Δ3 using 5' TACGCCAGCTGGCGAAAGGG 3' (SEQ ID NO:14) and 5' AATGCAGCTGGCACGACAGG 3' (SEQ ID NO:15), where the PvuII sites are underlined. PCR products up to 2.7 kb can be prepared using appropriate primers. For some experiments, one of the primers was labeled with $^{32}P$ using T4 polynucleotide kinase to allow quantitation of products.

PCR products of 337–340 bp can be synthesized from pUC19CG and pUC19TA using 5' TACGCCAGCTGGCGAAAGGG 3' (SEQ ID NO:14) and 5' AATGCAGCTGGCACGACAGG 3' (SEQ ID NO:15), where the PvuII sites are underlined. PCR products up to 2.7 kb can be prepared using appropriate primers.

Heteroduplexes were formed in PCR and similar buffers from various ratios of two different PCR products by denaturation at about 97° C. and annealing at about 67° C. (Wetmur, J. G., *Crit. Rev. Biochem. Mol. Biol.* 26: 227–259 (1991)). Heteroduplexes between pUC19GC (or pUC19) and pUC19Δ3 were easily separated from homoduplexes on a 6% polyacrylamide gel. Heteroduplexes between pUC19Δ1 and pUC19Δ3, while less separated from homoduplexes because of a loop size of two rather than three, were easily distinguished. Heteroduplexes between pUC19GC (or pUC19) and pUC19Δ1, as well as heteroduplexes between pUC19 and pUC19GC, could not be distinguished from homoduplexes using this gel system. In particular, the homoduplexes, differing by only 3 base pairs, had almost identical mobilities. The heteroduplexes had reduced mobility. Denaturation and fast cooling prevented complete renaturation and revealed a slower-moving denatured DNA band. Addition of Apy MutS protein led to a gel shift of the heteroduplex band and appearance of a new band for the complex. Denaturation and fast cooling in the presence of the thermostable Apy MutS demonstrated that the specific binding to the heteroduplex was preserved.

Heteroduplexes were formed between pUC19GC prepared with one labeled primer and unlabelled pUC19Δ1 or pUC19 using the unlabeled molecule in excess so that most of the label is in heteroduplex and not homoduplex. Similarly, heteroduplexes can be formed between pUC19GC prepared with one labeled primer and unlabelled pUC19CG or pUC19TA using the unlabeled molecule in excess so that most of the label is in heteroduplex and not homoduplex. AvaII cleavage was tested for the ability to deplete residual homoduplexes without affecting the heteroduplexes.

Heteroduplexes can also be formed by reversing the choice of labeled PCR product and renaturation driver. For example, heteroduplexes can be formed by using labeled pUC19. BamHI cleavage can similarly be tested for the ability to deplete residual homoduplexes without affecting the heteroduplexes. Labeled heteroduplexes were also formed using pUC19GC and pUC19Δ3.

Heteroduplex formation with duplex molecules leads to two types of mismatches. For example, with pUC19 plus pUC19GC heteroduplexes, GT and AC mismatches were created simultaneously. Hybridization of the plus strand of pUC19GC with the complementary strand of pUC19 DNA leads to an AC mismatch, whereas hybridization of the plus strand of pUC19 with the complementary strand of pUC19GC DNA leads to a GT mismatch. Heteroduplex formation between pUC19Δ1 and pUC19GC leads to molecules with unpaired A or T residues. Heteroduplex formation between pUC19Δ3 and pUC19GC leads to molecules with three unpaired GGA or TCC residues. These mismatches were evaluated independently by the choice of radiolabeled primer, using the gel shift assay.

MutS binding assays employed a 1:20 dilution of each of the heteroduplex mixtures or homoduplex controls from PCR buffer into 20 mM Tris, pH 7.5, 5 MM $MgCl_2$, 0.1 mM DTT, 0.01 mM EDTA to give approximately 5 μg/ml total DNA. Thermostable MutS and MutL proteins purified to homogeneity were used in the assays. However, using the MutS binding assays described, any protein purified to homogeneity can be evaluated for specific binding to bulge loops in a heteroduplex nucleic acid. In addition, using the MutS binding assays described, any protein purified to homogeneity can be evaluated for the ability to enhance specific binding of a second protein or combination of proteins to bulge loops in a heteroduplex nucleic acid.

Variables in the MutS binding assays include protein concentration (stoichiometry), temperature, pH, added KCl and added $Mg^{++}$. After incubation in the presence or absence of thermostable mismatch repair proteins (MutS±MutL), the products were separated by electrophoresis at 25 V/cm for 30 minute on a 6% polyacrylamide gel at 4° C. in 0.2×TBE and analyzed either by ethidium bromide staining and UV fluorography or by autoradiography. As used herein, "thermostable mismatch repair proteins" refer to thermostable proteins that are associated with nucleic acid mismatch repair and include thermostable mismatch binding proteins (e.g., thermostable MutS proteins), thermostable proteins that enhance binding of a thermostable mismatch binding protein to bulge loops in a heteroduplex nucleic acid (e.g. thermostable MutL proteins), and thermostable proteins associated with nucleic acid strand discrimination (e.g., thermostable MutH proteins).

The effects of temperature, pH, and salts in the loading and running buffers of the gel shift assay can be adjusted to provide for a set of standard assay conditions where specific binding to bulge loops of the thermostable mismatch repair proteins to be evaluated is not affected by the assay conditions. For the assay to have no effect, protein exchange must not take place during the assay. To determine the assay conditions most permissive of sample variability, identical measurements can be carried out with and without unlabeled mismatch-free DNA and/or heteroduplexes added to the loading buffer. In some measurements, the unlabeled DNA can be added to the incubation mixture before preparation for electrophoresis.

In preliminary experiments where electrophoresis was carried out at 4° C., which may not be desirable with thermophilic proteins, addition of mismatch-free duplex DNA was necessary to suppress non-specific binding of Apy MutS to homoduplex DNA.

To investigate thermostability of Apy MutS and MutL, Tma MutS and MutL proteins, and other thermostable MutS and Mut L proteins, after incubation at constant temperature in PCR buffer, aliquots of the MutS and Mut L proteins were removed as a function of time and tested for binding activity in the standard assay.

One variable in the specificity of MutS±MutL binding is MutS and MutL stoichiometry to heteroduplex DNA. Thus, to investigate specificity of MutS±MutL binding to the set of heteroduplexes, addition of competing mismatch-free superhelical or linear dsDNA, or ssDNA, were used as an assay for non-specific binding. The linear dsDNA can be varied in size to test for end effects. Other variables include incubation temperature and time, pH, KCl and $Mg^{++}$ concentrations.

MutS proteins all contain a Walker motif, GxxxxGKS, which has been implicated in NTP binding. Although inclusion of ATP or ATPγS in the Apy MutS binding assay to a 3 nucleotide loop had no effect on the binding stoichiometry, possible effects on affinity for other mismatches, such as those resulting from transversions, can be determined.

To investigate thermostability of each of the complexes formed between Apy MutS±MutL and Tma MutS±MutL with the set of radiolabeled heteroduplex nucleic acids, after complex formation, unlabeled PCR product identical to the labeled PCR product used for heteroduplex nucleic acid formation can be added to restore 1:1 stoichiometry. After incubation at a particular temperature, renaturation to completion and deproteinization, the fraction of newly-formed unlabeled heteroduplex nucleic acid, up to 50% of the total DNA, will reflect homoduplex nucleic acid strand separation and the fraction of newly-formed labeled homoduplex nucleic acid, up to 50% of the labeled DNA, will reflect mismatch binding protein-heteroduplex nucleic acid complex strand separation. The relative strand-separation temperatures of heteroduplex nucleic acid complexes and uncomplexed homoduplex nucleic acids in conditions compatible with PCR can thus be determined.

KINETICS OF HETERODUPLEX BINDING

The reverse rate (dissociation rate) can be determined by measuring the rate of exchange from a MutS±MutL complexed with a radiolabeled heteroduplex nucleic acid to a competing unlabeled heteroduplex nucleic acid using a variety of solvent conditions. For example, in preliminary experiments, 1 mM ATPγS was observed to retard dissociation exchange of Apy MutS from a pUC19–pUC19Δ3 heteroduplex DNA to competing DNA. The pUC19–pUC19Δ3 heteroduplexes with only MutS bound are sufficiently stable to permit gel-shift analysis and can be used as the unlabeled heteroduplex nucleic acid for investigating the complete set of radiolabeled heteroduplex nucleic acids. To determine whether exchange requires dissociation of mismatch binding proteins from the labeled heteroduplex DNA before binding to competing DNA, the effects of the concentrations of specific competing heteroduplex DNA or non-specific competing native DNA were determined. Thus, the optimum conditions favoring heteroduplex nucleic acid stability consistent with specificity and PCR can be found.

The forward rate (binding rate) can be determined using a variety of solvent conditions where the dissociation rate is slow. Binding can be terminated as a function of time by adding competing DNA, and the fraction of labeled heteroduplex DNA complexed to mismatch binding proteins can be determined. The forward rate constant for MutS±MutL binding to a mismatch cannot be greater than approximately $2 \times 10^8$ $M^{-1}s^{-1}$, the diffusion control limit, unless binding is mediated through exchange from non-specific binding sites. For example, the half-time for the diffusion controlled reaction would be approximately 0.6 sec at 12.5 nM target each of heteroduplex DNA (e.g. 50% of 100 ng/20 µl) and MutS (50 ng/20 µl). Lower concentrations permit determination of binding rate constants. Thus, the MutS±MutL concentration(s) necessary for specific, stable and rapid mismatch binding in conditions compatible with PCR can be found. To be effective, this binding to a mismatch must occur before the DNA polymerase initiates DNA polymerization in primer-directed allele-specific PCR primers or copies the template in mismatch-specific TaqMan PCR.

NUCLEASE PROTECTION ASSAYS

Footprints of Apy and Tma MutS±MutL binding to the set of radiolabeled heteroduplex nucleic acids can be determined by electrophoresis on sequencing gels following limited endonuclease digestion of heteroduplex nucleic acids labeled first at one end and then at the other. Footprinting can also be attempted using the 5'→3' exonuclease activity of thermostable Taq DNA polymerase, in the absence of dNTPs, and the 3'→5' exonuclease activity of thermostable Vent DNA polymerase in a manner akin to the use of the 3'→5' exonuclease activity of T7 DNA polymerase with E. coli MutS (Ellis, L. A. et al., Nucleic Acids Res. 22: 2710–2711 (1994)). Thus, the footprints can be obtained for both mismatch and bulge-loop defects. These footprints aid in the design of TaqMan oligonucleotides and allele-specific PCR primers.

OTHER MISMATCHES

Transitions and small frameshifts are the mutations known to be the most effective mismatch binding protein substrates. However, transversion mutations can be effective mismatch binding protein substrates. Optimal conditions for binding of mismatch binding proteins to TC, CC, TT, GA, GG and AA mismatches can be tested after the design and production of additional PCR templates.

PRIMER EXTENSION ASSAYS

Mismatched TaqMan primers (mismatches or bulge loops) can be used to form complexes with Apy MutS plus MutL as well as Tma MutS plus MutL. Radiolabeled primer extension products synthesized by Taq or Tth polymerase and its derivatives (e.g. Stoffel fragment and other enzymes lacking 5'→3' exonuclease activity) and blocked by these complexes can be analyzed by electrophoresis on sequencing gels. In designing TaqMan oligonucleotides, to determine the closest distance of approach of the polymerase to the mismatch, a set of TaqMan oligonucleotides can be constructed with increasing 5' extensions well beyond the mismatch position.

MISMATCH-SPECIFIC TaqMan PCR

Allele-specific amplification with a mismatched internal oligonucleotide demonstrates that propagation of polymerization can be inhibited by forming a mismatch binding protein-internal duplex mismatch complex. To optimize the choice of DNA polymerases, thermostable mismatch binding proteins and internal oligonucleotide design in terms of both PCR sensitivity and allele specificity, DNA polymerization through matched and mismatched TaqMan primer-template complexes may be examined. Unlike the primer-directed allele-specific system, MutS- plus MutL-mediated selective amplification occurs at each PCR cycle. The assay (TaqMan PCR) is based on the "TaqMan" system first described by Holland, P. M. et al., Proc. Natl. Acad. Sci. U.S.A. 88: 7276–7280 (1991). As used herein, the terms "TaqMan oligo", "TaqMan oligonucleotide" and "TaqMan primer" refer to an internal oligonucleotide. As used herein, an "internal oligonucleotide" is an example of a blocking oligonucleotide.

In one set of experiments, the PCR template mixture is a serial dilution of pUC19GC with constant concentrations of pUC19, pUC19Δ1 or pUC19Δ3. Commercial human DNA is added to 1 μg/reaction. One set of PCR primers can be the two PvuII-containing primers described previously (SEQ ID NO:14 and SEQ ID NO:15). Additional primers can be synthesized to produce longer PCR products. A third TaqMan oligonucleotide can match the AvaII-containing region of pUC19GC or the corresponding region of one of the other templates.

Results with Taq DNA polymerase amplification of pUC19GC and pUC19Δ3 in the presence of a TaqMan oligonucleotide, Apy MutS and Apy MutL are presented in Example 8 (see the Table) and demonstrate that the complete TaqMan system works.

In other experiments, pUC19 is subjected to serial dilution. The TaqMan oligonucleotide can match the BamHI containing region of one of the templates. Templates that can be held at constant concentration are described above and include pUC19GC, pUC19Δ1, pUC19Δ3, pUC19CG and pUC19TA.

Many TaqMan oligonucleotides can be synthesized and tested, with the design informed by the experiments described herein. These oligonucleotides can contain a 3' terminal phosphate residue to prevent extension by Taq DNA polymerase or its derivatives, which lack 3'→5' exonuclease activity.

When present at a concentration in excess of the PCR primer concentrations, TaqMan oligonucleotide-template complexes form efficiently, and bound TaqMan oligonucleotide is degraded by the 5'→3' exonuclease activity of Taq polymerase during the polymerization step of PCR. In the case of derivatives like Stoffel fragment that lack 5'→3' exonuclease activity, the TaqMan oligonucleotide is displaced. All of the assay conditions can be tested for efficient degradation or displacement of radiolabeled Taqman oligonucleotides. Because only the PCR products from the pUC19GC template can be cleaved by AvaII and only the PCR products from pUC19, pUC19Δ1 or pUC19Δ3 can be cleaved by BamHI, the relative yields of the two PCR products can be determined by cleavage with AvaII, BamHI or both enzymes, gel electrophoresis, and fluorography or autoradiography.

Apy and Tma MutS and MutL proteins can be examined independently for their ability to recognize TaqMan oligonucleotide-template complexes and inhibit the propagation step of polymerization during PCR. Other proteins can also be examined for their ability to recognize TaqMan oligonucleotide-template complexes and inhibit the propagation step of polymerization during PCR or for their ability to enhance binding of thermostable mismatch binding proteins to TaqMan oligonucleotide-template complexes and thus enhance blocking of the propagation step of polymerization during PCR.

Taq DNA polymerase has a processivity of about 60 nucleotides at the maximum rate of polymerization (about 50 nucleotides/second). When Taq polymerase encounters a mismatch binding protein-heteroduplex nucleic acid complex, the most likely scenario is dissociation of the polymerase. However, if a bound polymerase is capable of displacing the mismatch binding protein-heteroduplex nucleic acid complex, altering variables such as (i) the dilution of the mismatched template in the carrier DNA (the complexity), (ii) the nature of the mismatch and bulge loops formed between the Taqman oligonucleotides and the template (e.g., pUC19 or pUC19GC), (iii) the detailed position of the mismatch in the TaqMan oligonucleotide, (iv) the spacing between the initiation PCR primer and the TaqMan oligonucleotide, (v) the DNA polymerase, (vi) the MutS+ MutL source, (vii) the number of PCR cycles, (viii) the cycling conditions, (ix) salt and DNTP concentrations, and (x) the absolute and relative concentrations of the DNA polymerase, the MutS, the MutL and the TaqMan oligonucleotide, in a manner leading to reduced processivity, should lead to dissociation. Thus, these variables can be optimized in the mismatch-specific TaqMan PCR system.

The TaqMan reader manufactured by the Applied Biosystems Division of Perkin-Elmer can be used to investigate high throughput screening methods. This reader detects fluorescent products in a 96-well plate after transfer from PCR tubes in a compatible format. One possible format for its use in testing the variables described above with Taq polymerase and derivatives retaining the 5'→3' exonuclease activity is to use a second TaqMan oligonucleotide, containing a fluor and quencher, which precisely matched a new sequence cloned into pUC19 and pUC19GC. This format allows use of a single fluor-quencher TaqMan oligonucleotide for all of the experiments.

In addition to specificity, it is important to achieve the highest possible sensitivity. One approach to achieving single molecule sensitivity is preamplification for several or many cycles before the addition of the TaqMan primer, MutS and MutL. Preamplification might be necessary if MutS±MutL inhibits PCR of matched templates at all and/or if more than one mutation were to be detected in a single amplicon. Mismatch-specific TaqMan PCR technology is amenable to automation. On a chip, screening for many mutant alleles can easily be accomplished in parallel, and preamplified DNA is the obvious input. However, this design may be limited if PCR misincorporation errors lead to false positive results. Thus, preamplified products from a single template and mismatched primers differing by a single transition can be tested as input. The products that escape selection can be tested for the appearance of a restriction endonuclease cleavage site.

Because the TaqMan oligonucleotide is not incorporated into the amplification product, the same selection takes place at each cycle, permitting geometric selection. In addition to selection at each PCR cycle, another advantage of inhibition of propagation rather than initiation is that more time will be available for the formation of the thermostable MutS-heteroduplex nucleic acid complex before the critical polymerase inhibition step takes place. This simple closed tube technology for detecting mutant alleles in a vast excess of normal alleles has important applications in the study of cancer and cancer epidemiology.

PRIMER-DIRECTED ALLELE-SPECIFIC AMPLIFICATION

Allele-specific amplification with matched primers demonstrates that binding of a thermostable mismatch binding protein to a variety of mismatched primer-template complexes inhibits initiation of polymerization.

In one embodiment of primer-directed allele-specific amplification, the PCR template is a mixture containing one of the pUC19 derivatives described previously (especially pUC19GC and pUC19Δ1) and pMS19, a derivative of pUC19 with inserts of 35 bp at both the EcoRI and HindIII sites but with a polylinker region identical to pUC19 (Weinstock, P. H. and Wetmur, J. G., *Nucleic Acids Res.* 18: 4207–4213 (1990)). One primer was selected from the PvuII-containing primers described herein (SEQ ID NO:14 or SEQ ID NO:15). The reverse primer was synthesized to match either the BamHI-containing region of pMS19 or the corresponding region of one of the pUC19 derivatives. Two types of primer-template mismatches can thus be prepared and each seen in two contexts. The additional 35 bp in PCR products derived from pMS19 permitted easy identification of products following polyacrylamide gel electrophoresis and ethidium bromide staining. Quantitative autoradiography can also be employed to identify products. In addition to mismatch type (especially GT and AC mismatches and single frameshift mutations), efficiency of inhibition of amplification by MutS±MutL binding also depends on PCR conditions and the location of the mismatch within the primer.

Mismatches not only affect the melting temperature of the primer-template complex (Wetmur, J. G., *Crit. Rev. Biochem. Mol. Biol.* 26:227–259 (1991)), but also the initiation of extension by the thermostable DNA polymerase. For each assay, template ratios may need adjustment to produce equal yields of the PCR products from the two templates in the absence of Apy or Tma MutS±MutL. Using this system, a 10–20 fold improvement was achieved in allele-specific PCR with mismatches 7–9 nucleotides away from the 3' end of the primer. Typically, mismatches that far from the polymerase binding site have little effect on initiation efficiency.

The effect of Apy and Tma MutS±MutL on the ratio of PCR products can be examined as a function of MutS±MutL concentration and thermostable DNA polymerase concentration. This ratio must be high enough to permit nearly complete MutS±MutL binding to first-round primer template complexes before the polymerase has an opportunity to bind and initiate extension. Cycling parameters can be adjusted as appropriate. Input template concentration and KCl and $Mg^{++}$ concentrations can also be adjusted. Compatibility of the system with dI and dU incorporation may also be examined.

As used herein, the terms "template", "template nucleic acid", "target template" and "target nucleic acid" are defined as a nucleic acid, in purified or nonpurified form, which comprises the specific sequence desired (nucleotide sequence of interest). Any nucleic acid can be utilized as the template. The nucleic acid can be obtained from any source, for example, from plasmids such as pBR322, from cloned DNA or RNA, or from natural DNA or RNA from any source, including bacteria, yeast, viruses, organelles, and higher organisms such as plants and animals. DNA or RNA may be extracted from blood, tissue material such as chorionic villi, or amniotic cells by a variety of techniques. (See, e.g., Sambrook, J. et al., *Molecular Cloning, A Laboratory Manual*, 2nd edition, Cold Spring Harbor University Press, New York, 1989). Thus, the template may be DNA or RNA, including messenger RNA, which DNA or RNA may be single-stranded or double-stranded. In addition, a DNA-RNA hybrid which contains one strand of each may be utilized. A mixture can also be used, as can nucleic acids produced from a previous amplification reaction (using the same or different primers). The template may be only a fraction of a large molecule or can be present initially as a discrete molecule, so that the specific sequences constitutes the entire nucleic acid.

If the nucleic acid is double-stranded, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90 to 105° C. for times generally ranging from about 0.5 to 5 minutes. Preferably the effective denaturing temperature is 90–100° C. for 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSH-Quantitative Biology*, 43: 63 (1978), and techniques for using RecA are reviewed in C. Radding, *Ann. Rev. Genetics*. 16: 405–437 (1982). The denaturation produces two separated complementary strands of equal or unequal length.

The term "oligonucleotide" as used herein is defined as a molecule comprised of 8 or more deoxyribonucleotides and typically 20–40 deoxyribonucleotides. Its exact size will depend on many factors, which in turn depend on the ultimate function or use of the oligonucleotide. The oligonucleotide may be derived synthetically or may be isolated from natural sources by cloning, for example.

As used herein, an oligonucleotide which is designed to be completely complementary to a specific nucleotide sequence of interest hybridizes to the complementary region of the strand of the template which includes the nucleotide sequence of interest to form a homoduplex nucleic acid. The oligonucleotide which is designed to be completely complementary to a specific nucleotide sequence of interest hybridizes to a strand of a nucleic acid which does not include the nucleotide sequence of interest to form a heteroduplex nucleic acid. An oligonucleotide which is designed to be completely complementary to a specific nucleotide sequence of interest can be a primer, a blocking oligonucleotide or a probe.

The term "primer" as used herein refers to an oligonucleotide, whether occurring naturally as in a purified restriction digest for example, or produced synthetically, which is capable of acting as a point of initiation of synthesis when placed under conditions in which primer extension is initiated. Synthesis of a primer extension product which is complementary to a nucleic acid strand is usually initiated in the presence of four different nucleoside triphosphates and an inducing agent such as DNA polymerase in an appropriate buffer and at a suitable temperature and pH. The specific buffer, temperature and pH depend on the inducing agent and the amplification method used.

The primer is preferably single stranded for maximum efficiency in amplification, but may alternatively be double stranded. If double stranded, the primer is first treated to separate its strands before being used to prepare extension products. The primer, as used in nucleic acid amplification reactions, is single-stranded. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. For example; for diagnostics applications, depending on the complexity of the target sequence, the oligonucleotide primer typically contains 15–25 or more nucleotides, although it may contain fewer nucleotides. For other applications, the oligonucleotide primer is typically shorter, e.g., 8–15 nucleotides. Such short primer molecules generally require cooler temperatures to form sufficiently stable hybrid complexes with template.

The term "blocking oligonucleotide" refers to an oligonucleotide, whether occurring naturally as in a purified restriction digest or produced synthetically, which is capable of inhibiting propagation of polymerization of a primer extension product (i.e., inhibiting elongation of the extension product) when placed under conditions in which primer extension product is elongated. Propagation of a primer extension product which is complementary to a nucleic acid strand typically occurs in the presence of four different nucleoside triphosphates and an inducing agent such as DNA polymerase and at a suitable temperature and pH.

The blocking oligonucleotide is preferably single stranded for maximum efficiency in amplification, but may alternatively be partially complementary. For DNA amplification methods, the blocking oligonucleotide is an oligodeoxyribonucleotide. The blocking oligonucleotide must be sufficiently long to permit formation of the heteroduplex template-blocking oligonucleotide complex. The exact lengths of the blocking oligonucleotides will depend on many factors, including temperature, source of primer and use of the method. The blocking oligonucleotide must be modified at the 3' end to prevent its function as a primer (e.g., modified with 3' phosphate with Taq polymerase which lacks 3'→5' editing exonuclease activity). The "Taqman oligonucleotide" or "internal oligonucleotide" is an example of a blocking oligonucleotide.

The term "probe" as used herein includes an oligonucleotide, whether occurring naturally as in a purified restriction digest for example, or produced synthetically, which is capable of being covalently fused or ligated together into a product which is complementary to a nucleic acid strand of the target template when placed under conditions in which product formation is initiated. Formation of a product which is complementary to a nucleic acid strand is initiated in the presence of a fusing agent such as DNA ligase in an appropriate buffer and at a suitable temperature and pH. The specific buffer, temperature and pH will depend on the fusing agent and the amplification method used.

The probe is preferably single stranded for maximum efficiency in amplification, but may alternatively be double stranded. If double stranded, the probe is first treated to separate its strands before being used to prepare amplified products. The probe, as used in nucleic acid amplification reactions, is single-stranded. Preferably, the probe is an oligodeoxyribonucleotide. The probe must be sufficiently long to provide the desired specificity (i.e., to avoid being hybridized to random sequences in a sample). Typically, probes on the order of 15 to 100 bases serve this purpose. The exact lengths of the probes will depend on many factors, including temperature, source of primer and use of the method.

In one embodiment, oligonucleotides designed to be completely complementary to a specific nucleotide sequence of interest, whether a primer, blocking oligonucleotide, or probe, can be designed for use in pairs, one oligonucleotide to anneal to and block the amplification of each complementary strand of the template, for example, in a control sample (i.e., in a sample of nucleic acids known to not include the nucleotide sequence of interest). Complementary overlap between oligonucleotides designed to be completely complementary to a specific nucleotide sequence of interest should be minimized to avoid the stable annealing of the oligonucleotides to each other.

In another embodiment, oligonucleotides designed to be completely complementary to a specific sequence of interest, whether a primer, blocking oligonucleotide, or probe, can be designed for use as a single oligonucleotide, annealing to and blocking the amplification of one strand of the template, for example, in a control sample (i.e., in a sample of nucleic acids known to not include the nucleotide sequence of interest).

The following is an illustration of the use of MutS and MutL proteins with oligonucleotides designed to be completely complementary to a specific sequence of interest to test for the presence of the specific sequence of interest in a sample of nucleic acids or mixture of nucleic acids. The sample of nucleic acids may be purified or unpurified, as in a sample of lysed cells or tissue.

For use in a method for detecting a nucleic acid which includes a specific sequence of interest, an oligonucleotide, whether a primer, a blocking oligonucleotide or a probe, is selected to be completely complementary to the specific sequence of interest. In a particular embodiment, the specific sequence of interest is a mutation. If the specific sequence of interest is included in the nucleic acid being assessed, the oligonucleotide will hybridize to the complementary region of the strand of the nucleic acid which includes the specific sequence of interest to form a homoduplex nucleic acid. MutS protein does not bind to a homoduplex nucleic acid and thus, in the case where the oligonucleotide selected is a primer, initiation of polymerization of a primer extension product occurs (the desired amplification product is synthesized).

If initiation of polymerization of a primer extension product is blocked, then the specific sequence thought to be included in the nucleic acid is likely not included in the nucleic acid. In this case, a nucleic acid strand and the primer have formed a heteroduplex containing a bulge loop which has been bound by MutS, indicating the presence of a mismatch or small insertion or deletion in the nucleic acid strand related to the primer. MutL protein enhances binding of the MutS protein to bulge loops in the heteroduplex nucleic acid.

In the case where the oligonucleotide selected is a blocking oligonucleotide, propagation of polymerization of a primer extension product (i.e., elongation of the extension product) occurs (the desired amplification product is synthesized). If propagation of polymerization of a primer extension product (i.e., elongation of the extension product) is blocked, then the specific sequence thought to be included in the nucleic acid is likely not included in the nucleic acid. In this case, a nucleic acid strand and blocking oligonucleotide have formed a heteroduplex containing a bulge loop which has been bound by MutS, indicating the presence of a mismatch or small insertion or deletion in the nucleic acid strand related to the blocking oligonucleotide. MutL protein enhances binding of the MutS protein to bulge loops in the heteroduplex nucleic acid.

In the case where the oligonucleotide selected is a probe, amplification of target nucleic acid occurs. If amplification of the nucleic acid is blocked, then the specific sequence thought to be included in the nucleic acid is likely not included in the nucleic acid. In this case, a nucleic acid strand and probe have formed a heteroduplex containing a bulge loop which has been bound by MutS, indicating the presence of a mismatch or small insertion or deletion in the nucleic acid strand related to the probe. MutL protein enhances binding of the MutS protein to bulge loops in the heteroduplex nucleic acid.

The amount of amplification product synthesized in each case is referred to herein as the amount of amplification product synthesized in a sample which comprises template nucleic acids assessed for the specific sequence of interest.

As a negative control, a mixture containing (1) a nucleic acid which does not have the specific sequence thought to be included in the template being evaluated (i.e., containing only mismatched versions of the template being evaluated) and (2) the oligonucleotide designed to be completely complementary to the specific sequence thought to be included in the template being evaluated, is maintained under (a) conditions in which primer extension is initiated in the case where the oligonucleotide is a primer or under (b) conditions in which primer extension product is elongated in the case where the oligonucleotide is a blocking oligonucleotide or under (c) conditions in which target template is amplified in the case where the oligonucleotide is a probe. The amount of amplification product synthesized in the control is compared to the amount of amplification product synthesized in a sample which comprises template nucleic acids assessed for the specific sequence of interest. If the amount of amplification product synthesized in the sample which comprises template nucleic acids assessed for the specific sequence of interest is the same as or less than the amount of amplification product synthesized in the control, the specific sequence of interest is likely not included in the template nucleic acid. In the case of the opposite result (if the amount of amplification product synthesized in the sample which comprises template nucleic acids assessed for the specific sequence of interest is greater than the amount of amplification product synthesized in the control), the specific sequence of interest is likely included in the template nucleic acid.

In a method for selecting against a nucleic acid comprising a specific sequence, an oligonucleotide is designed to form heteroduplexes with a strand of the nucleic acid being selected against. That is, the oligonucleotide is designed to be less than completely complementary to the specific nucleotide sequence being selected against (but sufficiently complementary that hybridization occurs). An oligonucleotide which is less than completely complementary to the nucleotide sequence being selected against comprises one or more nucleotide mispairings with a nucleic acid strand in the region of the specific sequence being selected against when the oligonucleotide and nucleic acid strand hybridize together in that region, resulting in the formation of a bulge loop in the heteroduplex nucleic acid. An oligonucleotide which is less than completely complementary to the nucleotide sequence being selected against can be a primer, a blocking oligonucleotide or a probe.

Oligonucleotides may be prepared using any suitable method, such as, for example, the phosphotriester and phosphodiester methods, or automated embodiments thereof. In one such automated embodiment diethylphosphoramidites are used as starting materials and may be synthesized as described by Beaucage et al., *Tetrahedron Letters* 22: 1859–1962 (1981). Oligonucleotides can also be synthesized by phosphoramidite chemistry in a Milligene 8750 DNA synthesizer according to the manufacturer's specification. One method for synthesizing oligonucleotides on a modified solid support is described in U.S. Pat. No. 4,458, 066. It is also possible to use a primer which has been isolated from a biological source (such as a restriction endonuclease digest).

The thermostable proteins of the present invention which enhance binding of thermostable mismatch binding proteins to bulge loops in a heteroduplex nucleic acid may be used with thermostable mismatch binding proteins in any methods of amplification of nucleic acids to improve fidelity or to improve allele-specific amplification. For example, the binding of thermostable mismatch binding proteins such as MutS proteins to DNA containing replication errors caused by misincorporation by a DNA polymerase, can improve the fidelity of the sequence of DNA in amplification methods, and has applications, for example, in the cloning of a true copy of genomic DNA. Addition of a thermostable protein that enhances binding of thermostable mismatch binding proteins to bulge loops can improve this result.

Where searching or assaying for DNA of a specific sequence among a mixture of many DNA molecules, methods of DNA amplification rely on the specificity of primer oligonucleotides annealing to a perfectly matched complementary strand in the template DNA. The addition to amplification reactions of a thermostable mismatch binding protein that binds to bulge loops formed when primer-template mismatches occur, and that prevents extension from the primer, can eliminate or greatly reduce the amplification from sites at which the primer-template complementarity is less than perfect. Addition of a thermostable protein that enhances binding of thermostable mismatch binding proteins to bulge loops can improve this result. Variations on this method can be used to detect particular nucleic acid sequences that occur in cancer and in various genetic diseases.

The methods of the present invention are based on known methods of amplification of nucleic acids. Reagents used in the methods can be added sequentially or simultaneously. If a method of strand separation, such as heat, is employed which will inactivate the inducing agent, as in the case of a heat-labile enzyme, then it is necessary to replenish the inducing agent after every strand separation step.

PCR is an example of an amplification technique. PCR refers to an amplification technique where a pair of primers (one primary and one secondary) is employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to increase geometrically the number of target sequence molecules. PCR is described further in U.S. Pat. No. 4,683,195; U.S. Pat. No. 4,683,202; U.S. Pat. No. 4,800,159; and U.S. Pat. No. 4,965,188. Many variations of PCR are known. (See, e.g., Ausubel, F. M. et al., Current Protocols in Molecular Biology, John Wiley & Sons Inc., New York, 1994).

LCR is another example of an amplification technique. LCR refers to an amplification technique where two primary (first and second probes) and two secondary (third and fourth) probes are employed in excess. The first probe hybridizes to a first segment of the target strand and the second probe hybridizes to a second segment of the target strand, the first and second segments being contiguous so that the primary probes abut one another in 5' phosphate-3' hydroxyl relationship and so that a ligase can covalently fuse or ligate the two probes into a fused product. In addition, a third (secondary) probe can hybridize to the first probe and a fourth (secondary) probe can hybridize to the second probe in a similar abutting fashion. If the target is initially double stranded, the secondary probes will also hybridize to the target complement in the first instance. Once the fused strand of primary probes is separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described further in, for example, EP-A-320 308 and European Application No. 0 439 182 A2 (published Jul. 31, 1991).

The methods herein may be used to enable detection and/or characterization of particular nucleic acid sequences associated with infectious diseases, genetic disorders or cellular disorders such as cancer, e.g., oncogenes. For example, the methods herein may be used to detect early mutations in cells in sputum, feces, urine, or blood which predispose cells to progress to malignancy. The methods herein may be used in metastasis (e.g., for screening lymph nodes for cells containing the same mutations found in a primary solid tumor or for detecting reoccurrence of a hematological disease).

One embodiment of the invention relates to detecting nucleic acids which include a specific nucleotide sequence comprising combining a thermostable mismatch binding protein which binds specifically to bulge loops in a heteroduplex nucleic acid, a thermostable protein that enhances binding of the thermostable mismatch binding protein to the bulge loops, and an amplification reaction mixture, to produce a test combination. The individual components of an amplification reaction mixture can each be added, together or separately (e.g., individually), in any order, prior to, subsequent to or simultaneously with the thermostable mismatch binding protein which binds specifically to bulge loops in a heteroduplex nucleic acid, and/or the thermostable protein that enhances binding of the thermostable mismatch binding protein to the bulge loops. The resulting test combination is maintained under conditions appropriate for nucleic acid amplification to occur (i.e., synthesis of extension product). The amount of extension product synthesized in the test combination is determined and compared with the amount of product synthesized in a corresponding negative control (the control amount) to determine if the specific nucleotide sequence suspected of being present in the nucleic acids being assessed is present. If the amount of product synthesized in the test combination is the same as or less than the amount of product synthesized in the corresponding negative control, then the nucleic acids being assessed do not include the specific nucleotide sequence. If the amount of product synthesized in the test combination is greater than the amount of product synthesized in the corresponding control, then the nucleic acids being assessed include the specific nucleotide sequence. In a particular embodiment, the specific nucleotide sequence is a mutation.

In a particular embodiment, the components of an amplification reaction mixture include (1) a nucleic acid to be assessed for a specific nucleotide sequence of interest; (2) four different nucleoside triphosphates; (3) two oligonucleotide primers where each primer is selected to be complementary to different strands of the nucleic acid which includes the specific nucleotide sequence of interest such that the extension product synthesized from one primer, when separated from its complement, can serve as a template for synthesis of the extension product of the other primer, at a temperature which promotes hybridization of each primer to its complementary strand; (4) a blocking oligonucleotide completely complementary to the specific nucleotide sequence of interest; (5) a thermostable enzyme which catalyzes combination of the nucleoside triphosphates to form primer extension products complementary to each strand of the nucleic acid which includes the specific nucleotide sequence of interest; and (6) an amplification buffer suitable for the activity of the enzyme. Thus, for example, one or more of the different nucleoside triphosphates can be added prior to, subsequent to or simultaneously with the thermostable mismatch binding protein which binds specifically to bulge loops in a heteroduplex nucleic acid and/or the thermostable protein that enhances binding of the thermostable mismatch binding protein to the bulge loops. One or more of the primers can be added prior to, subsequent to or simultaneously with one or more of the different nucleoside triphosphates, the thermostable mismatch binding protein and/or the thermostable protein that enhances binding of the thermostable mismatch binding protein to the bulge loops. Similarly, the blocking oligonucleotide, the thermostable enzyme, the nucleic acid to be assessed for the nucleotide sequence of interest and/or the amplification buffer can each be added prior to, subsequent to or simultaneously with one or more of the different nucleoside triphosphates, one or more of the primer, the thermostable mismatch binding protein and/or the thermostable protein that enhances binding of the thermostable mismatch binding protein to the bulge loops. The blocking oligonucleotide, the thermostable enzyme, the nucleic acid to be assessed for the nucleotide sequence of interest, and the amplification buffer can also be added in any order relative to each other. In another embodiment, the amplification reaction mixture further includes a second blocking oligonucleotide designed to be completely complementary to the complementary strand of the nucleotide sequence of interest. Complementary overlap between the second blocking oligonucleotide and the first blocking oligonucleotide (the blocking oligonucleotide designed to be completely complementary to the specific nucleotide sequence of interest) should be minimized to avoid the stable annealing of the oligonucleotides to each other.

In a further embodiment, the components of an amplification reaction mixture include (1) a nucleic acid to be assessed for a specific nucleotide sequence of interest; (2) four different nucleoside triphosphates; (3) two oligonucleotide primers where each primer is selected to be complementary to different strands of the nucleic acid which includes the specific nucleotide sequence of interest, with one primer completely complementary to the nucleotide sequence of interest, such that the extension product synthesized from one primer, when separated from its complement, can serve as a template for synthesis of the extension product of the other primer, at a temperature which promotes hybridization of each primer to its complementary strand; (4) a thermostable enzyme which catalyzes combination of the nucleoside triphosphates to form primer extension products complementary to each strand of the nucleic acid which includes the specific nucleotide sequence of interest; and (5) an amplification buffer suitable for the activity of the enzyme. In a particular embodiment, the amplification reaction mixture further include a blocking oligonucleotide completely complementary to the complementary strand of the specific nucleotide sequence of interest.

In another embodiment, the components of an amplification reaction mixture include (1) a nucleic acid to be assessed for a specific nucleotide sequence of interest; (2) four oligonucleotide probes, two primary and two secondary probes, with one primary probe completely complementary to the nucleotide sequence of interest and one secondary probe completely complementary to the complementary strand of the nucleotide sequence of interest; (3) a thermostable enzyme which catalyzes fusion of oligonucleotide probes to form amplified products complementary to each strand of the nucleic acid which includes the specific nucleotide sequence of interest; and (4) an amplification buffer suitable for the activity of the enzyme. In a particular embodiment, one of the probes which is completely complementary to the nucleotide sequence of interest is omitted.

The three embodiments describing components of the amplification reaction mixture are not intended to be limiting in any way. In each particular embodiment, the amplification reaction mixture can further include additional components, such as, for example, components which enhance the activity of thermostable enzymes to catalyze combination of nucleoside triphosphates to form primer extension products or components which enhance and/or improve the amplification reaction and/or the utility of the amplification procedure. The components of an amplification reaction mixture and amplification conditions depend upon the particular amplification procedure being employed and can be determined from readily available sources. See, for example, Ausubel et al., *Current Protocols In Molecular Biology*, John Wiley & Sons, New York, 1994; Sambrook et al., *Molecular Cloning: A Laboratory Manual*, 2nd ed., Cold Spring Harbor Laboratory Press, New York, 1989; U.S. Pat. No. 4,683,195; U.S. Pat. No. 4,683,202; U.S. Pat. No. 4,800,159; U.S. Pat. No. 4,965,188; European Patent Application No. 0 416 677 A1 (published Mar. 13, 1991); Holland et al., *Proc. Natl. Acad. Sci. USA* 88:7276–7280 (1991); Livak et al., *Nat. Genet.* 9:341–342 (1995); Saiki et al., *Proc. Natl. Acad. Sci. USA* 86:6230–6234 (1989); Nickerson et al., *Proc. Natl. Acad. Sci. USA* 87:8923–8927 (1990); Kwok et al., *Nucleic Acids Res.* 18:999–1005 (1990); Tada et al., *Cancer Res.* 53:2472–2474 (1993); Bottema et al., *Methods Enzymol.* 218:388–402 (1993); Wiedmann et al., *PCR Methods & Applications* 3:S51–64 (1994); Felley-Bosco et al., *Nucleic Acids Res.* 19:2913–2919 (1991); Cha et al., *PCR Methods. Appl.* 2:14–20 (1992); Hruban et al., *Am. J. Pathol.* 143:545–554 (1993); Sidransky et al., *Science* 256:102–105 (1992); and Hsu et al., *Carcinogenesis* 15:1657–1662 (1994). These references are entirely incorporated herein by reference. The components of an amplification mixture further depend on whether the specific nucleotide sequence of interest is in, for example, a region of high GC content or a region of high AT content.

Oligonucleotide-template hybridizations are more stable in regions of high GC content than in regions of high AT content. Thus, if the specific nucleotide sequence of interest is in, for example, a region of high AT content, one embodiment of the invention can be to select two oligonucleotide primers to be complementary to different strands of a nucleic acid which includes the specific nucleotide sequence of interest to hybridize therewith and a blocking oligonucleotide designed to be completely complementary to the specific nucleotide sequence of interest. If the specific nucleotide sequence of interest is in, for example, a region of high GC content, one embodiment of the invention can be to select primers to be complementary to different strands of a nucleic acid which includes the specific nucleotide sequence of interest to hybridize therewith, with one primer completely complementary to the specific nucleotide sequence of interest. In a particular embodiment, the specific nucleotide sequence of interest is a mutation.

As discussed above, oligonucleotides which are designed to be completely complementary to the specific nucleotide sequence of interest can be designed for use in pairs, one oligonucleotide to anneal to and block the amplification of each complementary strand of the template, for example, in a control sample (i.e., in a sample of nucleic acids known to not include the specific nucleotide sequence of interest). The oligonucleotides can also be designed for use as a single oligonucleotide, annealing to and blocking the amplification of one strand of the template, for example, in a control sample (i.e., in a sample of nucleic acids known to not include the specific nucleotide sequence of interest). If oligonucleotides are designed for use in pairs, complementary overlap between the oligonucleotides in a pair should be minimized to avoid the stable annealing of the oligonucleotides to each other.

Stabilizers can be included in the methods of the present invention. As used herein, for example, stabilizers increase the lifetime of a thermostable bulge loop-binding protein-heteroduplex nucleic acid complexes. For example, stabilizers herein increase the lifetime of MutS-heteroduplex nucleic acid complexes. A MutS-heteroduplex nucleic acid complex is a complex formed when MutS is bound to a bulge loop in a heteroduplex nucleic acid. ATPγS is an example of a stabilizer.

Other proteins which may be included in the methods of the present invention include those associated with nucleic acid strand discrimination (e.g., thermostable MutH or homologs thereof), those that enhance the activity of stabilizers to increase the lifetime of a thermostable bulge loop-binding protein-heteroduplex nucleic acid complexes, and those that enhance the activity of thermostable enzymes to catalyze combination of nucleoside triphosphates to form primer extension products.

The present invention will now be illustrated by the following examples, which are not intended to be limiting in any way.

EXAMPLES

Example 1

Genomic DNA, Plasmids, Nucleotides and Enzymes

All DNA manipulations used standard techniques and procedures (Sambrook, J. et al., *Molecular Cloning, A Laboratory Manual*, 2nd edition, Cold Spring Harbor: Cold Spring Harbor University Press (1989)). Genomic DNAs of *Thermotoga maritima* (Tma) and *Aquifex pyrophilus* (Apy) (Burggraf, S. et al., *System. Appl. Microbiol.* 15: 352–356 (1992)), both from cells supplied by Professor Karl Stetter, Universität Regensburg, were extracted for use as PCR templates and for Southern blots. Plasmids employed for cloning and expression were pUC19, pDG160/pDG182/pDG184 (Lawyer, F. C. et al., PCR. Methods. Appl. 2: 275–287 (1993)) and pET16b (Novagen, Inc.), which were grown in E. coli DH5Δ, DG116 (Lawyer, F. C. et al., PCR. Methods. Appl. 2: 275–287 (1993)) and BL21(DE3), respectively. All absorbance spectra were determined using a Hewlett-Packard diode array spectrophotometer equipped with a peltier temperature controller. Concentrations of DNA and primers were determined by using 50 and 36 μg ml$^{-1}$ A$_{260}$$^{-1}$, respectively, as conversion factors. Deoxynucleoside triphosphates were purchased from Boehringer-Mannheim. [α-$^{35}$S]dATP and [γ-$^{32}$P] ATP were purchased from NEN/DuPont. E. coli MutS protein was provided by U.S. Biochemical, Inc. UDG (uracyl DNA glycosylase, uracil N-glycosylase) was purchased from BRL, Inc. and used according to the manufacturer's instructions. Amplitaq DNA Polymerase, purchased from Perkin-Elmer, and native Taq polymerase, purchased from several suppliers, were used in the buffer supplied by the manufacturer. Restriction endonucleases, T4 polynucleotide kinase and T4 DNA ligase were purchased from New England Biolabs and used as recommended by the manufacturer. Simultaneous reactions with two or more restriction endonucleases were carried out in New England Biolabs NEB3 buffer. Simultaneous reactions with restriction endonucleases and T4 DNA ligase were carried out in the same buffer supplemented with 1 mM ATP.

Example 2

Oligodeoxynucleotides

All synthetic oligodeoxynucleotide primers for PCR and sequencing were synthesized on automated instruments using standard phosphoramidite chemistry.

Degenerate primers were constructed based on the following rules. First, the corresponding amino acid sequences should be identical in representative Gram-positive (e.g. E. coli) and Gram-negative organisms (e.g. S. pneumoniae) and should not be a common motif in unrelated proteins. For example, sequences satisfying this rule include MGDFYE, PNMGGK and FATHY located at positions 19, 614 and 725 in E. coli MutS, respectively. Similarly conserved sequences include IAAGEV and GFRGEA located at positions 14 and 93 in E. coli MutL, respectively. Second, the length of the sequence to be amplified should be kept as short as possible, consistent with obtaining an informative sequence in the PCR product, in order to maximize specific PCR amplification and minimize the likelihood of occurrence of EcoRI, BglII or BamHI sites which could interfere with subsequent cloning. Thus, degenerate primers based on MGDFYE were not used for the initial muts amplifications. Third, the degeneracy should be minimized by taking advantage of codon usage whenever possible. For example, in contrast to Thermus species, both Apy and Tma use AGR instead of CGN arginine codons more than 90% of the time. Fourth, except for the use of complete degeneracy in the last 5 nucleotides at the 3' end of a primer where a mismatch may have a deleterious effect on PCR, the following substitutions were made: G for R, C for Y, G/C for N. Reduced primer degeneracy increases primer template hybridization rates which can limit degenerate PCR (Wetmur, J. G. and Sninsky, J. J., In: PCR Strategies, Innis, M. A. et al., Eds., Academic Press, San Diego, pp. 69–83, 1995).

Primer construction is illustrated for muts cloning. The initial degenerate sense primer 5' GCGGAATTCC(G/C)AACATGGG(G/C)GG(A/C/G/T)AA 3' (SEQ ID NO:19) and antisense primer 5' GCGAGATCTAAGTAGTG(G/C)GT(A/C/G/T)GC(G/A)AA 3' (SEQ ID NO:20), corresponding to amino acids 615–620 and 725–729 in E. coli MutS, were used for cloning a fragment of the Apy and Tma muts genes. EcoRI (GAATTC) and BglII (AGATCT) recognition sequences are underlined.

Apy- and Tma-specific antisense primers, 5' GCGAGATCTCACCTGTCTTATGTAGCTCGA 3' (SEQ ID NO:21) and 5' GCGAGATCTCATCTCGACAAG-GAACGTACT 3' (SEQ ID NO:22), respectively, were employed together with a third degenerate sense primer, 5' GCGGAATTCATGGGGGA(C/T)TT(C/T)TA(C/T)GA 3' (SEQ ID NO:23), corresponding to amino acids 33–38 in E. coli MutS. Specific inverse primers for use with near the 5' end of the known sequence were 5' GCGGAATTCGG-GAAAGGATTCCCATGTTCG 3' (SEQ ID NO:24) and 5' GCGAGATCTCCTTTCCA-GCGGGTCTTGAAG 3' (SEQ ID NO:25) for Apy and 5' GCGGAATTCCGGGCATC-CCGTACCACTCGC 3' (SEQ ID NO:26) and 5' GCGAGATCTGGAGCGTCCCTGCCCTTCTTG 3' (SEQ ID NO:27) for Tma.

Specific inverse primers for use with near the 3' end of the known sequence were 5' GCGGAATTCTCAACCTTCATGAA-CGAGATG 3' (SEQ ID NO:28) and 5' GCGAGATCTCGAGCCTATTCTCAT-GAATAT 3' (SEQ ID NO:29) for Apy and 5' GCGGAAT-TCGAGGTGGGAAGAGGTACAAGC 3' (SEQ ID NO:30) and 5' GCGAGATCTCATCTCGACAAG-GAACGTACT 3' (SEQ ID NO:31) for Tma.

Additional sequencing primers lacking the GCG cap and restriction endonuclease sites were synthesized as required. These species-specific oligodeoxynucleotides were employed for Southern hybridization.

PCR primers for cloning Tma muts genes into pDG160 were 5' GCGAAGCTTATGAAGGTAACTCCCCTCATG 3' (SEQ ID NO:32) and 5' GCGGGATCCAC-GCATCGATACTGGTTAAAA 3' (SEQ ID NO:33), where the BamHI and HindIII sites are underlined and the initiation codon in the forward primer is shown in bold italics.

PCR primers for cloning Apy mutS genes into pDG182 and pDG184 and pET16b were 5' GCGCCATGGGAAAAGAGGA-GAAAGAGCTCA 3' (SEQ ID NO:34) and 5' GCGAGATCTGATACTCCAGAG-GTATTACAA 3' (SEQ ID NO:35) where the NcoI, which contains the initiation codon, and BglII sites are underlined.

Example 3

DNA AmDlification

PCR amplifications were carried out in a USA/Scientific Gene Machine II or an Ericomp PowerBlock system with DNA templates in 50–100 μl containing 1 μM of each primer, 10 mM Tris-HCl buffer, pH 8.3, 50 mM KCl, 25–50 units/ml Taq DNA polymerase, and 200 μM of each dNTP (Saiki, R. K. et al., Science 239: 487–491 (1988)). Typically, simultaneous reactions were initiated by addition of a MgCl$_2$ solution to Mg$^{++}$-free PCR mixtures at >80° C. to yield final concentrations of 0.8–2 mM followed by denaturation for 30 sec at 95° C. When using degenerate primers and 50 ng genomic DNA template, the first 5 cycles employed a 30 sec annealing step at 45° C. followed by a 2 min ramp to 72° C. before denaturation. An additional 30–35 cycles were carried out with a 55° C. annealing temperature. For inverse PCR (Ochman, H. et al., In PCR Protocols. A Guide to Methods and Applications, Innis, M. A. et al., Eds. (San Diego: Academic Press, Inc) pp. 219–227 (1990)), genomic DNA was digested to completion with a restriction endonuclease leaving a 3' or 5' 4-base overhang, phenol extracted, and ligated overnight at a DNA concentration of less than 50 μg/ml. When using unique direct or inverse PCR primers, templates of 50 ng genomic DNA or circularized genomic DNA, respectively, were employed, and the first 5 cycles were omitted.

Example 4

Cloning. Sequencing and Southern Hybridization

Products of PCR amplifications were phenol extracted to remove Taq polymerase and filtered on Millipore Ultrafree-MC 30,000 NMWL filter units to remove primers. PCR products with BglII cloning sites were cloned into pUC19 by simultaneous digestion of vector and insert with BglII, BamHI, and EcoRI, heat inactivation, ligation, and re-digestion with BamHI to destroy religated vectors without inserts. Inserts in pUC19, pDG160, pDG182, pDG184 and pET16b were sequenced in both orientations using insert-specific and vector-specific oligodeoxynucleotide rimers with the Sequenase DNA Sequencing Kit (U.S. Biochemicals, Inc.) or by cycle sequencing with Taq DNA polymerase using either $^{32}$P-labeled primers (Gibco-BRL kit) or fluorescent dideoxy terminators on an Applied Biosystems Automated DNA Sequencer. Southern hybridizations of restriction endonuclease-cleaved genomic DNAs were carried out with oligodeoxynucleotides labeled with $^{32}$P using T4 polynucleotide kinase. The genomic DNAs and restriction endonucleases were (1) Apy, none; (2) Apy, HindIII; (3) Apy, SacI; (4) Tma, BglII; (5) Tma; HindIII; (6) Tth, BamHI; (7) Tth, SacI; (8) Tth, none; (9) Taq, partial SacI; (10) Taq, SacI.

Example 5

Cloning and Sequence Analysis of mutS and mutL Genes From *Aquifex pyrophilus* and *Thermotoga maritima*

The cloning of the muts and mutL genes from *Aquifex pyrophilus* and *Thermotoga maritima* was accomplished without library construction using the same approach employed for the cloning of four thermophilic or hyperthermophilic RecA proteins (Wetmur, J. G. et al., *J. Biol. Chem.* 269: 25928–25935 (1994)). Fragments of Apy and Tma muts and mutL were amplified using a single set of degenerate PCR primers for each of the genes. Each primer began with GCG, followed by either an EcoRI or a BglII site, and followed by a degenerate nucleotide sequence.

The amplifications yielded unique products of the predicted length, which were cloned into pUC19 and sequenced using vector-specific primers. Although significant variation was observed for the translated sequence between the primers, Apy and Tma MutS and Apy and Tma MutL sequences were unmistakably those of MutS and MutL proteins, respectively. Longer (1.8 kb) fragments of both mutS genes were obtained using a unique antisense primer based on the newly acquired sequence and a degenerate sense primer based on the conserved MGDFYE sequence.

Unique inverse PCR cloning primers were synthesized corresponding to sequences near the 5' and 3' ends of each of the fragments and employed for amplifying genomic DNA circularized using various restriction endonucleases and DNA ligase. Southern blots were tested using sequence-specific oligodeoxynucleotides sequentially as probes. The Apy and Tma probes bound with equal efficiency only to Apy and Tma genomic DNA, respectively, but not to the DNA from several other species. These binding specificities demonstrated that the sequences amplified by PCR were derived from the sources stated. The inverse PCR steps were iterated as necessary until the sequences extended 5' from the initiation codon and well beyond the termination codon. To be certain that the sequences to be incorporated into the 5'-PCR expression primers accurately reflected the genomic sequence, the 5' sequence was verified by cycle sequencing.

The mutS and mutL genes from both of the hyperthermophiles were amplified using expression primers. Examples of expression primers are provided in Example 2. Products of several independent PCR reactions were digested with the appropriate restriction endonucleases and ligated into expression vectors. Clones which expressed a thermostable MutS or MutL were completely sequenced. The mutS and mutL amino acid sequences shown in FIGS. 10A–10B and 11A–11B, respectively, were determined to be authentic because they were identical in at least two independently-derived clones. The guanine plus cytosine content (G+C%) of all four complete sequences was approximately 47%, as expected.

A TFASTA analysis comparing the *E. coli* MutS amino acid sequence with the translated Apy and Tma MutS sequences is depicted in FIGS. 10A–10B. The numbers refer to amino acid positions in *E. coli* MutS. The TFASTA analysis depicted in FIGS. 10A–10B for Apy and *E. coli* (853 amino acids) MutS shows 36% identity in 792 amino acids overlap with length differences at the N- and C-termini of only 2 and 6 amino acids, respectively. The TFASTA analysis depicted in FIGS. 10A–10B for Tma and *E. coli* MutS shows a similar 37% identity in 783 amino acids overlap. However, Tma MutS showed significant variation at both the N- and C-termini. The analysis of the ends is outlined in FIG. 12. Following the last in-frame stop codon (TGA), the first ATG in Tma mutS matched the ATG at *E. coli* mutS codon 14. However, there were conserved threonine and proline codons at 3 and 2 positions upstream from this ATG in *E. coli*, Apy and Tma. Further examination of this upstream region revealed three valine codons (GTN). The most distal of these codons appeared to occur deep in the open reading frame of an upstream gene (termination TGA). The other two codons followed 5 and 11 nt after a sequence matching in 9 of 10 positions the 3' end of Tma 16S ribosomal RNA, 3' UUCCuCCACU 5' (Benson, D. et al., *Nucleic Acids Res.* 21: 2963–2965 (1993)). Because the 5 nt spacing separated the valine codon from the presumptive ribosome binding site by the optimal spacing, this codon was taken to be the initiation codon and was incorporated as ATG into the sense expression primer. This N-terminal was thus 7, rather than 13, and 5 amino acids shorter than *E. coli* and Apy MutS, respectively.

A PILEUP analysis comparing the MutL homolog *S. pneumoniae* (Spn) HexB and *E. coli* (Eco) MutL amino acid sequences with the coding sequences of Apy and Tma MutL is depicted in FIGS. 11A–11B. The positions of the N-terminal amino acids only varied by 1 amino acid. The initiation codon for Apy MutL was again a GTN codon and was incorporated as ATG into the sense expression primer. Only the N-terminal half of MutL proteins is conserved. TFASTA analysis with the first 200 amino acids of the MutL proteins showed that whereas Eco and Spn proteins were 50% identical, Apy MutL was 39, 42 and 45% identical to Spn HexB, Tma MutL and Eco MutL, respectively, and Tma MutL was 43% identical to both Eco MutL and Spn HexB.

The C-terminus of Tma MutS was 35 and 41 amino acids shorter than *E. coli* and Apy MutS, respectively. An investigation of the downstream flanking sequence revealed an open reading frame in reverse orientation which overlapped Tma MutS by 8 amino acids and which could encode a protein similar to that encoded by the D-ribulose-5-phosphate epimerase gene of *Alcaligenes eutrophus* and the dod gene of *Serratia marcescens*.

The major surprise came at the C-termini of the MutL proteins. Although this region of MutL is not generally conserved, the sizes of Eco MutL (615 amino acids), Spn HexB (649 amino acids) and other bacterial MutL sequences in Genbank are approximately the same. Tma and Apy MutL contain only 511 and 426 amino acids, respectively. The authenticity of the C-termini (e.g. no introns) was bolstered by the observation of a conserved CPHGRP(I/V) sequence 15–30 amino acids from the C-termini of the Apy MutL, Tma MutL and Spn HexB.

Cloning and sequence analysis of thermophilic mutS genes are also described in U.S. Application Ser. No. 08/468, 558 (filed Jun. 6, 1995), the teachings of which are entirely incorporated herein by reference.

Example 6
Phylogenetic Analysis of Apy and Tma MutS and MutL Protein Sequences

Nucleic acid and protein sequence analyses were carried out using programs in GCG (Devereux, J. et al., *Nucleic Acids Res.* 12: 387–395 (1984)). Because the guanine plus cytosine content of the hyperthermophiles was bout 47%, amino acid substitutions were not expected to reflect codon bias. TFASTA analysis of both MutS and MutL proteins and their homologs indicated that the amino acid sequences of the hyperthermophilic eubacteria, Gram-negative bacteria and Gram-positive bacteria were equally divergent, as had previously been observed using other proteins or 16S rRNA (Wetmur, J. G. et al., *J. Biol. Chem.* 269: 25928–25935 (1994); Burggraf, S. et al., *System. Appl. Microbiol.* 15: 352–356 (1992)).

Using PILEUP, the newly determined sequences of the thermophilic MutS and MutL proteins were aligned with related sequences in Genbank (Benson, D. et al., *Nucleic Acids Res.* 21: 2963–2965 (1993)) for at least two Gram-negative and two Gram-positive mesophilic bacteria and additional eukaryotic MutS or MutL homolog sequences. The multiple alignments were truncated to include only amino acids corresponding to 8–794 of *E. coli* MutS and 1–199 of *E. coli* MutL prior to analysis using PHYLIP (Phylogeny Inference Package) version 3.5c (Felsenstein, J., *Cladistics* 5: 164–166 (1989)). Pairwise distances between amino acids in the MutS and MutS homolog sequences were calculated using PROTDIST with the Dayhoff PAM matrix. Unrooted trees, calculated using FITCH with global rearrangement and jumbling before plotting with DRAWTREE, revealed Apy MutS, Tma MutS and the set of all mesophilic eubacterial MutS homologs to be equally divergent. The same result was observed for MutL.

Example 7
Expression and Purification of Apy and Tma MutS and MutL Proteins

Expression primers were a 5'-PCR primer containing a GCG cap, a restriction endonuclease site, an initiation ATG and the next 20 nucleotides of the coding sequence and a 3'-PCR primer containing a GCG cap, a second restriction endonuclease site and 21 nucleotides antisense to the downstream flanking sequence. PCR products from both species were ligated into pDG160/pDG182/pDG184 (APy) (Lawyer, F. C. et al., *PCR. Methods. Appl.* 2: 275–287 (1993)) or pET16b (Novagen, Inc.) and electroporated into *E. coli* DG116 (Lawyer, F. C. et al., *PCR. Methods. Appl.* 2: 275–287 (1993)) cells expressing the pLysS plasmid (Novagen, Inc) or BL21(DE3), respectively. The pLysS plasmid permits cell lysis by freeze-thaw.

Examples of PCR expression primers include 5' GCGAAGCTTATGAAGGTAACTCCCCTCATG 3' (SEQ ID NO:32) and 5' GCGGGATCCACGCATCGATACTGGT-TAAAA 3' (SEQ ID NO:33) for cloning Tma mutS genes into pDG160, where the BamHI and HindIII sites are underlined and the initiation codon in the forward primer is shown in bold italics, and 5' GCGCCATGGGAAAAGAG-GAGAAAGAGCTCA 3' (SEQ ID NO:34) and 5' GCGAGATCTGATACTCCAGAGGTATTACAA 3' (SEQ ID NO:35) for cloning Apy mutS genes into pDG182, pDG184 and pET16b, where the NcoI site, which contains the initiation codon, and BglII sites are underlined.

*E. coli* DG116 colonies derived from independent amplification reactions were grown overnight at 30° C. in LB-AMP-chloramphenicol, diluted 1/100 into the same medium and grown to $A_{600}$ approximately equal to 0.75, induced at 42° C. for 15 min, grown for an additional 3–5 hrs at 39° C., and collected by centrifugation for 15 min at 6,000 g. *E. coli* BL21(DE3) colonies were grown overnight at 37° C. in LB-AMP-chloramphenicol, diluted 1/100 into the same medium and grown to $A_{600}$ approximately equal to 0.75, induced with 1 mM IPTG, grown for an additional 5–12 hrs, and collected by centrifugation for 15 min at 6,000 g.

The pellets were resuspended in 300 pl 50 mM Tris-HCl, 1 mM PMSF, 1 mM DTT and 10 mM EDTA, pH 8 for each 100 ml of culture and subjected to 3 cycles of freezing in dry-ice ethanol and thawing at 37° C. Following sonication on ice to reduce the viscosity and centrifugation to remove cell debris, the samples were transferred to a new tube, made 0.3 M $(NH_4)_2SO_4$ by addition of 3 M stock, made 0.75% polyethylenimine (PEI) by addition of a neutralized 10% stock to precipitate DNA, heated to 75° C. for 15 min to denature thermolabile proteins, placed on ice for 30 min to aggregate the denatured proteins, cleared of DNA and denatured proteins by centrifugation, transferred to a new tube and frozen at −20° C. (optional). The partially purified MutS or MutL products were assayed for the presence of a thermostable protein of the correct size by SDS-PAGE. The presence of MutS or MutL bands was shown to depend upon the presence of the insert in the plasmid and induction by heat or IPTG.

Two purification schemes have been employed. In the first scheme, crude MutS or MutL, approximately 1 ml per 250 ml culture, was loaded onto a 1 ml HiTrap Q anion exchange column (Pharmacia), repeatedly washed with buffer and eluted with stepwise increases of NaCl (from about 0.1 M–2.0 M) in the same buffer. The eluate was loaded onto a 1 ml HiTrap SP anion exchange column (Pharamacia) or HiTrap blue affinity column (Pharmacia). Columns were washed extensively with stepwise increases of 0.5 M NaCl plus buffer and eluted in 1–2 M NaCl or 1–2 M guanidine HCl, respectively, in the same buffer. After dialysis and concentration using Centricon-30 (Amicon), protein concentrations were determined and compared with complete absorbance spectra to determine an extinction coefficient and to verify removal of nucleic acids. Purification from other proteins was verified by examination of overloaded SDS-PAGE. It is important to note that BL21 is not an endoA strain, so care must be exercised to assure removal of endonuclease I (non-specific dsDNA specific). Endonuclease I was verified to be thermostable and thermoactive.

In the second purification scheme, crude MutS or MutL as separated by BU hydrophobic chromatography on a PerSeptive Biosystems BioCAD SPRINT perfusion chromatography system. Again, removal of all nucleic acids was verified by an $A_{280}/A_{260}$ ratio greater than 1.5.

The thermostable MutS proteins showed a single band by SDS-PAGE. The overall yield of the thermostable MutS proteins from various preparations was approximately 0.2–0.3 mg/$10^{11}$ cells, corresponding to 2.5–4% of the initial protein content of the cells.

Purification of Apy MutL using the first purification scheme led to a mixture of two polypeptides, one at 75 kd and one at 45 kd. Of greatest importance, this MutL preparation was active in the TaqMan assay described in Example 8. The 75 kd protein, which matched *E. coli* MutL in size, was initially purified. This purified 75 kd protein was not active in the TaqMan assay. The 45 kd protein was subsequently purified and shown to be Apy MutL. One explanation for the lower yield of Apy MutL (about 0.5–1% of initial protein), compared to the yield of Apy MutS, may be the long 3' untranslated sequence. A similar yield was obtained with Tma MutL. Tailored mutL genes, recloned into pD6182, have led to improved yields.

Example 8

Allele-Specific PCR

In one experiment, two plasmid templates were mixed and used in 50 μl PCR reactions. In pUC19GC, the BamHI site in the pUC19 sequence GGGGATCCTC (SEQ ID NO:10) was modified to substitute a C for the first T to yield GGGGACCCTC (SEQ ID NO:11) with a new AvaII site. In pUC19Δ3, a T and two Cs were inserted into the pUC19GC polylinker sequence GGGGACCCTC (SEQ ID NO:11) to yield GGGGATCCCCTC (SEQ ID NO:13) and reconstitute the BamHI site. The PCR primers were located at the pUC19 PvuII sites. A TaqMan 28-mer oligonucleotide, terminating in a 3' P to prevent extension, matched pUC19GC completely and mismatched pUC19Δ3 eight nucleotides from its 5' end. The results of one TaqMan experiment using Taq Stoffel fragment DNA polymerase is shown in the Table.

TABLE

| Sample | 1 | 2 | 3 | 4 | 5 |
|---|---|---|---|---|---|
| pUC19Δ3 (pg) | 50 | 50 | 50 | 50 | 50 |
| PUC19GC (pg) | 50 | 2.5 | 0.25 | 0.025 | 0.0025 |
| % Cleavage of PCR product with MutS (1 μM) and no MutL (ND = None Detected) | | | | | |
| AvaII (pUC19GC) | 50 | 5 | ND | ND | ND |
| BamHI (PUC19Δ3) | 50 | 95 | 100 | 100 | 100 |
| % Cleavage of PCR product with MutS (1 μM) and MutL (0.2 μM) | | | | | |
| AvaII (PUC19GC) | 100 | 100 | 95 | 70 | 10 |
| BamHI (pUC19Δ3) | ND | ND | 5 | 30 | 90 |

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. An isolated thermostable protein having the amino acid sequence SEQ ID NO:40.

2. An isolated thermostable protein having the amino acid sequence SEQ ID NO:42.

3. An isolated thermostable MutL protein which is encoded by a nucleic acid characterized by the ability to hybridize under high stringency conditions to DNA having the nucleotide sequencey of its component of SEQ ID NO:39 and which enhances specific binding of a thermostable mismatch binding protein to bulge loops in a heteroduplex nucleic acid.

4. An isolated thermostable protein which is encoded by a nucleic acid characterized by the ability to hybridize under high stringency conditions to DNA having the nucleotide sequence of SEQ ID NO:41 and which enhances specific binding of a thermostable mismatch binding protein to bulge loops in a heteroduplex nucleic acid.

* * * * *

UNITED STATES PATENT AND TRADEMARK OFFICE
CERTIFICATE OF CORRECTION

PATENT NO. : 6,294,325 B1
DATED : September 25, 2001
INVENTOR(S) : James G. Wetmur It is certified that error appears in the above-identified patent and that said Letters Patent is hereby corrected as shown below:

Title page,
Item [54], delete "CLONING AND EXPRESSION OF THERMOSTABLE MULTI GENES AND PROTEINS AND USES THEREOF" and insert therefor -- CLONING AND EXPRESSION OF THEREMOSTABLE MUTL GENES --;

Claim 3,
Line 4, after the word "the", delete "nucleotide sequencey of its component" and insert therefor -- nucleotide sequence or its complement --;

Claim 4,
Line 1, after the word "isolated", delete "thermostable protein" and insert therefor -- therefor -- thermostable MutL protein --; and
Line 4, delete the words "sequence of SEQ ID NO:41" and insert therefor -- sequence or is complement of SEQ ID NO:41 --.

Signed and Sealed this

Twenty-sixth Day of February, 2002

Attest:

JAMES E. ROGAN
*Attesting Officer*     *Director of the United States Patent and Trademark Office*